United States Patent [19]
Mackenzie et al.

[11] Patent Number: 6,103,658
[45] Date of Patent: Aug. 15, 2000

[54] OLEFIN POLYMERIZATION CATALYSTS CONTAINING GROUP 8-10 TRANSITION METALS, PROCESSES EMPLOYING SUCH CATALYSTS AND POLYMERS OBTAINED THEREFROM

[75] Inventors: Peter Borden Mackenzie, Kingsport; Leslie Shane Moody, Johnson City; Christopher Moore Killian, Gray; James Allen Ponasik, Jr., Kingsport, all of Tenn.; Jason Patrick McDevitt, Wake Forest, N.C.; Gino Georges Lavoie, Kingsport, Tenn.

[73] Assignee: Eastman Chemical Company, Kingsport, Tenn.

[21] Appl. No.: 09/177,099

[22] Filed: Oct. 22, 1998

Related U.S. Application Data

[63] Continuation-in-part of application No. 09/088,223, Jun. 1, 1998, which is a continuation-in-part of application No. 09/030,058, Feb. 24, 1998, abandoned.

[60] Provisional application No. 60/062,609, Oct. 22, 1997, provisional application No. 60/040,363, Mar. 10, 1997, provisional application No. 60/041,542, Mar. 25, 1997, provisional application No. 60/042,925, Apr. 4, 1997, provisional application No. 60/043,406, Apr. 4, 1997, provisional application No. 60/044,691, Apr. 18, 1997, and provisional application No. 60/059,372, Sep. 18, 1997.

[51] Int. Cl.[7] .............................. B01J 31/00; B01J 31/02; B01J 31/12; B01J 31/16; B01J 31/18

[52] U.S. Cl. .................... 502/167; 502/122; 502/123; 502/126; 502/162; 502/168; 502/200; 556/35; 556/137; 556/138

[58] Field of Search ...................... 502/122, 123, 502/126, 162, 167, 168, 200, 216; 556/35, 137, 138

[56] References Cited

U.S. PATENT DOCUMENTS

| | | |
|---|---|---|
| 4,689,437 | 8/1987 | Murray . |
| 4,691,036 | 9/1987 | Helnz et al. . |
| 4,716,138 | 12/1987 | Murray . |
| 4,716,205 | 12/1987 | Klabunde . |
| 4,724,273 | 2/1988 | Fink et al. . |
| 4,906,754 | 3/1990 | Klabunde . |
| 5,030,606 | 7/1991 | Klabunde . |
| 5,175,326 | 12/1992 | Klabunde . |
| 5,714,556 | 2/1998 | Johnson et al. . |
| 5,852,145 | 12/1998 | McLain et al. . |
| 5,866,663 | 2/1999 | Brookhart et al. . |
| 5,880,241 | 3/1999 | Brookhart et al. . |
| 5,880,323 | 3/1999 | Brookhart et al. . |

FOREIGN PATENT DOCUMENTS

| | | |
|---|---|---|
| 381495 | 1/1990 | European Pat. Off. . |
| 96-70332 | 9/1997 | Japan . |
| 96-84343 | 10/1997 | Japan . |
| 96-84344 | 10/1997 | Japan . |
| 96/23010 | 8/1996 | WIPO . |
| WO 9637522 | 11/1996 | WIPO . |
| WO 9637523 | 11/1996 | WIPO . |
| 97/02298 | 1/1997 | WIPO . |
| 97/17380 | 5/1997 | WIPO . |
| 97/38024 | 10/1997 | WIPO . |
| 97/48735 | 12/1997 | WIPO . |
| 97/48736 | 12/1997 | WIPO . |
| 97/48737 | 12/1997 | WIPO . |
| 97/48742 | 12/1997 | WIPO . |
| 98/03521 | 1/1998 | WIPO . |
| 98/03559 | 1/1998 | WIPO . |
| WO 9830610 | 7/1998 | WIPO . |
| WO 9842664 | 10/1998 | WIPO . |
| WO 9842665 | 10/1998 | WIPO . |
| WO 9847934 | 10/1998 | WIPO . |
| WO 9856832 | 12/1998 | WIPO . |
| WO 9856837 | 12/1998 | WIPO . |
| WO 9856839 | 12/1998 | WIPO . |
| WO 9902472 | 1/1999 | WIPO . |

OTHER PUBLICATIONS

W. Marginggele, Zeitschrift Für Naturforschung, vol. 40b, No. 2, Feb., 1985, 277–281.
M. Doering, Zeitschrift Für Anorganische und Allgemeine Chemie, vol. 620, No. 3, 1994, 551–560.
Dirk Lindauer et al, J. Prakt. Chem./Chem.–Ztg. (1995), 337(2), 143–52 Coden: JPCCEM; ISSN: 0941–1216.
L. K. Johnson, et al., J. Am. Chem. Soc., 1995, 117, No. 23, Jun. 14, 1995, 6414–6415.
G. F. Schmidt et al., J. Am. Chem. Soc. 1985, 107,1443.
M. Brookhart et al, Macromolecules 1995, 28, 5378.
M. Peuckert et al., Organomet. 1983, 2 (5), 594.
W. Keim et al., Angew. Chem. Int. Ed. Eng. 1981, 20, 116.
V. M. Mohring et al., Angew. Chem. Int. Ed. Eng. 1985, 24, 1001.
G. Wilke, Angew. Chem. Int. Ed. Engl. 1988, 27, 185.
K.A.O. Starzewski et al., Angew. Chem. Int. Ed. Engl. 1987, 26, 63.
W. Maringgele, Zeitschrift Für Naturforschung, vol. 40b, No. 2, Feb., 1985, 277–281.
L. K. Johnson et al, Journal of the American Chemical Society, vol. 118, Oct. 10, 1996, 267–268.
Yasar Gok, Transition Metal Chemistry, vol. 20, No. 3, Jun. 1909, 225–319.

*Primary Examiner*—Mark L. Bell
*Assistant Examiner*—Michael J. DiVerdi
*Attorney, Agent, or Firm*—Jonathan D. Wood; Bernard J. Graves, Jr.; Harry J. Gwinnell

[57] ABSTRACT

Methods for preparing olefin polymers, and catalysts for preparing olefin polymers are disclosed. The polymers can be prepared by contacting the corresponding monomers with a Group 8–10 transition metal catalyst. The polymers are suitable for processing in conventional extrusion processes, and can be formed into high barrier sheets or films, or low molecular weight resins for use in synthetic waxes in wax coatings or as emulsions.

45 Claims, No Drawings

OLEFIN POLYMERIZATION CATALYSTS CONTAINING GROUP 8-10 TRANSITION METALS, PROCESSES EMPLOYING SUCH CATALYSTS AND POLYMERS OBTAINED THEREFROM

CROSS-REFERENCE TO RELATED APPLICATIONS

This Application claims the benefit under 35 U.S.C. § 119(e) of Provisional application Ser. No. 60/062,609, filed Oct. 22, 1997, and is a continuation-in-part application of U.S. application Ser. No. 09/088,223, filed on Jun. 1, 1998, which is a continuation-in-part of U.S. application Ser. No. 09/030,058, now abandoned, filed on Feb. 24, 1998, incorporated herein by reference, which claims the benefit under 35 U.S.C. § 119 (e) of Provisional application Ser. No. 60/040,363, filed Mar. 10, 1997; Provisional application Ser. No. 60/041,542, filed Mar. 25, 1997; Provisional application Ser. No. 60/042,925, filed Apr. 4, 1997; Provisional application Ser. No. 60/043,406, filed Apr. 4, 1997; Provisional application Ser. No. 60/044,691, filed Apr. 18, 1997, and Provisional application Ser. No. 60/059,372, filed Sep. 18, 1997.

FIELD OF THE INVENTION

The present invention is directed to Group 8–10 transition metal-containing complexes, their use in olefin polymerizations, and to novel olefin polymers produced thereby.

BACKGROUND OF THE INVENTION

Olefin polymers are used in a wide variety of products, from sheathing for wire and cable to film. Olefin polymers are used, for instance, in injection or compression molding applications, in extruded films or sheeting, as extrusion coatings on paper, for example photographic paper and digital recording paper, and the like. Improvements in catalysts have made it possible to better control polymerization processes, and, thus, influence the properties of the bulk material. Increasingly, efforts are being made to tune the physical properties of plastics for lightness, strength, resistance to corrosion, permeability, optical properties, and the like, for particular uses. Chain length, polymer branching and functionality have a significant impact on the physical properties of the polymer. Accordingly, novel catalysts are constantly being sought in attempts to obtain a catalytic process for polymerizing olefins which permits more efficient and better controlled polymerization of olefins.

Conventional polyolefins are prepared by a variety of polymerization techniques, including homogeneous liquid phase, gas phase, and slurry polymerization. Certain transition metal catalysts, such as those based on titanium compounds (e.g. $TiCl_3$ or $TiCl_4$) in combination with organoaluminum cocatalysts, are used to make linear and linear low density polyethylenes as well as poly-α-olefins such as polypropylene. These so-called "Ziegler-Natta" catalysts are quite sensitive to oxygen and are ineffective for the copolymerization of nonpolar and polar monomers.

Recent advances in non-Ziegler-Natta olefin polymerization catalysis include the following.

L. K. Johnson et al., WO Patent Application 96/23010, disclose the polymerization of olefins using cationic nickel, palladium, iron, and cobalt complexes containing diimine and bisoxazoline ligands. This document also describes the polymerization of ethylene, acyclic olefins, and/or selected cyclic olefins and optionally selected unsaturated acids or esters such as acrylic acid or alkyl acrylates to provide olefin homopolymers or copolymers.

European Patent Application Serial No. 381,495 describes the polymerization of olefins using palladium and nickel catalysts which contain selected bidentate phosphorous containing ligands.

L. K. Johnson et al., *J. Am. Chem. Soc.*, 1995, 117, 6414, describe the polymerization of olefins such as ethylene propylene, and 1-hexene using cationic α-diimine-based nickel and palladium complexes. These catalysts have been described to polymerize ethylene to high molecular weight branched polyethylene. In addition to ethylene, Pd complexes act as catalysts for the polymerization and copolymerization of olefins and methyl acrylate.

G. F. Schmidt et al., *J. Am. Chem. Soc.* 1985, 107, 1443, describe a cobalt(III) cyclopentadienyl catalytic system having the structure $[C_5Me_5(L)CoCH_2CH_2\text{---}||\text{---}H]^+$, which provides for the "living" polymerization of ethylene.

M. Brookhart et al., *Macromolecules* 1995, 28, 5378, disclose using such "living" catalysts in the synthesis of end-functionalized polyethylene homopolymers.

U. Klabunde, U.S. Pat. Nos. 4,906,754, 4,716,205, 5,030,606, and 5,175,326, describes the conversion of ethylene to polyethylene using anionic phosphorous, oxygen donors ligated to Ni(II). The polymerization reactions were run between 25 and 100° C. with modest yields, producing linear polyethylene having a weight-average molecular weight ranging between 8 K and 350 K. In addition, Klabunde describes the preparation of copolymers of ethylene and functional group containing monomers.

M. Peuckert et al., *Organomet.* 1983, 2(5), 594, disclose the oligomerization of ethylene using phosphine, carboxylate donors ligated to Ni(II), which showed modest catalytic activity (0.14 to 1.83 TO/s). The oligomerizations were carried out at 60 to 95° C. and 10 to 80 bar ethylene in toluene, to produce α-olefins.

R. E. Murray, U.S. Pat. Nos. 4,689,437 and 4,716,138, describes the oligomerization of ethylene using phosphine, sulfonate donors ligated to Ni(II). These complexes show catalyst activities approximately 15 times greater than those reported with phosphine, carboxylate analogs.

W. Keim et al., *Angew. Chem. Int. Ed. Eng.* 1981, 20,116, and V. M. Mohring, et al. *Angew. Chem. Int. Ed. Eng.* 1985, 24,1001. disclose the polymerization of ethylene and the oligomerization of α-olefins with aminobis(imino) phosphorane nickel catalysts; G. Wilke, *Angew. Chem. Int. Ed. Engl.* 1988, 27, 185, describes a nickel allyl phosphine complex for the polymerization of ethylene.

K. A. O. Starzewski et al., *Angew. Chem. Int. Ed. Engl.* 1987, 26, 63, and U.S. Pat. No. 4,691,036, describe a series of bis(ylide) nickel complexes, used to polymerize ethylene to provide high molecular weight linear polyethylene.

WO Patent Application 97/02298 discloses the polymerization of olefins using a variety of neutral N, 0, P, or S donor ligands, in combination with a nickel(0) compound and an acid.

Brown et al., WO 97/17380, describes the use of Pd α-diimine catalysts for the polymerization of olefins including ethylene in the presence of air and moisture.

Fink et al., U.S. Pat. No. 4,724,273, have described the polymerization of α-olefins using aminobis(imino) phosphorane nickel catalysts and the compositions of the resulting poly(α-olefins).

Recently Vaughan et al. WO 9748736, Denton et al. WO 9748742, and Sugimura et al. WO 9738024 have described the polymerization of ethylene using silica supported α-diimine nickel catalysts.

Additional recent developments are described by Sugimura et al., in JP96-84344, JP96-84343, by Yorisue et al., in JP96-70332, by Canich et al. WO 9748735, McLain et al. WO 9803559, Weinberg et al. WO 9803521 and by Matsunaga et al. WO 9748737.

Notwithstanding these advances in non-Ziegler-Natta catalysis, there remains a need for efficient and effective Group 8–10 transition metal catalysts for effecting polymerization of olefins. In addition, there is a need for novel methods of polymerizing olefins employing such effective Group 8–10 transition metal catalysts. In particular, there remains a need for Group 8–10 transition metal olefin polymerization catalysts with both improved temperature stability and functional group compatibility. Further, there remains a need for a method of polymerizing olefins utilizing effective Group 8–10 transition metal catalysts in combination with a Lewis acid so as to obtain a catalyst that is more active and more selective.

SUMMARY OF THE INVENTION

The present invention is directed to novel Group 8–10 transition metal catalysts, to batch or continuous olefin polymerizations using these catalysts, and to the polymers produced thereby.

The process of the present invention comprises contacting one or more olefin monomers of the formula LI:

RCH=CHR$^8$

LI wherein R$^1$ and R$^8$ each, independently, represent a hydrogen, a hydrocarbyl or a fluoroalkyl, and may be linked to form a cyclic olefin;

with a Group 8–10 transition metal having coordinated thereto a bidentate ligand having the formula X:

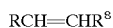

X

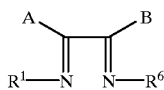

wherein R$^1$ and R$^6$ are each, independently, hydrocarbyl, substituted hydrocarbyl, or silyl, preferably sterically hindered aryl;

A and B are each, independently, a heteroatom connected mono-radical wherein the connected heteroatom is selected from Group 15 or 16, preferably N, O, S, and wherein A and B may be linked by a bridging group;

and, optionally, a Bronsted or Lewis acid; and polymerization is carried out to obtain a polymer comprising units of the aforementioned olefin monomer.

In the above process, it should be appreciated that the Group 8–10 transition metal has coordinated thereto a bidentate ligand having the formula X and that the Bronsted or Lewis acid is optionally reacted with this metal-ligand complex. In addition, the Bronsted or Lewis acid may be optionally combined with the ligand X prior to complexation to the Group 8–10 transition metal.

In addition, the process of the present invention comprises contacting one or more monomers of the aforementioned formula LI with a catalyst of the present invention having the following formula XI:

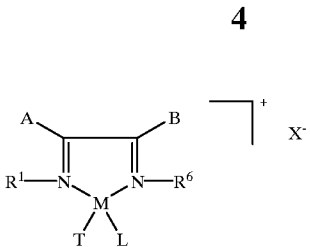

XI wherein R$^1$, R$^6$, A, and B are as in formula (X) above;

T represents a hydrogen or a hydrocarbyl;

L represents a mono-olefin or a neutral Lewis base wherein the coordinated atom is nitrogen, oxygen, or sulfur;

M represents a Group 8–10 transition metal, preferably Ni(II), Pd(II), Co(II) or Fe(II), more preferably Ni(II) or Pd(II);

and X$^-$ is a weakly coordinating anion; and polymerization is carried out to obtain a polymer comprising units of the aforementioned olefin monomer.

We believe that when T is hydrogen or hydrocarbyl and L is ethylene or a mono-olefin in formula XI above, then XI is the catalytically active specie. This active specie can be prepared by a number of different methodologies, including reaction of a zero-valent metal complex with a ligand of formula X and a Bronsted acid in the presence of ethylene or a mono-olefin. An example of this methodology includes the reaction of bis(1,5-cyclooctadiene)Ni(0) with a bidentate ligand of formula X and the ether solvate of hydrogen tetrakis[3,5-bis(trifluoromethyl)phenyl]borate in the presence of ethylene or a mono-olefin to generate an active catalyst of formula XI.

Further, the process of the present invention comprises contacting an olefin monomer of formula LI with a catalyst of the present invention, formed by combining a compound of formula (XII):

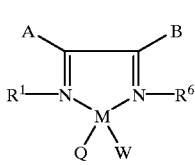

XII with a compound Y, selected from the group consisting of a neutral Lewis acid capable of abstracting Q$^-$ or W$^-$ to form a weakly coordinating anion, a cationic Lewis acid whose counterion is a weakly coordinating anion, or a Bronsted acid whose conjugate base is a weakly coordinating anion, wherein R$^1$, R$^6$, A, and B are as in formula X above;

Q represents an alkyl, chloride, iodide or bromide;

W represents an alkyl, chloride, iodide or bromide;

M represents a Group 8–10 transition metal, preferably Ni(II), Pd(II), Co(II), or Fe(II); and polymerization is carried out to obtain a polymer comprising units of the aforementioned olefin monomer.

The catalysts used in the processes of the present invention readily convert ethylene and α-olefins to high molecular weight polymers, and allow for olefin polymerizations under various conditions, including ambient temperature and pressure, and in solution.

The polymers of the present invention include homopolymers of olefins, such as polyethylene, polypropylene, and the like, and olefin copolymers, including functional-group containing copolymers. As an example, ethylene homopolymers can be prepared with strictly linear to highly branched structures by variation of the catalyst structure, cocatalyst composition, and reaction conditions, including pressure and temperature. The effect these parameters have on polymer structure is described herein. These polymers and copolymers have a wide variety of applications, including use as packaging material and in adhesives.

Accordingly, it is an object of the present invention to provide novel catalysts capable of polymerizing olefins, including functional group-containing olefins.

It is another object of the invention to set forth catalyst systems for olefin polymerizations.

It is a further object of the invention to describe olefin polymerizations under mild conditions.

It is yet another object of the invention to provide novel catalysts and processes for homogeneous olefin catalysis.

It is yet another object of the invention to provide novel catalysts and processes for heterogeneous gas or slurry phase olefin polymerization.

It is still a further object of the invention to provide novel polyolefins.

It is yet still another object of the invention to describe methods of varying catalyst structure and polymerization reaction conditions to vary the structure of the resultant polyolefin.

These and other objects, features, and advantages of the invention will become apparent as reference is made to the following detailed description and preferred embodiments.

DETAILED DESCRIPTION OF THE INVENTION

In this disclosure certain chemical groups or compounds are described by certain terms and symbols. These terms are defined as follows:

Symbols ordinarily used to denote elements in the Periodic Table take their ordinary meaning, unless otherwise specified. Thus, N, O, S, P, and Si stand for nitrogen, oxygen, sulfur, phosphorus, and silicon, respectively.

Examples of neutral Lewis acids include, but are not limited to, methylaluminoxane (hereinafter MAO) and other aluminum sesquioxides, $R^7_3Al$, $R^7_2AlCl$, $R^7AlCl_2$ (where $R^7$ is alkyl), organoboron compounds, boron halides. $B(C_6F_5)_3$, $BPh_3$, and $B(3,5-(CF_3)C_6H_3)_3$. Examples of ionic compounds comprising a cationic Lewis acid include: $R^9_3Sn$ [$BF_4$], (where $R^9$ is hydrocarbyl), $MgCl_2$, and $H^+X^-$, where $X^-$ is a weakly coordinating anion.

The term "weakly coordinating anion" is well-known in the art per se and generally refers to a large bulky anion capable of delocalization of the negative charge of the anion. Suitable weakly coordinating anions include, but are not limited to, $PF_6^-$, $BF_4^-$, $SbF_6^-$, $(Ph)_4B^-$ wherein Ph=phenyl, $^-BAr_4$ wherein $^-BAr_4$=tetrakis[3,5-bis(trifluoromethyl) phenyl]borate. The coordinating ability of such anions is known and described in the literature (Strauss. S. et al., Chem. Rev. 1993, 93, 927).

Examples of neutral Lewis bases include, but are not limited to, (i) ethers, for example, diethyl ether or tetrahydrofuran, (ii) organic nitriles, for example acetonitrile, (iii) organic sulfides, for example dimethylsulfide, or (iv) monoolefins, for example, ethylene, hexene or cyclopentene.

A "hydrocarbyl" group means a monovalent or divalent, linear, branched or cyclic group which contains only carbon and hydrogen atoms. Examples of monovalent hydrocarbyls include the following: $C_1-C_{20}$ alkyl; $C_1-C_{20}$ alkyl substituted with one or more groups selected from $C_1-C_{20}$ alkyl, $C_3-C_8$ cycloalkyl or aryl; $C_3-C_8$ cycloalkyl; $C_3-C_8$ cycloalkyl substituted with one or more groups selected from $C_1-C_{20}$ alkyl, $C_3-C_8$ cycloalkyl or aryl; $C_6-C_{14}$ aryl; and $C_6-C_{14}$ aryl substituted with one or more groups selected from $C_1-C_{20}$ alkyl, $C_3-C_8$ cycloalkyl or aryl; where the term "aryl" preferably denotes a phenyl, napthyl, or anthracenyl group. Examples of divalent (bridging) hydrocarbyls include: —$CH_2$—, —$CH_2CH_2$—, —$CH_2CH_2CH_2$—, and 1,2-phenylene.

A "silyl" group refers to a $SiR_3$ group wherein Si is silicon and R is hydrocarbyl or substituted hydrocarbyl or silyl, as in $Si(SiR_3)_3$.

A "heteroatom" refers to an atom other than carbon or hydrogen. Preferred heteroatoms include oxygen, nitrogen, phosphorus, sulfur, selenium, arsenic, chlorine, bromine, silicon and fluorine.

A "substituted hydrocarbyl" refers to a monovalent or divalent hydrocarbyl substituted with one or more heteroatoms. Examples of monovalent substituted hydrocarbyls include: 2,6-dimethyl-4-methoxyphenyl, 2,6-diisopropyl-4-methoxyphenyl, 4-cyano-2,6-dimethylphenyl, 2,6-dimethyl-4-nitrophenyl, 2,6-difluorophenyl, 2,6-dibromophenyl, 2,6-dichlorophenyl, 4-methoxycarbonyl-2, 6-dimethylphenyl, 2-tert-butyl-6-chlorophenyl, 2,6-dimethyl-4-phenylsulfonylphenyl, 2,6-dimethyl-4-trifluoromethylphenyl, 2,6-dimethyl-4-trimethylammoniumphenyl (associated with a weakly coordinated anion), 2,6-dimethyl-4-hydroxyphenyl, 9-hydroxyanthr-10-yl, 2-chloronapth-1-yl, 4-methoxyphenyl, 4-nitrophenyl, 9-nitroanthr-10-yl, —$CH_2OCH_3$, cyano, trifluoromethyl, or fluoroalkyl. Examples of divalent (bridging) substituted hydrocarbyls include: 4-methoxy-1,2-phenylene, 1-methoxymethyl-1,2-ethanediyl, 1,2-bis(benzyloxymethyl)-1,2-ethanediyl, or 1-(4-methoxyphenyl)-1,2-ethanediyl.

A "sterically hindered aryl" means (i) a phenyl ring with hydrocarbyl, substituted hydrocarbyl, F, Cl, Br or silyl substituents at both the 2- and 6 -positions, optionally substituted elsewhere with hydrocarbyl, substituted hydrocarbyl, F, Cl, Br, silyl, hydroxy, methoxy, nitro, cyano, phenylsulfonyl, $CO_2Me$, $CO_2H$, $C(O)CH_3$, $CF_3$, or fluoroalkyl substituents, (ii) a 2-substituted napth-1-yl ring, optionally substituted elsewhere with hydrocarbyl, substituted hydrocarbyl, F, Cl, Br, silyl, hydroxy, methoxy, nitro, cyano, phenylsulfonyl, $CO_2Me$, $CO_2H$, $C(O)CH_3$, $CF_3$, or fluoroalkyl substituents, (iii) an 9-anthracenyl or 1,2,3,4,5, 6,7,8-octahydro-9-anthracenyl ring, optionally substituted elsewhere with hydrocarbyl, substituted hydrocarbyl, F, Cl, Br, silyl, hydroxy, methoxy, nitro, cyano, phenylsulfonyl, $CO_2Me$, $CO_2H$, $C(O)CH_3$, $CF_3$, or fluoroalkyl substituents, or (iv) an aromatic substituted hydrocarbyl with steric properties functionally equivalent (in the context of this invention) to one or more of the following sterically hindered aryls; 2,6-dimethylphenyl, 2,4,6-trimethylphenyl, 2,6-diisopropylphenyl, 2,6-dimethyl-4-nitrophenyl, 2,6-dimethyl4-phenylsulfonylphenyl, 2-isopropyl-6-methylphenyl, 2,6-bis(trifluoromethyl)phenyl, 2,6-dimethyl-4-methoxyphenyl, 2-methyl napth-1-yl, 9-anthracenyl, 1,2,3,4,5,6,7,8-octahydro-9-anthracenyl, 2,6-diclorophenyl, 2,6-dibromophenyl, 2-tert-butyl-6-methylphenyl, 2-trimethylsilylnapth-1-yl, 2-chloro-6-methylphenyl, 4-cyano-2,6-dimethylphenyl, 2,6-diisopropyl-4-methoxyphenyl, 2,4,6-tri-tert-butylphenyl, and 2-chloro-6-tert-butylphenyl.

A "heteroatom connected mono-radical" refers to a monoradical group in which a heteroatom serves as the point of attachment. Examples include: NH(2,6-dimethylphenyl) and SPh, where Ph is phenyl. Numerous other examples are given herein.

A "substituted silicon atom" refers to a —SiR$^9{}_2$—group, wherein R$^9$ is a hydrocarbyl or substituted hydrocarbyl.

A "substituted phosphorous atom" refers to a —P(O)(OR$^9$)—group, wherein R$^9$ is a hydrocarbyl or substituted hydrocarbyl.

A "substituted sulfur atom" refers to a —S(O)—, —SO$_2$—, or —S(NR$^9$)$_2$—group, wherein R$^9$ is a hydrocarbyl or substituted hydrocarbyl.

A "bridging group" refers to a divalent hydrocarbyl, divalent substituted hydrocarbyl, —C(O)—, —C(S)—, substituted silicon atom, substituted sulfur atom, substituted phosphorous atom, —CH$_2$C(O)—, —C(O)C(O)—, or 3,4,5,6-tetrafluoro-1,2-phenylene.

In certain cases, the bridging group, together with groups A and B, may collectively form a divalent heteroatom substituted heterocycle; examples include:

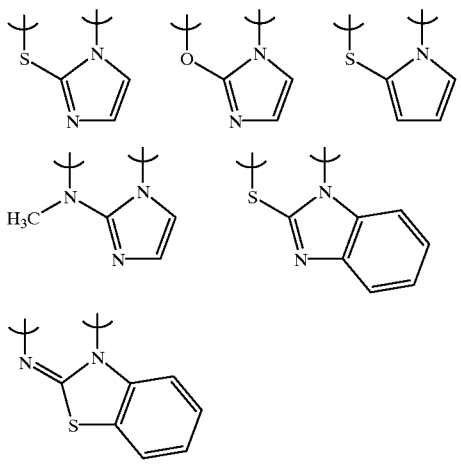

A "mono-olefin" refers to a hydrocarbon containing one carbon-carbon double bond.

A "suitable metal precursor" refers to a Group 8–10 transition metal compound, preferably Ni, Co, Pd, and Fe compounds, which may be combined with compound X (preferably, compound III, VI, IX, XVII or XVIII, described below), and optionally a Lewis or Bronsted acid, to form an active olefin polymerization catalyst. Examples include: (1,2-dimethoxyethane)nickel(II) dibromide, bis[($\mu$-chloro)(1,2,3-$\eta^3$-2-propenyl)nickel(II)], bis[($\mu$-chloro)(1,2,3-$\eta^3$-2-propenyl)palladium(II)], bis[($\mu$-chloro)(1,2,3-$\eta^3$-1-trimethylsilyloxy-2-propenyl)nickel(II)], CoBr$_2$, FeBr$_2$, bis(acetylacetonate)Ni(II), and [tetrakis(acetonitrile)Pd(II)][BF$_4$].

A "suitable nickel precursor" refers to a suitable metal precursor wherein the metal is nickel.

A "suitable nickel(0) precursor" refers to a suitable metal precursor which is a zerovalent nickel compound.

The term "fluoroalkyl" as used herein refers to a C$_1$–C$_{20}$ alkyl group substituted by one or more fluorine atoms.

The term "polymer" as used herein is meant a species comprised of monomer units and having a degree of polymerization (DP) of ten or higher.

The term "$\alpha$-olefin" as used herein is a 1-alkene with from 3 to 40 carbon atoms.

A "$\pi$-allyl" group refers to a monoanionic group with three sp$^2$ carbon atoms bound to a metal center in a $\eta^3$-fashion. Any of the three sp$^2$ carbon atoms may be substituted with a hydrocarbyl, substituted hydrocarbyl, heteroatom connected hydrocarbyl, heteroatom connected substituted hydrocarbyl, or O-silyl group. Examples of $\pi$-allyl groups include:

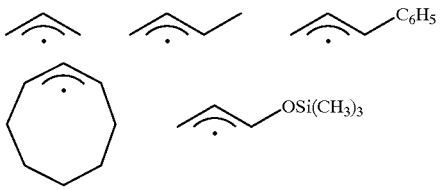

The term $\pi$-benzyl group denotes an $\pi$-allyl group where two of the sp$^2$ carbon atoms are part of an aromatic ring. Examples of $\pi$-benzyl groups include:

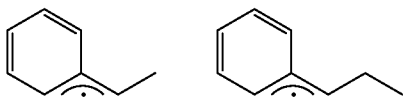

A polymer with a "broad composition distribution" refers to a polymer that comprises a plurality of compositions (preferably >5) having varying levels of branching. The polymers can be fractionated and the fractions have levels of branching/1000 carbons that range from about 0 to about 100 branches/1000 carbons.

A "free flowing polymer" refers to a non-tacky polymer that can be transported without significant agglomeration. In this context, this lack of significant agglomeration refers to polymer products which are useful under commercial gas phase reactor conditions.

As used herein, the terms "monomer" and "olefin monomer" refer to the olefin or other monomer compound before it has been polymerized; the term "monomer units" refers to the moieties of a polymer that correspond to the monomers after they have been polymerized.

In some cases, a compound Y is required as a cocatalyst. Suitable compounds Y include a neutral Lewis acid capable of abstracting Q$^-$ or W$^-$ to form a weakly coordinating anion, a cationic Lewis acid whose counterion is a weakly coordinating anion, or a Bronsted acid whose conjugate base is a weakly coordinating anion. Preferred compounds Y include: methylaluminoxane (hereinafter MAO) and other aluminum sesquioxides. R$^7{}_3$Al, R$^7{}_2$AlCl, R$^7$AlCl$_2$ (wherein R$^7$ is alkyl), organoboron compounds, boron halides, B(C$_6$F$_5$)$_3$, R$^9{}_3$Sn[BF$_4$] (wherein R$^9$ hydrocarbyl), MgCl$_2$, and H$^+$X$^-$, wherein X$^-$ is a weakly coordinating anion. Examples of H$^+$X$^-$ are the ether solvate of hydrogen tetrakis[3,5-bis(trifluoromethyl)phenyl]borate and montmorillinite clay.

Examples of "solid support" include inorganic oxide support materials, such as: talcs, silicas, titania, silica/chromia, silica/chromia/titania, silica/alumina, zirconia, aluminum phosphate gels, silanized silica, silica hydrogels, silica xerogels, silica aerogels, montmorillonite clay and silica co-gels as well as organic solid supports such as polystyrene and functionalized polystyrene. (See, for example, Roscoe, S. B.; Frechet, J. M. J.; Walzer, J. F.; Dias, A. J.; "Polyolefin Spheres from Metallocenes Supported on Non-Interacting Polystyrene", 1998, Science, 280, 270–273 (1998).) An especially preferred solid support is one which has been pre-treated with Y compounds as described herein, most preferably with MAO. Thus, in a preferred embodiment, the catalysts of the present invention are attached to a solid support (by "attached to a solid support" is meant ion paired with a component on the surface, adsorbed to the surface or covalently attached to the surface) which has been pretreated with a compound Y. Alternatively, the catalyst, the compound Y, and the solid support can be combined in any order, and any number of Y compounds can be utilized; in addition, the supported catalyst thus formed, may be treated with additional quantities of compound(s) Y. In an especially preferred embodiment, the compounds of the present invention are attached to silica which has been pre-treated with MAO. Such supported catalysts are prepared by contacting the transition metal compound, in a substantially inert solvent—by which is meant a solvent which is either unreactive under the conditions of catalyst preparation, or if reactive, acts to usefully modify the catalyst activity or selectivity—with MAO treated silica for a sufficient period of time to generate the supported catalysts. Examples of substantially inert solvents include toluene, mineral spirits, hexane. $CH_2Cl_2$ and $CHCl_3$.

In one embodiment, the present invention provides a batch or continuous process for the polymerization of olefins, comprising contacting one or more monomers selected from compounds of the formula $RCH=CHR^8$ with a catalyst comprising (a) a suitable metal precursor and (b) a ligand of the formula X, and optionally (c) a Bronsted or Lewis acid,

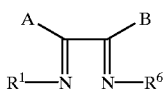

X wherein R and $R^8$ each, independently, represent a hydrogen, a hydrocarbyl, or a fluoroalkyl, and may be linked to form a cyclic olefin;

$R^1$ and $R^6$ are each, independently, hydrocarbyl, substituted hydrocarbyl, or silyl, preferably sterically hindered aryl; N represents nitrogen;

A and B are each, independently, a heteroatom connected mono-radical wherein the connected heteroatom is selected from Group 15 or 16; in addition, A and B may be linked by a bridging group.

In a further aspect of the invention, there is provided a composition comprising (a) a Group 8–10 transition metal M, (b) one or more Lewis acids, and (c) a binucleating or multinucleating compound of the formula X:

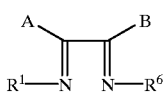

X wherein the Lewis acid or acids are bound to one or more heteroatoms which are π-conjugated to the donor atom or atoms bound to the transition metal M;

$R^1$ and $R^6$ are each, independently, hydrocarbyl, substituted hydrocarbyl, or silyl, preferably sterically hindered aryl;

N represents nitrogen;

A and B are each, independently, a heteroatom connected mono-radical wherein the connected heteroatom is selected from Group 15 or 16; in addition, A and B may be linked by a bridging group.

Preferred Group 8–10 transition metals are Ni, Pd, Fe, and Co, more preferably Ni and Pd.

Preferred ligands X are those given below:

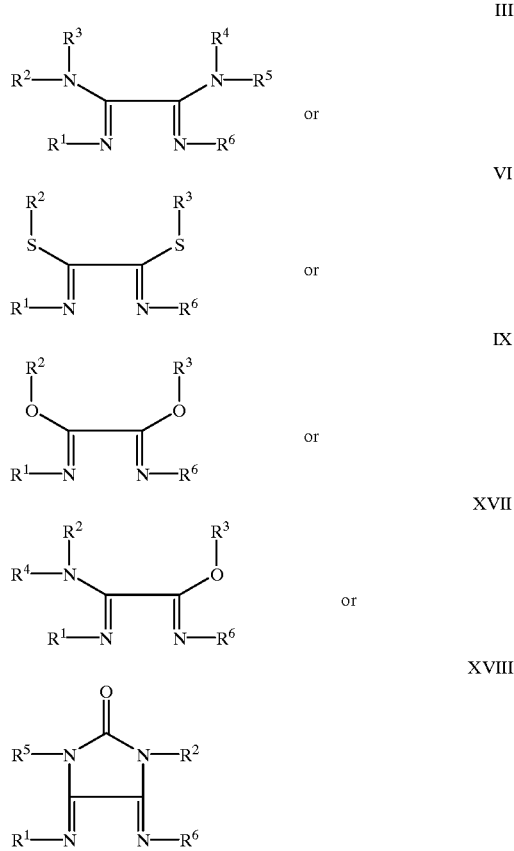

wherein $R^1$ and $R^6$ are as defined above;

$R^2$, $R^3$, $R^4$ and $R^5$ each, independently, represent a hydrogen, hydrocarbyl, substituted hydrocarbyl, or silyl; in addition, any two of $R^2$, $R^3$, $R^4$, or $R^5$ may collectively form a bridging group, provided that when the ligand is of formula VI or IX, the bridging group is not a substituted sulfur atom or a substituted phosphorous atom;

Synthesis of ligands of the formula X in general is based on a modification of methods previously described, and is detailed in the examples given below.

The Group 8–10 transition metal complex having coordinated thereto the bidentate ligand of formula X, above, may also have coordinated to it one or more additional ligands depending, for example, on whether the complex is the active catalyst, a precursor thereto, or the resting state of the catalyst.

In a preferred embodiment of the process of the present invention, one or more olefin monomers of the aforementioned formula LI is contacted with (i) a suitable nickel(0) precursor, preferably bis(1,5-cyclooctadiene)nickel(0);

(ii) a Bronsted acid whose conjugate base is a weakly coordinating anion; and (iii) a compound of the aforementioned formula X, preferably a compound of the formula III, VI, IX, XVII, or XVIII, described above; and polymerization is carried out to obtain a polymer comprising units of the aforementioned olefin monomer.

In another preferred embodiment of the process of the invention, there is provided a batch or continuous process for the polymerization of olefins, comprising contacting one or more monomers of the formula $RCH=CHR^8$ with a catalyst of formula XI:

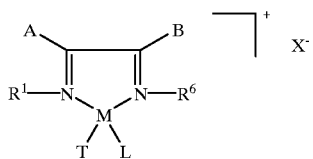

XI wherein R and $R^8$ each, independently, represent a hydrogen, a hydrocarbyl, or a fluoroalkyl, and may be linked to form a cyclic olefin;

$R^1$ and $R^6$ each, independently, represent hydrocarbyl, substituted hydrocarbyl, or silyl, preferably sterically hindered aryl;

A and B are each, independently, a heteroatom connected mono-radical wherein the connected heteroatom is selected from Group 15 or 16; in addition, A and B may be linked by a bridging group;

T represents a hydrogen or a hydrocarbyl;

L represents a mono-olefin or a neutral Lewis base wherein the coordinated atom is nitrogen, oxygen, or sulfur;

M represents Ni(II), Pd(II), Co(II), or Fe(II), preferably Ni(II) or Pd(II);

N represents nitrogen; and

X⁻ is a weakly coordinating anion.

In a preferred embodiment, compound XI is selected from compounds having the following formulas:

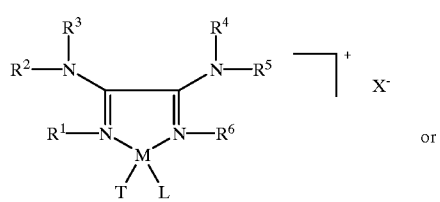

I

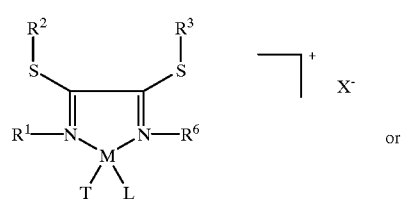

IV

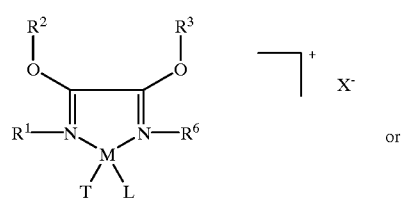

VII

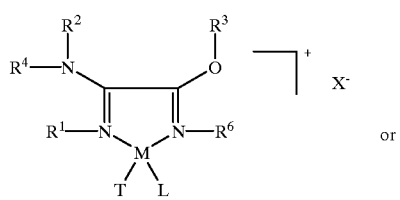

XIII

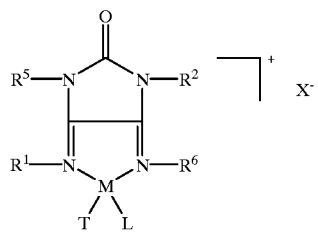

XIV wherein $R^1$, $R^2$, $R^3$, $R^4$, $R^5$, $R^6$, T, L, and M are as defined above.

It is understood that, in the above formulas, when T represents the growing polymer chain or hydrogen, and L is a mono-olefin, the formulas represent the chain propagating species. T and L may collectively represent a π-allyl or π-benzyl complex, represented by the symbol G in the formula below, which is coordinated to M. Thus, in still another preferred embodiment of the process of the present invention, at least one olefin monomer LI is contacted with a catalyst selected from the following formulas:

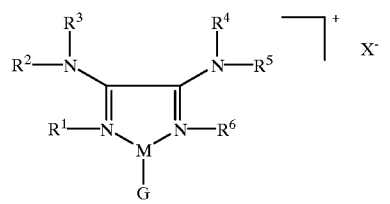

XIX

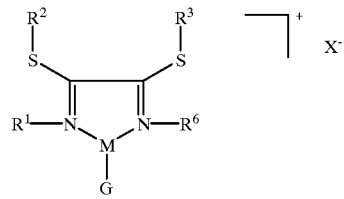

XX

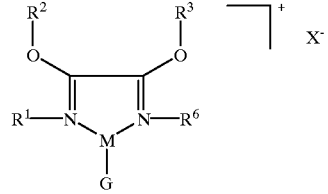

XXI

-continued

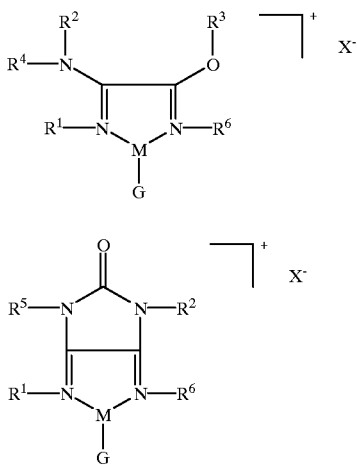

XXII

XXIII wherein $R^1$–$R^6$, and $X^-$ are as defined above;

G is a π-allyl or π-benzyl group,

M is a Group 8–10 transition metal, preferably Pd(II), Ni(II), Fe(II), or Co(II) more preferably Ni(II) or Pd(II);

and polymerization is carried out to obtain a polymer comprising units of the aforementioned olefin monomer.

As a further embodiment of the invention, there is provided a batch or continuous process for the polymerization of olefins, comprising contacting one or more monomers of the formula $RCH=CHR^8$ with a catalyst formed by combining a compound of formula XII:

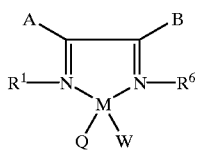

XII with a compound Y, wherein R and $R^8$ each, independently, represent a hydrogen, a hydrocarbyl, or a fluoroalkyl, and may be linked to form a cyclic olefin;

$R^1$ and $R^6$ each, independently, represent hydrocarbyl, substituted hydrocarbyl, or silyl, preferably sterically hindered aryl;

A and B are each, independently, a heteroatom connected mono-radical wherein the connected heteroatom is selected from Group 15 or 16, in addition, A and B may be linked by a bridging group;

Q represents an alkyl, chloride, iodide or bromide;

W represents an alkyl, chloride, iodide or bromide;

N represents nitrogen;

M represents Ni(II), Pd(II), Co(II), or Fe(II), preferably Ni(II) or Pd(II);

and Y is selected from the group consisting of a neutral Lewis acid capable of abstracting $Q^-$ or $W^-$ to form a weakly coordinating anion, a cationic Lewis acid whose counterion is a weakly coordinating anion, and a Bronsted acid whose conjugate base is a weakly coordinating anion.

In a further preferred embodiment, the compound of formula XII is attached to a solid support which has been pre-treated with a compound Y. Thus, as a further aspect of the invention, there is provided a process for the polymerization of olefins, comprising contacting one or more monomers of the formula $RCH=CHR^8$ with a supported catalyst formed by combining a compound of formula XII:

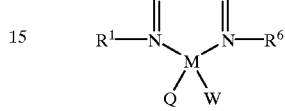

XII with a solid support which has been pre-treated with a compound Y, wherein R and $R^8$ each, independently, represent a hydrogen, a hydrocarbyl, or a fluoroalkyl, and may be linked to form a cyclic olefin;

$R^1$ and $R^6$ each, independently, represent hydrocarbyl, substituted hydrocarbyl, or silyl;

A and B are each, independently, a heteroatom connected mono-radical wherein the connected heteroatom is selected from Group 15 or 16; in addition, A and B may be linked by a bridging group;

Q represents an alkyl, chloride, iodide or bromide;

W represents an alkyl, chloride, iodide or bromide;

N represents nitrogen;

M represents Ni(II), Pd(II), Co(II), or Fe(II);

and Y is selected from the group consisting of a neutral Lewis acid capable of abstracting $W^-$ or $W^-$ to form a weakly coordinating anion, a cationic Lewis acid whose counterion is a weakly coordinating anion, and a Bronsted acid whose conjugate base is a weakly coordinating anion.

In a more preferred embodiment, compounds of formula XII are those selected from the following formulas:

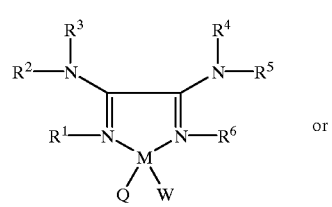

II or

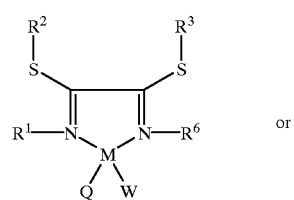

V or

-continued

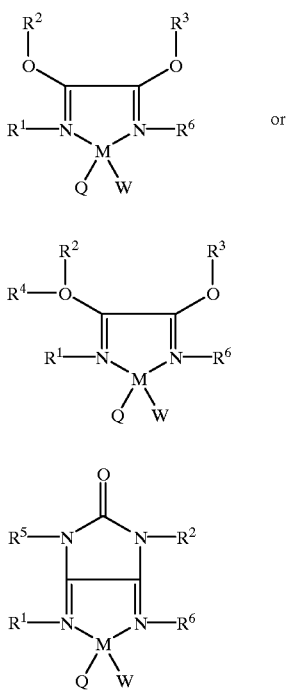

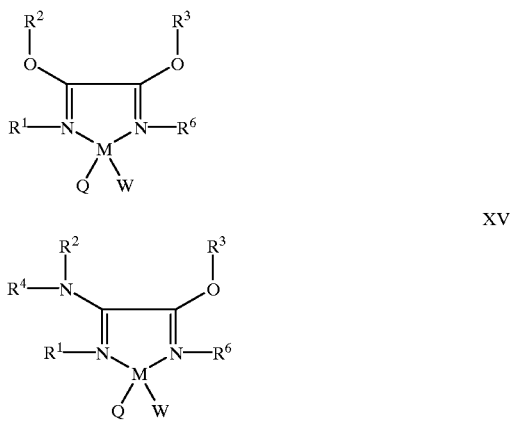

wherein $R^1$ and $R^6$ each, independently, represent hydrocarbyl, substituted hydrocarbyl, or silyl, preferably sterically hindered aryl;

$R^2$, $R^3$, $R^4$ and $R^5$ each, independently, represent a hydrogen, hydrocarbyl, substituted hydrocarbyl, or silyl; in addition, any two of $R^2$, $R^3$, $R^4$, and $R^5$ may be linked by a bridging group, provided that when the compound is of formula V or VIII, the bridging group is not a substituted sulfur atom or a substituted phosphorous atom;

Q represents an alkyl, chloride, iodide or bromide;

W represents an alkyl, chloride, iodide or bromide;

M represents Ni(II), Pd(II), Co(II) or Fe(II); and

N represents nitrogen, O represents oxygen; S represents sulfur.

As a further aspect of the invention, the compound of formula XII is a compound of formula V, VIII, or XV. In an especially preferred embodiment, such compounds are attached to a solid support which has been pretreated with a compound Y. Thus, as a further aspect of the invention, there is provided a supported catalyst comprising the reaction product of a compound of formula V, VIII, or XV:

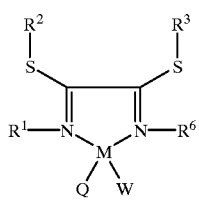

wherein $R^1$ and $R^6$ each, independently represent a sterically hindered aryl;

$R^2$, $R^3$ and $R^4$ each, independently, represent a hydrogen, hydrocarbyl, substituted hydrocarbyl, or silyl, and, in addition any two of $R^2$, $R^3$ and $R^4$ may collectively form a bridging hydrocarbyl, bridging substituted hydrocarbyl, or a substituted silicon atom;

Q represents a hydrocarbyl, chloride, iodide or bromide;

W represents a hydrocarbyl, chloride, iodide or bromide;

N represents nitrogen; and

M represents Ni(II), Pd(II), Co(II), or Fe(II);

with a solid support which has been pre-treated with a compound Y, wherein Y is selected from the group consisting of a neutral Lewis acid capable of abstracting $Q^-$ or $W^-$ to form a weakly coordinating anion, a cationic Lewis acid whose counterion is a weakly coordinating anion, and a Bronsted acid whose conjugate base is a weakly coordinating anion.

Also, as noted herein, the supported catalyst may be prepared by combining the catalyst, the solid support, and any number of compound(s) Y, in any order of addition; further, additional amounts of any number of compounds Y may be added after such preparation. Thus, the present invention provides a process for the preparation of supported catalysts, comprising contacting a compound of formula XII with a solid support which has been pretreated with a compound Y, or wherein said solid support is combined with a compound of formula XII and a compound Y in any sequence,

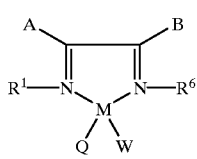

wherein $R^1$ and $R^6$ each, independently, represent hydrocarbyl, substituted hydrocarbyl, or silyl;

A and B are each, independently, a heteroatom connected mono-radical wherein the connected heteroatom is selected from Group 15 or 16; in addition, A and B may be linked by a bridging group;

Q represents an alkyl, chloride, iodide or bromide;

W represents an alkyl, chloride, iodide or bromide;

N represents nitrogen;

M represents Ni(II), Pd(II), Co(II), or Fe(II);

and Y is selected from the group consisting of a neutral Lewis acid capable of abstracting $Q^-$ or $W^-$ to form a weakly coordinating anion, a cationic Lewis acid whose counterion is a weakly coordinating anion, and a Bronsted acid whose conjugate base is a weakly coordinating anion.

Likewise, in a further embodiment, there is provided a process for the polymerization of olefins, comprising contacting one or more monomers of the formula $RCH{=}CHR^8$ with a supported catalyst formed by combining a compound of formula XII:

XII with a solid support which has been pre-treated with a compound Y, or with a supported catalyst formed by combining a compound of formula XII, a solid support, and a compound Y, in any order,

- wherein R and $R^8$ each, independently, represent a hydrogen, a hydrocarbyl, or a fluoroalkyl, and may be linked to form a cyclic olefin;
- $R^1$ and $R^6$ each, independently, represent hydrocarbyl, substituted hydrocarbyl, or silyl;
- A and B are each, independently, a heteroatom connected mono-radical wherein the connected heteroatom is selected from Group 15 or 16; in addition, A and B may be linked by a bridging group;
- Q represents an alkyl, chloride, iodide or bromide;
- W represents an alkyl, chloride, iodide or bromide;
- N represents nitrogen;
- M represents Ni(II), Pd(II), Co(II), or Fe(II);
- and Y is selected from the group consisting of a neutral Lewis acid capable of abstracting $Q^-$ or $W^-$ to form a weakly coordinating anion, a cationic Lewis acid whose counterion is a weakly coordinating anion, and a Bronsted acid whose conjugate base is a weakly coordinating anion.

The present invention also provides a process for the production of α-olefins, comprising contacting ethylene with (a) a suitable nickel precursor, (b) a compound of the formula:

III or

VI or

IX or

XVII or

XVIII and, optionally (c) a Bronsted or Lewis acid, wherein

- $R^1$ and $R^6$ each, independently, represent hydrocarbyl, substituted hydrocarbyl, or silyl, preferably phenyl or 4-methoxyphenyl;
- $R^2$, $R^3$, $R^4$ and $R^5$ each, independently, represent a hydrogen, hydrocarbyl, substituted hydrocarbyl, or silyl; in addition, any two of $R^2$, $R^3$, $R^4$, and $R^5$ may collectively form a bridging group;
- N represents nitrogen; O represents oxygen; S represents sulfur.

As a further preferred aspect, there is provided a process for the production α-olefins, comprising contacting ethylene with a compound of the formula:

I or

IV or

VII or

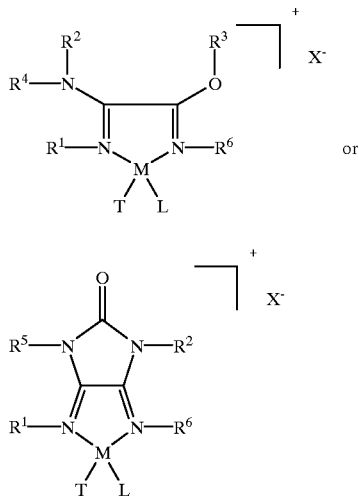

XIII

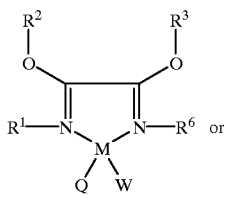

VIII

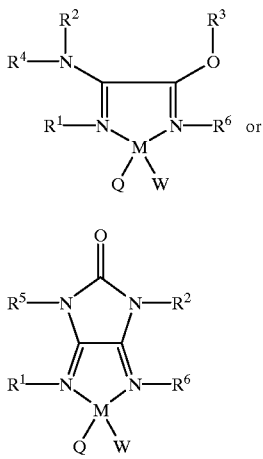

XV

XIV

XVI wherein $R^1$ and $R^6$ each, independently, represent hydrocarbyl, substituted hydrocarbyl, or silyl, preferably phenyl or 4-methoxyphenyl, $R^2$, $R^3$, $R^4$ and $R^5$ each, independently, represent a hydrogen, hydrocarbyl, substituted hydrocarbyl, or silyl; in addition, any two of $R^2$, $R^3$, $R^4$, and $R^5$ may collectively form a bridging group, provided that when the compound is of formula IV or VII, the bridging group is not a substituted sulfur atom or a substituted phosphorous atom;

T represents a hydrogen or hydrocarbyl;

L represents a mono-olefin or a neutral Lewis base wherein the coordinated atom is nitrogen, oxygen, or sulfur;

M represents Ni(II);

N represents nitrogen; O represents oxygen; S represents sulfur; and $X^-$ is a weakly coordinating anion.

As a further preferred aspect, there is provided a process for the production of α-olefins, comprising contacting ethylene with a catalyst formed by combining a complex of the formula:

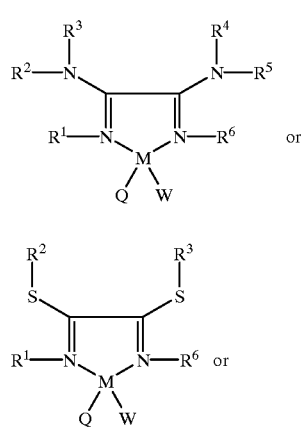

II

V with a compound Y, wherein $R^1$ and $R^6$ each, independently, represent hydrocarbyl, substituted hydrocarbyl, or silyl, preferably phenyl or 4-methoxyphenyl;

$R^2$, $R^3$, $R^4$ and $R^5$ each, independently, represent a hydrogen, hydrocarbyl, substituted hydrocarbyl, or silyl; in addition, any two of $R^2$, $R^3$, $R^4$, and $R^5$ may collectively form bridging group, provided that when the complex is of formula V or VIII, the bridging group is not a substituted sulfur atom or a substituted phosphorous atom;

Q represents a hydrocarbyl, chloride, iodide or bromide;

W represents a hydrocarbyl, chloride, iodide or bromide;

M represents Ni(II);

N represents nitrogen; O represents oxygen; S represents sulfur;

and Y is selected from the group consisting of a neutral Lewis acid capable of abstracting $Q^-$ or $W^-$ to form a weakly coordinating anion, a cationic Lewis acid whose counterion is a weakly coordinating anion, or a Bronsted acid whose conjugate base is a weakly coordinating anion.

A further embodiment of the present invention is a process for the copolymerization of ethylene and a comonomer of the formula $CH_2=CH(CH_2)_nCO_2R^1$ which comprises contacting ethylene and a comonomer of the formula $CH_2=CH(CH_2)_nCO_2R^1$ with the complex formed by combining a first compound Y, which is selected from a neutral Lewis acid capable of abstracting $Q^-$ or $W^-$ to form a weakly coordinating anion, a cationic Lewis acid whose counterion is a weakly coordinating anion, or a Bronsted acid whose conjugate base is a weakly coordinating anion; with a second compound of the formula XXIV:

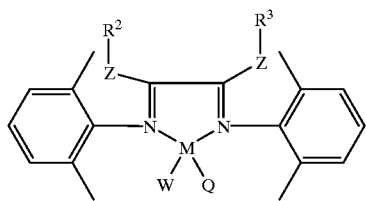

XXIV wherein R¹ is hydrogen, hydrocarbyl, substituted hydrocarbyl, fluoroalkyl or silyl;

n is an integer greater than 3, preferably greater than 5 and less than 25;

R² and R³ are each independently hydrogen, hydrocarbyl, substituted hydrocarbyl, or silyl, or may collectively form a bridging hydrocarbyl, bridging substituted hydrocarbyl, or a substituted silicon atom;

Q is alkyl, chloride, iodide or bromide;

W is alkyl, chloride, iodide or bromide;

N is nitrogen;

Z is sulfur or oxygen; and

M is Ni(II).

It is further preferred that such compounds be attached to a solid support which has been pre-treated with a compound such as MAO or other aluminum sesquioxides. Thus, as a further embodiment, there is provided process for the copolymerization of ethylene and a comonomer of the formula $CH_2=CH(CH_2)_nCO_2R^1$ which comprises contacting ethylene and a comonomer of the formula $CH_2=CH(CH_2)_nCO_2R^1$ with a supported catalyst formed by combining silica with a compound selected from the group consisting of methylaluminoxane and other aluminum sesquioxides having the formulas $R^7_3Al$, $R^7_2AlCl$, and $R^7AlCl_2$, wherein $R^7$ is alkyl;

with a compound of the formula XXIV:

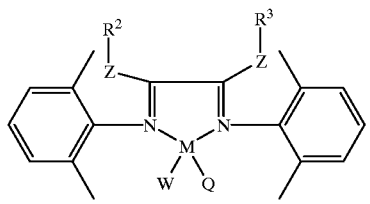

XXIV wherein R¹ is hydrogen, hydrocarbyl, substituted hydrocarbyl, fluoroalkyl or silyl;

n is an integer greater than 3;

R² and R³ are each independently hydrogen, hydrocarbyl, substituted hydrocarbyl, or silyl, or may collectively form a bridging hydrocarbyl, bridging substituted hydrocarbyl, or a substituted silicon atom;

Q is alkyl, chloride, iodide or bromide;

W is alkyl, chloride, iodide or bromide;

N is nitrogen;

Z is sulfur or oxygen; and

M is Ni(II).

As a further aspect of the invention, there is provided a process for the polymerization of ethylene and a comonomer of the formula $CH_2=CH(CH_2)_nCO_2R^1$, which comprises contacting ethylene and a comonomer of the formula $CH_2=CH(CH_2)_nCO_2R^1$ with the complex formed by the reaction product of (a) a compound of formula XLII, (b) a suitable nickel(1) precursor, and (c) a Bronsted acid whose conjugate base is a weakly coordinating anion,

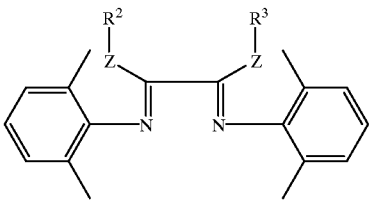

XLII wherein R¹ is hydrogen, hydrocarbyl, substituted hydrocarbyl, fluoroalkyl or silyl;

n is an integer greater than 3, preferably greater than 5 and less than 25;

R² and R³ are each independently hydrogen, hydrocarbyl, substituted hydrocarbyl, or silyl, or may collectively form a bridging hydrocarbyl, bridging substituted hydrocarbyl, —C(O)—, or a substituted silicon atom;

N is nitrogen; and

Z is sulfur or oxygen.

As a further embodiment of the invention, there is provided a process for the polymerization of olefins comprising contacting one or more monomers of the formula $RCH=CHR^8$ with a binucleating or multinucleating ligand complexed to a Group 8–10 transition metal M and one or more Lewis acids, wherein the Lewis acid or acids are bound to one or more heteroatoms which are π-conjugated to the donor atom or atoms bound to the transition metal M; and R and R⁸ each, independently, represent a hydrogen, a hydrocarbyl, or a fluoroalkyl, and may be linked to form a cyclic olefin.

The catalysts of the present invention comprise a Group 8–10 transition metal coordinated by the bidentate ligand X; these include, but are not limited to, the preferred compounds I, II, IV, V, VII, VIII, XI–XVI, XIX–XXVIII, and XXX–XLII, set forth in detail herein.

A more preferred embodiment of the catalyst of the present invention is a compound of the formula I:

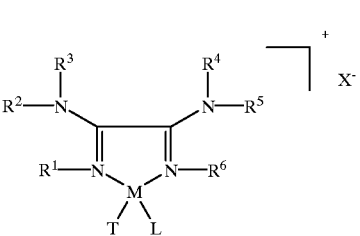

I wherein R¹ and R⁶ each, independently, represent hydrocarbyl, substituted hydrocarbyl, or silyl, preferably phenyl, 4-methoxyphenyl, or sterically hindered aryl;

R², R³, R⁴ and R⁵ each, independently, represent a hydrogen, hydrocarbyl, substituted hydrocarbyl, or silyl; in addition, any two of R², R³, R⁴, and R⁵ may collectively form a bridging group;

T represents a hydrogen or hydrocarbyl;

L represents a mono-olefin or a neutral Lewis base wherein the coordinated atom is nitrogen, oxygen, or sulfur;

M represents a Group 8–10 transition metal, preferably Ni(II), Pd(II), Co(II), or Fe(II), more preferably Ni(II) or Pd(II);

N represents nitrogen; and

X⁻ is a weakly coordinating anion.

Also disclosed is a catalyst comprising a compound of formula II:

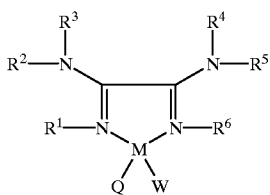

II wherein R¹ and R⁶ each, independently, represent hydrocarbyl, substituted hydrocarbyl, or silyl, preferably phenyl, 4-methoxyphenyl, or sterically hindered aryl;

$R^2$, $R^3$, $R^4$ and $R^5$ each, independently, represent a hydrogen, hydrocarbyl, substituted hydrocarbyl, or silyl; in addition, any two of $R^2$, $R^3$, $R^4$, and $R^5$ may collectively form a bridging group;

Q represents a hydrocarbyl, chloride, iodide or bromide;

W represents a hydrocarbyl, chloride, iodide or bromide;

N represents nitrogen; and

M represents a Group 8–10 transition metal, preferably Ni(II) Pd(II), Co(II), or Fe(II), more preferably Ni(II) or Pd(II).

Also described is a catalyst comprising a compound of formula IV:

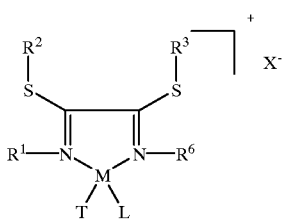

IV wherein R¹ and R⁶ each, independently, represent hydrocarbyl, substituted hydrocarbyl, or silyl, preferably phenyl, 4-methoxyphenyl, or sterically hindered aryl;

R² and R³ each, independently, represent a hydrogen, hydrocarbyl, substituted hydrocarbyl, or silyl, and, in addition, may collectively form a bridging hydrocarbyl, bridging substituted hydrocarbyl, or a substituted silicon atom;

T represents a hydrogen or hydrocarbyl;

L represents a mono-olefin or a neutral Lewis base wherein the coordinated atom is nitrogen, oxygen, or sulfur;

M represents Ni(II), Pd(II), Co(II), or Fe(II), more preferably Ni(II) or Pd(II);

N represents nitrogen; and

X⁻ is a weakly coordinating anion.

Additionally disclosed is a catalyst comprising a compound of formula V:

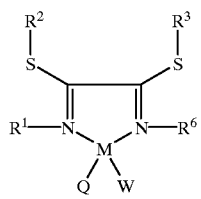

V wherein R¹ and R⁶ each, independently, represent hydrocarbyl, substituted hydrocarbyl or silyl, preferably phenyl, or 4-methoxyphenyl or sterically hindered aryl;

R² and R³ each, independently, represent a hydrogen, hydrocarbyl, substituted hydrocarbyl, or silyl, and, in addition, may collectively form a bridging hydrocarbyl, bridging substituted hydrocarbyl, or a substituted silicon atom;

Q represents a hydrocarbyl, chloride, iodide or bromide;

W represents a hydrocarbyl, chloride, iodide or bromide;

N represents nitrogen; and

M represents a Group 8–10 transition metal, preferably Ni(II), Pd(II), Co(II), or Fe(II) more preferably Ni(II) or Pd(II);

In addition this invention teaches the use of a catalyst comprising a compound of formula VI:

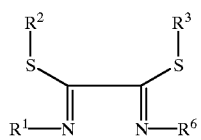

VI wherein R¹ and R⁶ each, independently, represent hydrocarbyl, substituted hydrocarbyl, or silyl, preferably phenyl, 4-methoxyphenyl, or sterically hindered aryl; and R² and R³ each, independently, represent a hydrogen, hydrocarbyl, substituted hydrocarbyl, or silyl, and, in addition, may collectively form a bridging hydrocarbyl, bridging substituted hydrocarbyl, or a substituted silicon atom.

Described herein is a catalyst comprising a compound of the formula VII:

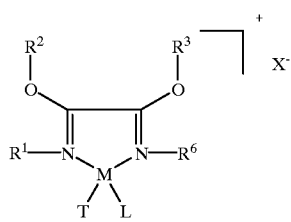

VII wherein R¹ and R⁶ each, independently, represent hydrocarbyl, substituted hydrocarbyl, or silyl, preferably phenyl, 4-methoxyphenyl, or sterically hindered aryl;

R² and R³ each, independently, represent a hydrogen, hydrocarbyl, substituted hydrocarbyl, or silyl, and, in addition, may collectively form a bridging hydrocarbyl, bridging substituted hydrocarbyl, or a substituted silicon atom;

T represents a hydrogen or hydrocarbyl;

L represents a mono-olefin or a neutral Lewis base wherein the coordinated atom is nitrogen, oxygen, or sulfur;

M represents Ni(II), Pd(II), Co(II), or Fe(II), more preferably Ni(II) or Pd(II);

N represents nitrogen; and $X^-$ is a weakly coordinating anion.

Also described herein is a catalyst comprising a compound of formula VIII:

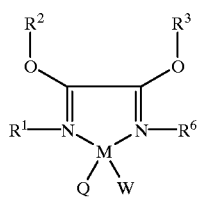

VIII wherein $R^1$ and $R^6$ each, independently, represent hydrocarbyl, substituted hydrocarbyl, or silyl, preferably phenyl, 4-methoxyphenyl, or sterically hindered aryl;

$R^2$ and $R^3$ each, independently, represent a hydrogen, hydrocarbyl, substituted hydrocarbyl, or silyl, and, in addition, may collectively form a bridging hydrocarbyl, bridging substituted hydrocarbyl, or a substituted silicon atom;

Q represents a hydrocarbyl, chloride, iodide or bromide;

W represents a hydrocarbyl, chloride, iodide or bromide;

N represents nitrogen; and

M represents a Group 8–10 transition metal, preferably Ni(II), Pd(II), Co(II), or Fe(II), more preferably Ni(II) or Pd(II).

Also described herein is a catalyst comprising a compound of formula IX:

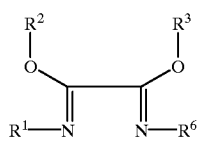

IX wherein $R^1$ and $R^6$ each, independently, represent hydrocarbyl, substituted hydrocarbyl, or silyl, preferably phenyl, 4-methoxyphenyl, or sterically hindered aryl; and $R^2$ and $R^3$ each, independently, represent a hydrogen, hydrocarbyl, substituted hydrocarbyl, or silyl, and, in addition any two of $R^2$, $R^3$ and $R^4$ may collectively form a bridging hydrocarbyl, bridging substituted hydrocarbyl, or a substituted silicon atom.

Also described herein is a catalyst comprising a compound of the formula XIII:

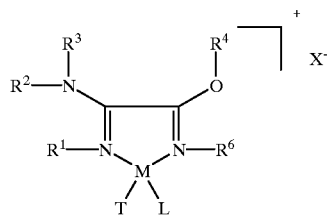

XIII wherein $R^1$ and $R^6$ each, independently, represent hydrocarbyl, substituted hydrocarbyl, or silyl, preferably phenyl, 4-methoxyphenyl, or sterically hindered aryl;

$R^2$, $R^3$, and $R^4$ each, independently, represent a hydrogen, hydrocarbyl, substituted hydrocarbyl, or silyl, and, in addition any two of $R^2$, $R^3$ and $R^4$ may collectively form a bridging group;

T represents a hydrogen or hydrocarbyl;

L represents a mono-olefin or a neutral Lewis base wherein the coordinated atom is nitrogen, oxygen, or sulfur;

M represents Ni(II), Pd(II), Co(II), or Fe(II), more preferably Ni(II) or Pd(II);

N represents nitrogen; and $X^-$ is a weakly coordinating anion.

Also provided herein is a catalyst comprising a compound of the formula XIV:

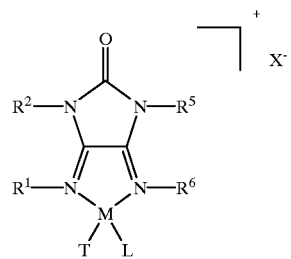

XIV wherein $R^1$ and $R^6$ each, independently, represent hydrocarbyl, substituted hydrocarbyl, or silyl, preferably phenyl, 4-methoxyphenyl, or sterically hindered aryl;

$R^2$ and $R^5$ each, independently, represent a hydrogen hydrocarbyl, substituted hydrocarbyl, or silyl;

T represents a hydrogen or hydrocarbyl;

L represents a mono-olefin or a neutral Lewis base wherein the coordinated atom is nitrogen, oxygen, or sulfur;

M represents a Group 8–10 transition metal, preferably Ni(II), Pd(II), Co(II), or Fe(II) more preferably Ni(II) or Pd(II);

N represents nitrogen; and $X^-$ is a weakly coordinating anion.

Also provided herein is a catalyst comprising a compound of formula XV:

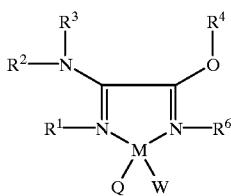

XV wherein $R^1$ and $R^6$ each, independently, represent hydrocarbyl, substituted hydrocarbyl, or silyl, preferably phenyl, 4-methoxyphenyl, or sterically hindered aryl;

$R^2$, $R^3$, and $R^4$ each, independently, represent a hydrogen, hydrocarbyl, substituted hydrocarbyl, or silyl, and, in addition any two of $R^2$, $R^3$ and $R^4$ may collectively form a bridging group;

Q represents a hydrocarbyl, chloride, iodide or bromide;

W represents a hydrocarbyl, chloride, iodide or bromide;

N represents nitrogen; and

M represents a Group 8–10 transition metal, preferably Ni(II), Pd(II), Co(II), or Fe(II), preferably Ni(II) or Pd(II).

Also described herein is a catalyst comprising a compound of formula XVII

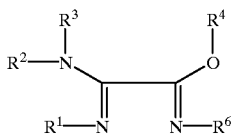

XVII wherein $R^1$ and $R^6$ each, independently, represent hydrocarbyl, substituted hydrocarbyl, or silyl, preferably phenyl, 4-methoxyphenyl, or sterically hindered aryl; and $R^2$, $R^3$, and $R^4$ each, independently, represent a hydrogen, hydrocarbyl, substituted hydrocarbyl, or silyl; in addition, any two of $R^2$, $R^3$, or $R^4$ may collectively form a bridging group.

Also provided herein is a catalyst comprising a compound of formula XVI:

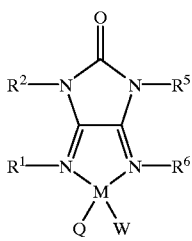

XVI wherein $R^1$ and $R^6$ each, independently, represent hydrocarbyl, substituted hydrocarbyl, or silyl, preferably phenyl, 4-methoxyphenyl, or sterically hindered aryl;

$R^2$ and $R^5$ each, independently, represent a hydrogen, hydrocarbyl, substituted hydrocarbyl, or silyl, preferably sterically hindered aryl;

Q represents a hydrocarbyl, chloride, iodide or bromide;

W represents a hydrocarbyl, chloride, iodide or bromide;

N represents nitrogen; and

M represents a Group 8–10 transition metal, preferably Ni(II), Pd(II), Co(II), or Fe(II), more preferably Ni(II) or Pd(II);

Also provided herein is a catalyst comprising a compound of formula XVIII:

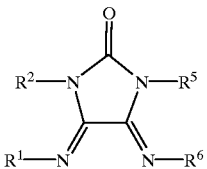

XVIII wherein $R^1$ and $R^6$ each, independently, represent hydrocarbyl, substituted hydrocarbyl, or silyl, preferably phenyl, 4-methoxyphenyl, or sterically hindered aryl;

$R^2$ and $R^5$ each, independently, represent a hydrogen, hydrocarbyl, substituted hydrocarbyl, or silyl.

Also provided herein is a catalyst comprising a compound of the formula XIX:

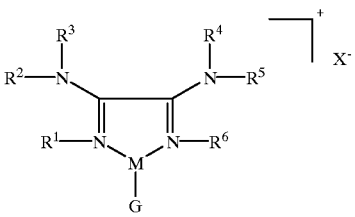

XIX wherein $R^1$ and $R^6$ each, independently, represent hydrocarbyl, substituted hydrocarbyl, or silyl, preferably phenyl. 4-methoxyphenyl, or sterically hindered aryl;

$R^2$, $R^3$, $R^4$ and $R^5$ each, independently, represent a hydrogen, hydrocarbyl, substituted hydrocarbyl, or silyl; in addition, any two of $R^2$, $R^3$, $R^4$, and $R^5$ may collectively form a bridging group;

G is a π-allyl or π-benzyl group;

M represents Ni(II) or Pd(II);

N represents nitrogen; and $X^-$ is a weakly coordinating anion.

Also provided herein is a catalyst comprising a compound of formula XX:

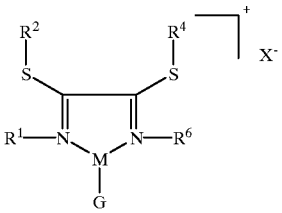

XX wherein $R^1$ and $R^6$ each, independently, represent hydrocarbyl, substituted hydrocarbyl, or silyl, preferably phenyl, 4-methoxyphenyl, or sterically hindered aryl;

$R^2$ and $R^3$ each, independently, represent a hydrogen, hydrocarbyl, substituted hydrocarbyl, or silyl, and, in addition, may collectively form a bridging hydrocarbyl, bridging substituted hydrocarbyl, or a substituted silicon atom;

G is a π-allyl or π-benzyl;

M represents Ni(II) or Pd(II);

N represents nitrogen; and $X^-$ is a weakly coordinating anion.

Also provided herein is a catalyst comprising a compound of the formula XXI:

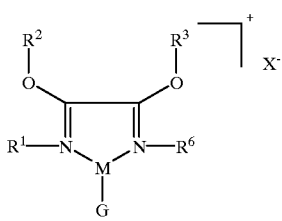

XXI wherein $R^1$ and $R^6$ each, independently, represent hydrocarbyl, substituted hydrocarbyl, or silyl, preferably phenyl, 4-methoxyphenyl, or sterically hindered aryl;

$R^2$ and $R^3$ each, independently, represent a hydrogen, hydrocarbyl, substituted hydrocarbyl, or silyl, and, in addition, may collectively form a bridging hydrocarbyl, bridging substituted hydrocarbyl, or a substituted silicon atom;

G is a π-allyl or π-benzyl;

M represents Ni(II) or Pd(II);

N represents nitrogen; and $X^-$ is a weakly coordinating anion.

Also provided herein is a catalyst comprising a compound of the formula XXII:

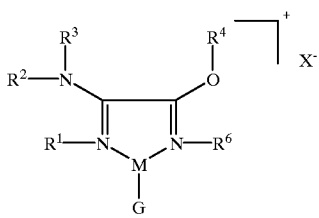

XXII wherein $R^1$ and $R^6$ each, independently, represent hydrocarbyl, substituted hydrocarbyl, or silyl, preferably phenyl, 4-methoxyphenyl, or sterically hindered aryl;

$R^2$, $R^3$, and $R^4$ each, independently, represent a hydrogen, hydrocarbyl, substituted hydrocarbyl, or silyl; in addition, any two of $R^2$, $R^3$, and $R^4$ may collectively form a bridging group;

G is a π-allyl or π-benzyl;

M represents Ni(II) or Pd(II);

N represents nitrogen; and $X^-$ is a weakly coordinating anion.

Also provided herein is a catalyst comprising a compound of the formula XXIII:

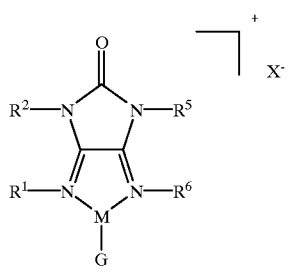

XXIII wherein $R^1$ and $R^6$ each, independently, represent hydrocarbyl, substituted hydrocarbyl, or silyl, preferably phenyl, 4-methoxyphenyl, or sterically hindered aryl;

$R^2$ and $R^5$ each, independently, represent a hydrogen, hydrocarbyl, substituted hydrocarbyl, or silyl;

G is a π-allyl or π-benzyl;

M represents Ni(II) or Pd(II);

N represents nitrogen; and $X^-$ is a weakly coordinating anion.

Also provided is a compound of formula XXIV,

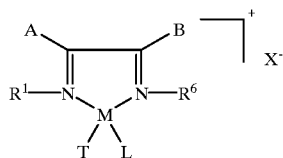

XXIV wherein $R^1$ and $R^6$ each, independently, represent hydrocarbyl, substituted hydrocarbyl, or silyl, preferably phenyl, 4-methoxyphenyl, or sterically hindered aryl;

A and B are each, independently, a heteroatom connected mono-radical wherein the connected heteroatom is selected from Group 15 or 16; in addition, A and B may be linked by a bridging group;

T represents a hydrogen or a hydrocarbyl;

L represents a mono-olefin or a neutral Lewis base wherein the coordinated atom is nitrogen, oxygen, or sulfur;

M represents Ni(II) or Pd(II);

N represents nitrogen; and $X^-$ is a weakly coordinating anion.

Also provided herein is a catalyst for the polymerization of olefins, comprising a compound of formula XXV,

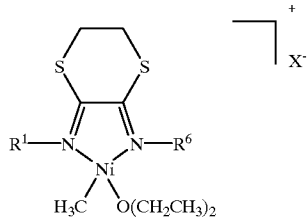

XXV wherein $R^1$ and $R^6$ are 2,6-dimethylphenyl; and $X^-$ is a weakly coordinating anion.

Also provided herein is a catalyst for the polymerization of olefins, comprising a compound of formula XXVI,

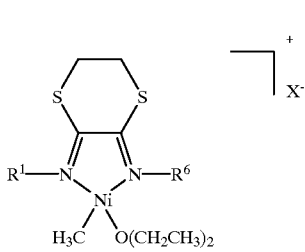

XXVI wherein $R^1$ and $R^6$ are 2,6-diisopropylphenyl; and $X^-$ is a weakly coordinating anion.

Also provided herein is a catalyst for the polymerization of olefins, comprising a compound of formula XXVII,

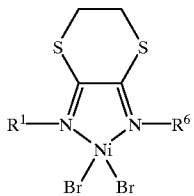

XXVII wherein $R^1$ and $R^6$ are 2,6-dimethylphenyl.

Also provided herein is a catalyst for the polymerization of olefins, comprising a compound of formula XXVIII,

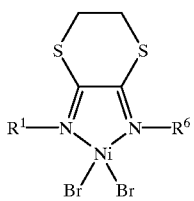

XXVIII wherein $R^1$ and $R^6$ are 2,6-diisopropylphenyl.

Also provided herein is a catalyst comprising a compound of formula XXIX,

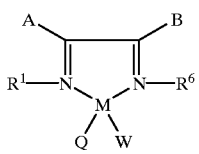

XXIX wherein $R^1$ and $R^6$ each, independently, represent hydrocarbyl, substituted hydrocarbyl, or silyl, preferably phenyl, 4-methoxyphenyl, or sterically hindered aryl;

A and B are each, independently, a heteroatom connected mono-radical wherein the connected heteroatom is selected from Group 15 or 16; in addition, A and B may be linked by a bridging group;

Q represents a hydrocarbyl, chloride, iodide or bromide;
W represents a hydrocarbyl, chloride, iodide or bromide;
M represents Ni(II) or Pd(II); and N represents nitrogen.

Also provided herein is a catalyst for the polymerization of olefins comprising a compound of formula XXX,

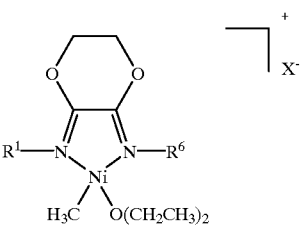

XXX wherein $R^1$ and $R^6$ are 2,6-dimethylphenyl; and $X^-$ is a weakly coordinating anion.

Also provided herein is a catalyst for the polymerization of olefins, comprising a compound of formula XXXI,

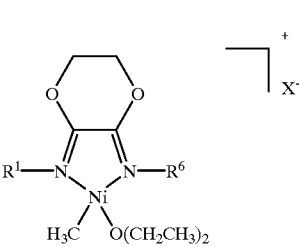

XXXI wherein $R^1$ and $R^6$ are 2,6-diisopropylphenyl; and $X^-$ is a weakly coordinating anion.

Also provided herein is a catalyst for the polymerization of olefins, comprising a compound of formula XXXII,

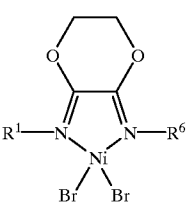

XXXII wherein $R^1$ and $R^6$ are 2,6-dimethylphenyl.

Also provided herein is a catalyst for the polymerization of olefins, comprising a compound of formula XXXIII,

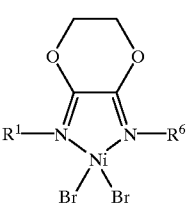

XXXIII wherein $R^1$ and $R^6$ are 2,6-diisopropylphenyl.

Also provided herein is a catalyst for the polymerization of olefins, comprising a compound of formula XXXIV,

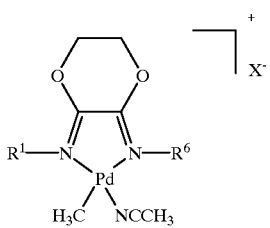

wherein $R^1$ and $R^6$ are 2,6-diisopropylphenyl;
and $X^-$ is a weakly coordinating anion.
Also provided herein is a catalyst for the polymerization of olefins, comprising a compound of formula XXXV,

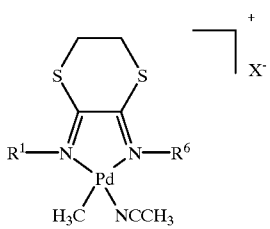

wherein $R^1$ and $R^6$ are 2,6-diisopropylphenyl;
and X is a weakly coordinating anion.
Also provided herein is a catalyst for the polymerization of olefins, comprising a compound of formula XXXVI,

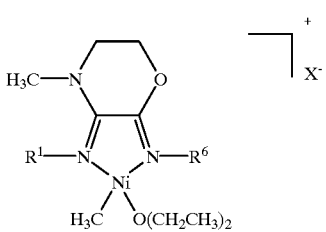

wherein $R^1$ and $R^6$ are 2,6-dimethylphenyl;
and $X^-$ is a weakly coordinating anion.
Also provided herein is a catalyst for the polymerization of olefins, comprising a compound of formula XXXVII,

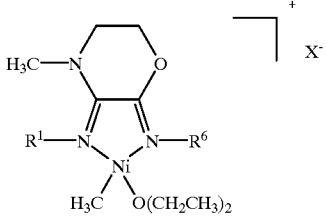

wherein $R^1$ and $R^6$ are 2,6-diisopropylphenyl;
and $X^-$ is a weakly coordinating anion.
Also provided herein is a catalyst for the polymerization of olefins, comprising a compound of formula XXXVIII,

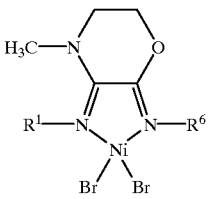

wherein $R^1$ and $R^6$ are 2,6-dimethylphenyl.
Also provided herein is a catalyst for the polymerization of olefins, comprising a compound of formula XXXIX,

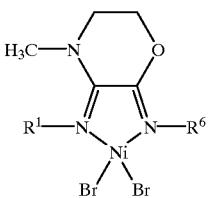

wherein $R^1$ and $R^6$ are 2,6-diisopropylphenyl.
Also provided herein is a catalyst for the polymerization of olefins, comprising a compound of formula XL,

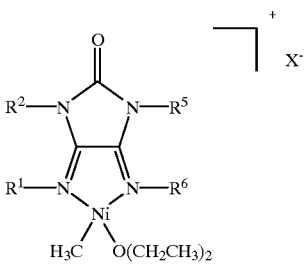

wherein $R^1$, $R^2$, $R^5$ and $R^6$ are 2,6-dimethyl-4-methoxyphenyl;
and $X^-$ is a weakly coordinating anion.
Also provided herein is a catalyst for the polymerization of olefins, comprising a compound of formula XLI,

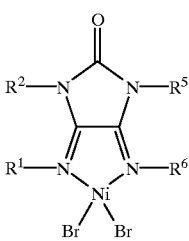

wherein $R^1$, $R^2$, $R^5$ and $R^6$ are 2,6-dimethyl-4-methoxyphenyl;
and $X^-$ is a weakly coordinating anion.
The invention also provides certain novel polymer compositions. Thus, as a further aspect of the invention, there is provided a polymer composition comprised of monomer units derived from ethylene and from 0.1 to 50 wt % of a comonomer of the formula $CH_2=CH(CH_2)_nCO_2R^1$, wherein $R^1$ is hydrogen, hydrocarbyl, substituted hydrocarbyl, fluoroalkyl or silyl, and n is an integer between 3 and 18; in addition to the branches attributable to the incorporation of said comonomer, alkyl branches are present in said polymer composition, wherein between 5 and 50 alkyl branches per 1000 carbon atoms are present and the majority of alkyl branches are methyl branches.

In a preferred embodiment, there is provided a composition comprising an ester containing semicrystalline copolyethylene with 5 to 30 alkyl branches/1000 carbon atoms, wherein the majority of alkyl branches are methyl branches, and an average of from about 1 to 50 ester terminated branches per chain resulting from ester comonomer incorporation.

In a further preferred embodiment, there is provided a composition comprising an olefin containing semicrystalline copolyethylene with 5 to 30 alkyl branches/1000 carbon atoms, wherein the majority of alkyl branches are methyl branches, and an average of from about 1 to 50 olefin terminated branches per chain resulting from linear diene comonomer incorporation.

As a further aspect of the invention, there is also provided a polymer composition comprising an ethylene homopolymer with greater than 125 alkyl branches per 1000 carbon atoms, useful as an adhesive or tackifying agent.

As noted above, it is preferred that certain of the compounds of the present invention be attached to a solid support which has been pre-treated with a compound Y, for example, MAO, or mixed with Y in any order. We have discovered that when such supported catalysts are used in slurry and gas phase ethylene polymerizations, novel polymer compositions are provided insofar as such compositions are blends of different polyolefin polymers. It is believed that when such catalysts are attached to a solid support, such as silica, polyolefin polymerizations using such supported catalysts provide a polymer composition which possesses a broad compositional distribution. This is believed to be due at least in part to both the creation of unique reaction sites, and the sensitivity of these catalysts to ethylene concentration. These unique reaction sites are believed to result from the unique microenvironments created by the location of the catalyst on the support. The resulting polymer composition, which can be prepared solely from ethylene as an olefin feedstock, is one which is actually a blend or plurality of polymers having a variety of alkyl branched distributions with some catalyst sites giving less branched high density polymer and other sites giving more branched lower density polymer. Thus, as a further aspect of the invention, there is provided a polyethylene composition comprising a blend of polyethylene polymers, wherein said blend has an average degree of branching of from 5 to 120 alkyl branches per 1000 carbon atoms, wherein any individual component of said blend has a degree of branching of from 0 to 150 alkyl branches per 1000 carbon atoms, wherein said polymers are prepared in one reaction vessel solely from ethylene, and wherein said polymers are prepared utilizing a Group 8–10 transition metal catalyst supported on a solid support which has been pre-treated with a compound Y selected from the group consisting of methylaluminoxane and other aluminum sesquioxides having the formulas $R^7_3Al$, $R^7_2AlCl$, and $R^7AlCl_2$, wherein $R^7$ is alkyl.

Further, the catalysts of this invention when supported in this fashion and utilized in a gas or slurry phase process provide polymers having a broad composition distribution while having an intermediate molecular weight distribution, thus providing certain processing advantages. When fractionated based on solubility using supercritical propane by isothermal increasing profiling and critical, isobaric, temperature rising elution fractionation, into ten fractions, an analysis of such fractions provides data on the distribution of the relative branching of the components of said composition. Thus, in a further embodiment, the present invention provides a polyolefin which when fractionated based on solubility using supercritical propane by isothermal increasing profiling and critical, isobaric, temperature rising elution fractionation, into ten fractions between about 40 and about 140° C., wherein a first fraction taken at about 40° C. has between about 40 and about 100 branches per 1000 carbon atoms, wherein between about 50 to about 90% are methyl branches, about 5 to about 15% are ethyl branches, about 1 to about 10% are propyl branches, about 0 to about 15% are butyl branches, and between about 5 and about 15% are pentyl or longer branches, a second fraction taken between about 40–60° C. has between about 30 and about 90 branches per 1000 carbon atoms, wherein between about 50 to about 90% are methyl branches, about 5 to about 15% are ethyl branches, about 1 to about 10% are propyl branches, about 0 to about 15% are butyl branches, and between about 5 and about 15% are pentyl or longer branches; a third fraction taken between about 60–65° C. has between about 30 and about 80 branches per 1000 carbon atoms, wherein between about 50 to about 90% are methyl branches, about 5 to about 15% are ethyl branches, about 1 to about 10% are propyl branches, about 0 to about 15% are butyl branches, and between about 5 to about 15% are pentyl or longer branches; a fourth fraction taken between about 65–70° C. has between about 20 and about 60 branches per 1000 carbon atoms, wherein between about 50 to about 90% are methyl branches, about 5 to about 15% are ethyl branches, about 1 to about 10% are propyl branches, about 0 to about 15% are butyl branches, and between about 5 to about 15% are pentyl or longer branches; a fifth fraction taken between about 75–85° C. has between about 10 and about 50 branches per 1000 carbon atoms, wherein between about 50 to about 90% are methyl branches, about 5 to about 15% are ethyl branches, about 0 to about 10% are propyl branches, about 0 to about 15% are butyl branches, and between about 5 to about 15% are pentyl or longer branches; a sixth fraction taken between about 85–95° C. has between about 10 and about 40 branches per 1000 carbon atoms, wherein between about 50 to about 90% are methyl branches, about 5 to about 15% are ethyl branches, about 0 to about 10% are propyl branches, about 0 to about 15% are butyl branches, and between about 5 and about 15% are pentyl or longer branches; a seventh fraction taken between about 95–100° C. has between about 5 and about 35 branches per 1000 carbon atoms, wherein between about 50 to about 90% are methyl branches, about 5 to about 15% are ethyl branches, about 0 to about 10% are propyl branches, about 0 to about 15% are butyl branches, and between about 0 and about 15% are pentyl or longer branches; an eighth fraction taken between about 100–110° C. has between about 0 and about 25 branches per 1000 carbon atoms, wherein between about 50 to about 90% are methyl branches, about 5 to about 15% are ethyl branches, about 0 to about 10% are propyl branches, about 0 to about 15% are butyl branches, and between about 0 and about 15% are pentyl or longer branches; a ninth fraction taken between about 110–140° C. has between about 0 and about 30 branches per 1000 carbon atoms, wherein between about 50 to about 90% are methyl branches, about 5 to about 15% are ethyl branches, about 0 to about 10% are propyl branches, about 0 to about 15% are butyl branches, and between about 0 to about 15% are pentyl or longer branches; a tenth fraction taken between about 140–150° C. has between about 0 and about 20 branches per 1000 carbon atoms, wherein between about 50 to about 90% are methyl branches, about 5 to about 15% are ethyl branches, about 0 to about 10% are propyl branches, about 0 to about 15% are butyl branches, and between about 0 to about 15% are pentyl or longer branches; and a tenth fraction has between about 0 and about 20 branches per 1000 carbon atoms. (See also the Examples below).

Further, in contrast to a polymer prepared by solution polymerization, where the melting temperature as defined by the endothermic maximum is inversely correllated with the average degree of branching of said polymer, the polymers prepared from such supported catalysts exhibit a relatively constant melting temperature (endothermic maximum) over a relatively wide range of average branching. In certain cases, this also provides a free flowing powder which is again, a significant processing advantage in the gas phase.

Thus, the present invention provides a polymer derived from essentially ethylene alone that has greater than 30 branches per 1000 carbon atoms and a melt transition (endothermic maximum) in the DSC(differential scanning calorimetry) of greater than about 110° C.

In a further preferred embodiment, there is provided a polymer derived from ethylene alone that has a broad composition distribution and a molecular weight distribution of less than 6 and greater than 2.5, wherein said polymer has an average degree of branching of from 5 to 120 alkyl branches per 1000 carbon atoms, and wherein any individual component of said polymer has a degree of branching of from 0 to 150 alkyl branches per 1000 carbon atoms. In a further preferred embodiment, an individual component of the polymer has between about 40 and 100 branches per 1000 carbon atoms, another component has between about 30 and 90 branches per 1000 carbon atoms, another component has between about 30 and 80 branches per 1000 carbon atoms, another component has between about 20 and 60 branches per 1000 carbon atoms, another component has between about 10 and 50 branches per 1000 carbon atoms, another component has between about 10 and 40 branches per 1000 carbon atoms, another component has between about 5 and 35 branches per 1000 carbon atoms, another component has between about 0 and 25 branches per 1000 carbon atoms, another component has between about 0 and 30 branches per 1000 carbon atoms, another component has between about 0 and 20 branches per 1000 carbon atoms.

Preferred olefins useful in the practice of the processes of the present invention include ethylene and α-olefins such as propylene, 1-butene, 1-hexene, 1-octene, ethyl undecenoate and cyclic olefins such as cyclopentene.

When the polymerizations are conducted in the liquid phase, said liquid phase may include solvent or neat monomer. The molar ratio of neutral Lewis acid to transition metal complex can be from 1 to 10000, preferably 10 to 1000. The pressure at which the ethylene polymerizations and copolymerizations take place can be from 1 atmosphere to 1000 atmospheres, preferably 1 to 100 atmospheres.

While not wishing to be bound by theory, the present inventors believe that the Lewis acid may be acting to further activate the catalysts provided herein via coordination to one or more of those heteroatoms which are not directly bound to the transition metal M, but which are π-conjugated to the nitrogens which are bound to the transition metal M. Substituents which contain additional Lewis basic groups, including, but not limited to, methoxy groups, positioned so as to further promote the binding of the Lewis acid at such π-conjugated heteroatoms, are also included in this invention. A nonlimiting example of secondary Lewis acid binding would include the following:

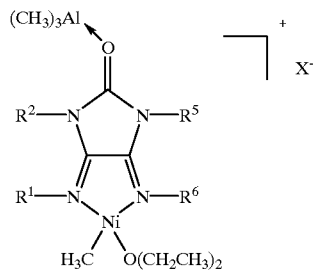

XLIII wherein $R^1$, $R^2$, $R^5$, and $R^6$ are 2,6-dimethylphenyl; and $X^-$ is a weakly coordinating anion.

The polymerizations may be conducted as solution polymerizations, as non-solvent slurry type polymerizations, as slurry polymerizations using one or more of the olefins or other solvent as the polymerization medium, or in the gas phase. One of ordinary skill in the art, with the present disclosure, would understand that the catalyst could be supported using a suitable catalyst support and methods known in the art. Substantially inert solvents, such as toluene, hydrocarbons, methylene chloride and the like, may be used. Propylene and 1-butene are excellent monomers for use in slurry-type copolymerizations and unused monomer can be flashed off and reused.

Temperature and olefin pressure have significant effects on polymer structure, composition, and molecular weight. Suitable polymerization temperatures are preferably from about −100° C. to about 200° C., more preferably in the 20° C. to 150° C. range.

After the reaction has proceeded for a time sufficient to produce the desired polymers, the polymer can be recovered from the reaction mixture by routine methods of isolation and/or purification.

In general, the polymers of the present invention are useful as components of thermoset materials, as elastomers, as packaging materials, films, compatibilizing agents for polyesters and polyolefins, as a component of tackifying compositions, and as a component of adhesive materials.

High molecular weight resins are readily processed using conventional extrusion, injection molding, compression molding, and vacuum forming techniques well known in the art. Useful articles made from them include films, fibers, bottles and other containers, sheeting molded objects and the like.

Low molecular weight resins are useful, for example, as synthetic waxes and they may be used in various wax coatings or in emulsion form. They are also particularly useful in blends with ethylene/vinyl acetate or ethylene/methyl acrylate-type copolymers in paper coating or in adhesive applications.

Although not required, typical additives used in olefin or vinyl polymers may be used in the new homopolymers and copolymers of this invention. Typical additives include pigments, colorants, titanium dioxide, carbon black, antioxidants, stabilizers, slip agents, flame retarding agents, and the like. These additives and their use in polymer systems are known per se in the art.

The molecular weight data presented in the following examples is determined at 135° C. in 1,2,4-trichlorobenzene using refractive index detection, calibrated using narrow molecular weight distribution poly(styrene) standards.

EXAMPLES

Other features of the invention will become apparent in the course of the following descriptions of exemplary embodiments which are given for illustration of the invention and are not intended to be limiting thereof.

Example 1
Preparation of N,N'-bis(2,6-dimethylphenyl)oxalamide.

2,6-dimethylaniline, triethylamine, and dichloromethane were dried by passage through basic alumina. A 1 L round bottom flask, equipped with a magnetic stir bar and a 125 mL pressure-equalizing dropping funnel capped by a nitrogen inlet adapter, was charged with 53.38 g of 2,6-dimethylaniline, 250 mL of dichloromethane, and 44.76 g of triethylamine. A solution of 25.34 g of oxalyl chloride in 80 mL of dichloromethane was added dropwise under nitrogen with stirring and ice-bath cooling over 1.2 hours to give a thick paste which had to be occasionally swirled by hand to effect mixing. The mixture was allowed to stir at room temperature for 14 hours, then transferred to a separatory funnel, washed 3 times with water, separated and concentrated under reduced pressure (10 mm Hg) to give 63 g of crude solid. The crude product was dissolved in a boiling mixture of 1.30 L of toluene and 2.85 L of absolute ethanol, cooled to room temperature (about 23° C.) and diluted with 260 mL of water, then allowed to crystallize for 16 hours. The resultant precipitate was isolated by vacuum filtration, washed with methanol (3×100 mL) and dried to give 39.1 g (66%) as white crystals. An additional 9.5 g (16.1 %) was recovered from the filtrate by further dilution with approximately 500 mL of water. Field desorption mass spectrometry showed a parent ion peak at 296 m/z. $^1$H NMR (300 MHz, $CDCl_3$, chemical shifts in ppm relative to TMS at 0 ppm): 2.29 (12 p, s), 7.15 (6 p, m), 8.86 (2 p, br s).

Example 2
Preparation of N, N'-bis(2,6-diisopropylphenyl)oxalamide.

2,6-Diisopropylaniline, triethylamine, and dichloromethane were dried by passage through basic alumina. A 1 L round bottom flask, equipped with a magnetic stir bar and a 125 mL pressure-equalizing dropping funnel capped by a nitrogen inlet adapter, was charged with 34.73 g of 2,6-diisopropylaniline (previously distilled), 180 mL of dichloromethane, and 18.30 g of triethylamine. A solution of 10.57 g oxalyl chloride in 43 mL of dichloromethane was added dropwise under nitrogen with stirring and ice-bath cooling over 38 minutes to give a thick paste which had to be occasionally swirled by hand to effect mixing. The mixture was allowed to stir at room temperature (about 23° C.) for 60 hours, then diluted with 700 mL of water to precipitate the product, which was isolated by filtration, washed with water and recrystallized from boiling isopropanol (4 L) to afford 22.38 g (66%) of white needles. Field desorption mass spectrometry showed a parent ion peak at 408 m/z. $^1$H NMR (500 MHz, $CD_2Cl_2$, chemical shifts in ppm relative to TMS at 0 ppm): 1.22 (24 p, d, 6.8 Hz), 3.08 (4 p, septet, 6.8 Hz), 7.25 (4 p, d, 7.5 Hz), 7.37 (2 p, t, 7.5 Hz), 8.86 (2 p, br s).

Example 3
Preparation of N,N'-bis (4-methoxy-2,6-dimethylphenyl) oxalamide.

Triethylamine and dichloromethane were dried by passage through basic alumina. A 50 mL round bottom flask, equipped with a magnetic stir bar and a small pressure-equalized dropping funnel capped by a nitrogen inlet adapter, was charged with 1.5 g of 4-methoxy-2,6-dimethylphenylamine, 8 mL of dichloromethane, and 1.38 g of triethylamine. A solution of 0.39 of oxalyl chloride in 2 mL of dichloromethane was added dropwise under a nitrogen atmosphere with stirring and ice-bath cooling over 35 min. The mixture was allowed to stir at room temperature for 14 hours, then transferred to a separatory funnel, washed with water, separated and concentrated under reduced pressure (10 mm Hg) to give 1.75 g solids. The crude product was dissolved in 150 mL of boiling absolute ethanol and crystallized upon cooling to room temperature (about 23° C.). The resultant precipitate was isolated by vacuum filtration, and dried to give 1.39 g (86%) as white crystals. Field desorption mass spectrometry showed a parent ion peak at 356 m/z.

Example 4
Preparation of $N^1,N^2$-bis(2,6-dimethylphenyl) oxalodiimidoyl dichloride.

A 1 L round bottom flask was charged with 30.0 g of N,N'-bis(2,6-dimethylphenyl)oxalamide, 58.8 g of phosphorous pentachloride and 150 mL of dry toluene, and equipped with a magnetic stir bar and a reflux condenser capped by a nitrogen inlet adapter connected to a bubbler. The mixture was heated to reflux over 30 minutes, then maintained at reflux under nitrogen for another 95 minutes to give a yellow solution. Heating was discontinued and the mixture was allowed to cool to room temperature (about 23° C.). A short path distillation adapter and receiving flask was attached in place of the condenser and the volatiles were removed under reduced pressure (1 mm Hg), initially at room temperature, then at 100° C., to give 20.1 g (60%) of a granular yellow solid. Field desorption mass spectrometry showed a parent ion peak at 332 m/z. $^1$H NMR (300 MHz, $C_6D_6$, chemical shifts in ppm relative to TMS at 0 ppm): 2.04 (12 p, s), 6.91 (6 p, s).

Example 5
Preparation of $N^1,N^2$-bis(2,6-diisopropylphenyl) oxalodiimidoyl dichloride.

A 500 mL round bottom flask equipped with a magnetic stir bar and a reflux condenser capped by a nitrogen inlet adapter connected to a bubbler was charged with 2.50 g of N,N'-bis(2,6-diisopropylphenyl)oxalamide, 3.58 g of phosphorous pentachloride and 36 mL of dry toluene. The mixture was heated to reflux over 30 minutes, then maintained at reflux under nitrogen for another 210 minutes to afford a clear yellow solution. Heating was discontinued and the mixture was allowed to cool to room temperature (about 23° C.). A short path distillation adapter and receiving flask were attached in place of the condenser and the volatiles were removed under reduced pressure (1 mm Hg), initially at room temperature, then at 100° C., to give a yellow oil, which slowly crystallized upon complete cooling. The product was purified by column chromatography ($SiO_2$, Merck Grade 9385 230–400 mesh, 60 Å; 3 v % ethyl acetate in hexane) to afford 1.49 g (55%) yellow crystals. Field desorption mass spectrometry showed a parent ion peak at 444 m/z.

Example 6
Preparation of $N^1,N^2$-bis(4-methoxy-2,6-dimethylphenyl) oxalodiimidoyl dichloride.

A 50 mL round bottom flask was charged with 1.37 g of N,N'-bis(4-methoxy-2,6-dimethylphenyl)oxalamide 1.88 g of phosphorous pentachloride and 15 mL of dry toluene, and equipped with a magnetic stir bar and a reflux condenser capped by a nitrogen inlet adapter connected to a bubbler. The mixture was heated, with stirring, at about 100° C. until the evolution of HCl ceased. Then, another 0.22 g $PCl_5$ was added and the mixture was heated another 30 min at 80° C. After cooling to room temperature the mixture was transferred to a separatory funnel, and some crystallization occurred upon transfer. Complete transfer and re-dissolution of the product was accomplished by the addition of dichloromethane. The organic layer was washed with saturated aqueous sodium bicarbonate, then concentrated in vacuo to afford 1.44 g crystalline yellow solid. Field desorption mass spectrometry showed a parent ion peak at 392 m/z.

Example 7

Preparation of 2,3-bis(2,6-dimethylphenylimino)-[1,4]dithiane.

A 50 mL round bottom flask equipped with a magnetic stir bar and a reflux condenser capped by a nitrogen inlet was charged with 504 mg of $N^1,N^2$-bis(2,6-dimethylphenyl) oxalodiimidoyl dichloride, 136 mg of sodium hydride (60% mineral oil dispersion), 4.0 mL of dry tetrahydrofuran and 0.140 mL of 1,2-ethanedithiol. The mixture was heated at reflux for 2 hours, after which another 66 mg of sodium hydride dispersion was added and the mixture was refluxed for an additional hour. After cooling, the mixture was diluted with water and diethyl ether, and the ether layer was separated, washed again with water, and dried with magnesium sulfate to afford a yellow-orange oil. Column chromatography (SiO$_2$, Merck Grade 9385 230–400 mesh, 60 Å; 15 v % of ethyl acetate in hexane) afforded 296 mg of a yellow oil which was crystallized by addition of hexane and collected by vacuum filtration to give 219 mg of yellow granular crystals. Field desorption mass spectrometry showed a parent ion peak at 354 m/z. $^1$H NMR (300 MHz, CDCl$_3$, chemical shifts in ppm relative to TMS at 0 ppm): 2.17 (12 p, s), 3.27 (4 p, br s), 6.4–7.12 (6 p, m).

Example 8

Preparation of 2,3-bis(2,6-diisopropylphenylimino)-[1,4]dithiane.

A 250 mL round bottom flask equipped with a magnetic stir bar and a reflux condenser capped by an argon inlet was sequentially charged with 0.69 g of a 60% dispersion of sodium hydride in mineral oil, 3.34 g of $N^1,N^2$-bis(2,6-diisopropylphenyl)oxalodiimidoyl dichloride, 20 mL of dry tetrahydrofuran, and 0.70 mL of 1,2-ethanedithiol. The mixture was heated under argon at reflux for 3 hours, after which another 0.25 g of sodium hydride dispersion was added and the mixture was refluxed for an additional 2.5 hours. After cooling, the mixture was diluted with water and diethyl ether, and the ether layer was separated, washed with water, and dried with magnesium sulfate to afford a yellow-orange oil. Column chromatography (SiO$_2$, Merck Grade 9385 230–400 mesh, 60 Å; 10 v % ethyl acetate in hexane) afforded 3.14 g of a yellow-orange glass. Field desorption mass spectrometry showed a parent ion peak at 466 m/z. $^1$H NMR (500 MHz, CD$_2$Cl$_2$, chemical shifts in ppm relative to TMS at 0 ppm): 1.10–1.22 (12 p, m), 1.22–1.40 (12 p, m), 2.78–3.05 (4 p, m), 3.30 (4 p, br s), 7.05–7.25 (6 p, m).

Example 9

Preparation of 2,3-bis(phenylimino)-[1,4]dithiane.

A 250 mL round bottom flask equipped with a magnetic stir bar and a reflux condenser capped by an argon inlet was sequentially charged with 0.69 g of a 60% dispersion of sodium hydride in mineral oil, a freshly prepared solution of 2.08 g $N^1,N^2$-diphenyloxalodiimidoyl dichloride in 20 mL of dry tetrahydrofuran, and 0.70 mL of 1,2-ethanedithiol. The mixture was heated under argon at reflux for 2 hours, after which another 0.30 g of sodium hydride dispersion was added and the mixture refluxed for an additional 3 hours. After cooling, the mixture was diluted with water and diethyl ether, and the ether layer was separated, washed with water, and dried with magnesium sulfate to afford a yellow-orange gummy solid. Column chromatography (SiO$_2$, Merck Grade 9385 230–400 mesh, 60 Å, 10 v % ethyl acetate in hexane) afforded 296 mg of a yellow oil which was crystallized by addition of hexane to give 0.161 g of yellow-orange granular crystals. Field desorption mass spectrometry showed a parent ion peak at 298 m/z. $^1$H NMR (300 MHz, CDCl$_3$, chemical shifts in ppm relative to TMS at 0 ppm): 3.27 (4 p, br s), 7.02 (4 p, apparent d, 8.1 Hz), 7.19 (2 p, apparent t, 7.2 Hz), 7.40 (4 p, apparent t, 7.8 Hz).

Example 10

Preparation of 2,3-bis(2,6-dimethylphenylimino)-2,3-dihydrobenzo[1,4]dithiine.

A 100 mL round bottom flask equipped with a magnetic stir bar and a reflux condenser capped by an argon inlet was sequentially charged with 0.294 g of a 60% dispersion of sodium hydride in mineral oil, 4 mL of dry tetrahydrofuran, and 0.253 g of 1,2-benzenedithiol. After the bubbling had subsided, 0.600 g of $N^1,N^2$-bis(2,6-dimethylphenyl) oxalodiimidoyl dichloride was added. The mixture was stirred at 25° C. for 45 minutes then heated to reflux over 15 minutes and held at reflux for 1 hour. After cooling, the mixture was diluted with water and diethyl ether, and the ether layer was separated, washed with water, and dried with magnesium sulfate, and concentrated in vacuo to give a yellow-orange oil. Column chromatography (SiO$_2$, Merck Grade 9385 230–400 mesh, 60 Å; 2 v % ethyl acetate in hexane) afforded 0.412 g of a yellow-orange glass. Field desorption mass spectrometry showed a parent ion peak at 402 m/z. $^1$H NMR (300 MHz, CDCl$_3$, chemical shifts in ppm relative to TMS at 0 ppm): 2.16 (12 p, s), 7.01–7.24 (10 p, m).

Example 11

Preparation of 2,3-bis(4-methoxy-2,6-dimethylphenylimino)-[1,4]dithiane.

A 50 mL round bottom flask equipped with a magnetic stir bar and a reflux condenser capped by a nitrogen inlet was charged with 420 mg of $N^1,N^2$-bis(4-methoxy-2,6-dimethylphenyl)oxalodiimidoyl dichloride. To a 50 mL pear flask was added 171 mg of sodium hydride (60% mineral oil dispersion), 1.75 mL of dry tetrahydrofuran, and, cautiously, 0.11 mL ethane dithiol. The resulting mixture was syringed into the $N^1,N^2$-bis(4-methoxy-2,6-dimethylphenyl) oxalodiimidoyl dichloride solution using 5 mL dry THF to complete the transfer. The reaction flask was heated at reflux for 3 hours, after which another 45 mg of sodium hydride dispersion and another 20 µL ethane dithiol was added and the mixture was refluxed for an additional hour. After cooling, the mixture was diluted with water and diethyl ether, and the ether layer was separated, washed again with water, dried with magnesium sulfate, and concentrated to afford a yellow-orange solid. Column chromatography (SiO$_2$, Merck Grade 9385 230–400 mesh. 60 Å; 15 v % ethyl acetate in hexane) afforded 147 mg of a yellow powder. Field desorption mass spectrometry showed a parent ion peak at 414 m/z.

Example 12

Preparation of 2,3-bis(2,6-dimethylphenylimino)-[1,4]dioxane.

A 50 mL round bottom flask equipped with a magnetic stir bar and a reflux condenser capped by a nitrogen inlet was charged with 504 mg of $N^1,N^2$-bis(2,6-dimethylphenyl) oxalodiimidoyl dichloride, 66 mg of sodium hydride (60% mineral oil dispersion), 5.0 mL of dry tetrahydrofuran, 0.230 mL of triethylamine (dried by passage through alumina) and 0.093 mL of dry ethylene glycol. The mixture was heated at reflux for 105 minutes, after which another 66 mg of sodium hydride dispersion was added and the mixture was refluxed for an additional hour. After cooling, the mixture was diluted with water and diethyl ether, and the ether layer was separated, washed again with water, dried with magnesium sulfate, and concentrated to afford a yellow oil. Crystallization from heptane gave rosettes of off-white crystals (225 mg, 1st crop). Field desorption mass spectrometry showed a parent ion peak at 322 m/z. $^1$H NMR (300 MHz, CDCl$_3$, chemical shifts in ppm relative to TMS at 0 ppm): 2.20 (12 p, s), 4.35 (4 p, s), 6.94 (2 p, m). 7.05 (4 p, m).

Example 13

Preparation of 5-methoxymethyl-2,3-bis(2,6-dimethylphenylimino)-[1,4]dioxane.

A 50 mL round bottom flask equipped with a magnetic stir bar and a reflux condenser capped by an argon inlet was charged with 504 mg of N$^1$,N$^2$-bis(2,6-dimethylphenyl) oxalodiimidoyl dichloride, 155 mg of sodium hydride (60% mineral oil dispersion), 3.5 mL of dry tetrahydrofuran and 188 mg of 3-methoxy-1,2-propanediol. The mixture was heated to reflux over 10 min and held at reflux for 2 hours. After cooling, the mixture was diluted with diethyl ether, and washed with water (2×100 mL), and dried with magnesium sulfate and concentrated in vacuo to afford 329 mg of a yellow oil. Column chromatography (SiO$_2$, Merck Grade 9385 230–400 mesh. 60 Å; 20 v % of ethyl acetate in hexane) afforded 216 mg of a glassy yellow solid. Field desorption mass spectrometry showed a parent ion peak at 366 m/z. $^1$H NMR (300 MHz, CDCl$_3$, chemical shifts in ppm relative to TMS at 0 ppm): 2.18 (12 p, s), 3.31 (3 p, s), 3.45–3.65 (2 p, m), 4.20–4.40 (2 p, m), 4.40–4.55 (1 p, m), 6.80–7.15 (6 p, m).

Example 14

Preparation of 2,3-bis(benzyloxymethyl)-5,6-bis(2,6-dimethylphenylimino)-[1,4]dioxane.

A 100 mL round bottom flask equipped with a magnetic stir bar and a reflux condenser capped by an argon inlet was charged with 265 mg of sodium hydride (60% mineral oil dispersion), 7.5 mL of dry tetrahydrofuran, 1.0 g of 3-methoxy-1,2-propanediol and 1.0 g of N$^1$,N$^2$-bis(2,6-dimethylphenyl)oxalodiimidoyl dichloride. The yellow mixture was heated to reflux over 15 min and became very viscous. More tetrahydrofuran (5 mL) was added and the mixture was stirred with a glass rod, then heated for another 30 min. Next, an additional 220 mg of sodium hydride (60% mineral oil dispersion) and an additional 10 mL tetrahydrofuran were added. Most of the yellow color was discharged with the second addition of sodium hydride, rendering the very viscous reaction mixture light brown. Heating was continued for about 15 min more, and after cooling, the mixture was diluted with diethyl ether and washed with water to remove the sodium chloride. Column chromatography (SiO$_2$, Merck Grade 9385 230–400 mesh, 60 Å; 2 v % of ethyl acetate in hexane) afforded a beige gummy solid. Field desorption mass spectrometry showed a parent ion peak at 562 m/z. $^1$H NMR (300 MHz, CDCl$_3$, chemical shifts in ppm relative to TMS at 0 ppm): 2.17 (12 p, s), 3.63 (4 p, br s), 4.38 (2 p, d, 12.6 Hz), 4.47 (2 p, d, 12.6 Hz), 4.56 (2 p, br s), 6.85–7.4 (16 p, m).

Example 15

Preparation of 2,3-bis(2,6-diisopropylphenylimino)-[1,4] dioxane.

A 50 mL round bottom flask equipped with a magnetic stir bar and a reflux condenser capped by a nitrogen inlet was charged with 1.0 g of N$^1$,N$^2$-bis(2,6-diisopropylphenyl) oxalodiimidoyl dichloride, 268 mg of sodium hydride (60% mineral oil dispersion), 4.0 mL of dry tetrahydrofuran, and 212 mg of dry ethylene glycol. Under an argon atmosphere, the mixture was heated to 65° C. held at that temperature for 90 minutes. The mixture was then quickly heated to reflux and held at reflux for 30 minutes more. After cooling, the mixture was diluted with 50 mL diethyl ether, and washed with water, dried with magnesium sulfate, and concentrated in vacuo to afford a light straw-yellow oil (903 mg). Column chromatography (SiO$_2$, Merck Grade 9385 230–400 mesh, 60 Å; 8 v % ethyl acetate in hexane) afforded 257 mg of a pale green glass. Field desorption mass spectrometry showed a parent ion peak at 434 m/z. $^1$H NMR (300 MHz, CDCl$_3$, chemical shifts in ppm relative to TMS at 0 ppm): 1.24 (24 p, d, 6.6 Hz), 3.00 (4 p, septet, 6.6 Hz), 4.31 (4 p, br s), 7.04–7.20 (6 p, m).

Example 16

Preparation of 2,3-bis(2,6-dimethylphenylimino)-4-methylmorpholine.

A 50 mL round bottom flask equipped with a magnetic stir bar and a reflux condenser capped by a nitrogen inlet adapter was charged with 503 mg of N$^1$,N$^2$-bis(2,6-dimethylphenyl) oxalodiimidoyl dichloride, 346 mg triethylamine, 4 mL dry, deoxygenated toluene, and 0.135 mL 2-(methylamino) ethanol. The mixture was heated to reflux under nitrogen over 30 minutes and maintained at reflux for another 4.25 hours. After cooling, the mixture was diluted with 45 mL diethyl ether and washed three times with water (110 mL total). The ether extract was dried with magnesium sulfate, filtered and concentrated under reduced pressure (10 mm Hg) to give a light-colored solid (512 mg). Recrystallization from heptane/dichloromethane gave 138 mg pale off-white crystals (first crop). Field desorption mass spectrometry showed a parent ion peak at 335 m/z. $^1$H NMR (300 MHz, CDCl$_3$, chemical shifts in ppm relative to TMS at 0 ppm): 1.73 (6 p, s), 2.10 (6 p, s), 3.27 (3 p, s), 3.55–3.65 (2 p, m), 4.16–4.26 (2 p, m), 6.65–6.95 (6 p, m).

Example 17

Preparation of 2,3-bis(2,6-diisopropylphenylimino)-4-methylmorpholine.

A 50 mL round bottom flask equipped with a magnetic stir bar and a reflux condenser capped by a nitrogen inlet adapter was charged with 725 mg of N$^1$,N$^2$-bis(2,6-diisopropylphenyl)oxalodiimidoyl dichloride, 143 mg of sodium hydride (60% mineral oil dispersion), 4 mL dry tetrahydrofuran, and 0.144 mL 2-(methylamino)ethanol. The mixture was stirred at room temperature for 4 hours, and allowed to stand at room temperature for another 5 days. The mixture was diluted with diethyl ether and washed water. The ether extract was concentrated under reduced pressure (10 mm Hg) to give a yellow oil which partially crystallized over several hours). Column chromatography (SiO$_2$, Merck Grade 9385 230–400 mesh, 60 Å; 12 v % of ethyl acetate in hexane) afforded 156 mg light yellow crystalls. Field desorption mass spectrometry showed a parent ion peak at 447 m/z. $^1$H NMR (300 MHz, CDCl$_3$, chemical shifts in ppm relative to TMS at 0 ppm): 0.86 (6 p, d, 7.2 Hz), 1.04 (6 p, d, 7.2 Hz), 1.15 (6 p, d, 7.2 Hz), 1.18 (6 p, d, 7.2 Hz), 2.27 (2 p, apparent septet, 7.2 Hz), 2.97 (2 p, apparent septet, 7.2 Hz), 3.28 (3 p, br s), 3.55–3.65 (2 p, m), 4.14–4.22 (2 p, m), 6.80–7.02 (6 p, m).

Example 18

Preparation of 1,3-bis-(2,6-dimethyl-phenyl)-4,5-bis-(2,6-dimethylphenylimino)-imidazolidin-2-one.

In a 250 mL round bottom flask, 1.0 g of N$^1$,N$^2$,N$^3$,N$^4$-tetrakis(2,6-dimethylphenyl)oxalamidine was dissolved in 35 mL dry, deoxygenated dichloromethane while stirring under an argon atmosphere. 0.67 mL dry triethylamine was added, followed by 240 mg triphosgene. With the addition of the triphosgene, the color shifted from pale yellow to chrome yellow. The mixture was allowed to stir for 16 h at room temperature, after which time an additional 460 mg of triphosgene was added. After about 15 min, 10 mg dimethylamino pyridine and an additional 240 mg triphosgene were added. After about 15 min more, another 220 mg triphosgene and about 0.5 g dimethylamino pyridine were added. The mixture was washed with saturated aqueous sodium bicarbonate, then with water, and then concentrated in vacuo to afford a yellow powder. Column chromatography ($SiO_2$, Merck Grade 9385 230–400 mesh, 60 Å; 4 v % ethyl acetate in hexane) afforded 763 mg of a chrome yellow powder. Field desorption mass spectrometry showed a parent ion peak at 528 m/z. $^1$H NMR (300 MHz, $CDCl_3$, chemical shifts in ppm relative to TMS at 0 ppm): 2.01 (12 p, s), 2.32 (12 p, s), 6.4–7.3 (12 p, m).

Example 19

Preparation of 1,3-bis(4-methoxy-2,6-dimethylphenyl)-4,5-bis-(4-methoxy-2,6-dimethylphenylimino)imidazolidin-2-one.

A 100 mL round bottom was equipped with a magnetic stirrer and charged with 0.75 mL dry triethylamine, 6 mL dry and deoxygenated chloromethane, and 0.335 g $N^1,N^2,N^3,N^4$-tetrakis(4-methoxy-2,6-dimethylphenyl)oxalamidine. With stirring, 178 mg triphosgene was added, and the flask was quickly capped with a septum. A precipitate formed and the color shifted from yellow to orange. After 2.5 days another 78 mg triphosgene was added, and the reaction left to stir another 2 hours. 150 mg more triphosgene was added, and the reaction left to stir for another 16 hrs. The reaction mixture was diluted with 50 mL diethyl ether and washed with water (2×50 mL). The aqueous washings were back-extracted with dichloromethane. The organic layers were combined and dried over magnesium sulfate, and concentrated in vacuo to afford an orange oil. Upon addition of diethyl ether to the oil, small orange crystals formed. The compound was isolated on a vacuum filter and washed with diethyl ether to afford 216 mg yellow-orange microcrystalline powder. Field desorption mass spectrometry showed a parent ion peak at 648 m/z. $^1$H NMR (500 MHz, $CD_2Cl_2$, chemical shifts in ppm relative to TMS at 0 ppm): 1.98 (12 p, broad hump), 2.25 (12 p, broad hump), 3.63 (6 p, broad hump), 3.75 (6 p, broad hump), 6.32 (4 p, broad hump), 6.59 (4 p, broad hump).

Example 20

Preparation of $N^1,N^2,N^3,N^4$-tetrakis(2,6-dimethylphenyl) oxalamidine.

A 1 L round bottom flask equipped with a magnetic stir bar and a reflux condenser capped by a nitrogen inlet was charged with 5.6 g of $N^1,N^2$-bis(2,6-dimethylphenyl) oxalodiimidoyl dichloride, 43 mL of dry toluene and 32.7 g of 2,6-dimethylaniline (dried by passage through alumina). The mixture was heated to reflux under nitrogen over 30 minutes, then maintained at reflux another 3 hours. After cooling, the mixture was diluted with 206 g of absolute ethanol and 45 g of water to produce copious amounts of precipitate. Isolation by vacuum filtration, with ethanol (600 mL) and heptane (600 mL) washes, and subsequent drying, gave 6.1 g (72%) as pale yellow crystals. Field desorption mass spectrometry showed a parent ion peak at 502 m/z. $^1$H NMR (300 MHz, $CDCl_3$, chemical shifts in ppm relative to TMS at 0 ppm): 2.16 (24 p, s), 6.75 (12 p, s), 8.6 (2 p, br s).

Example 21

Preparation of $N^1,N^2,N^3,N^4$-tetrakis(4-methoxy-2,6-dimethylphenyl)oxalamidine.

A 500 mL round bottom flask equipped with a magnetic stir bar and a reflux condenser capped by a nitrogen inlet was charged with 1.0 g of $N^1,N^2$-bis(4-methoxy-2,6-dimethylphenyl)oxalodiimidoyl dichloride, 24 mL of dry toluene and 854 mg of 4-methoxy-2,6-dimethylphenylamine, and 0.90 mL triethylamine (dried by passage through alumina). The mixture was heated to reflux under nitrogen over 30 minutes, then maintained at reflux another 14 hours. After cooling, the mixture was diluted with dichloromethane and washed with water. The impure compound was adsorbed onto $SiO_2$, and column chromatography ($SiO_2$, Merck Grade 9385 230–400 mesh, 60 Å; 12.5 v % ethyl acetate in hexane) afforded 340 mg of a yellow powder. Field desorption mass spectrometry showed a parent ion peak at 622 m/z.

Example 22

Preparation of 1,4-dimethyl-2,3-bis(2,6-dimethylphenylimino)piperazine.

A 25 mL round bottom flask equipped with a magnetic stir bar and a reflux condenser capped by a nitrogen inlet adapter was charged with 0.50 g of $N^1,N^2$-bis(2,6-dimethylphenyl) oxalodiimidoyl dichloride, 1.1 mL of N,N'-dimethylethylenediamine and 4.0 mL of dry toluene. The mixture was heated to reflux under nitrogen over 15 minutes and maintained at reflux for another 30 minutes. After cooling, the mixture was diluted with diethyl ether and washed three times with water. The ether extract was dried with magnesium sulfate, filtered and concentrated under reduced pressure (10 mm Hg) to give a yellow solid (0.50 g). Recrystallization from heptane gave pale yellow crystals. Field desorption mass spectrometry showed a parent ion peak at 348 m/z. $^1$H NMR (300 MHz, $CDCl_3$, chemical shifts in ppm relative to TMS at 0 ppm): 1.83 (br s, 12 p), 2–3.4 (two very broad humps, 4 p), 3.42 (br s, 6 p), 6.66 (t, 2 p), 6.84 (d, 4 p).

Example 23

Preparation of the nickel dibromide complex of 2,3-bis(2,6-dimethylphenylimino)-[1,4]dithiane.

A 50 mL Schlenk flask equipped with a magnetic stir bar and capped with a septum was charged with 100 mg of 2,3-bis(2,6-dimethylphenylimino)-[1,4]dithiane and 79 mg of (1,2-dimethoxyethane)nickel(II) dibromide under an inert atmosphere. Dry, deoxygenated dichloromethane (5 mL) was added and the mixture was stirred under an argon atmosphere, turning red-brown within about 5 minutes and slowly producing a red-brown crystalline precipitate. After 1 hour, another 5 mL of dichloromethane was added. The mixture was stirred another 21 hours at 21° C., then diluted with 10 mL of dry, deoxygenated hexane and stirred another 8 hours. The supernatant was removed via a filter paper-tipped cannula, and the residue dried in vacuo at 1 mm Hg to afford 116 mg of red-brown crystals.

Example 24

Preparation of the nickel dibromide complex of 2,3-bis(2,6-diisopropylphenylimino)-[1,4]dithiane.

A Schlenk flask equipped with a magnetic stir bar was charged with 79 mg of 2,3-bis(2,6-diisopropylphenylimino)-[1,4]dithiane (0.17 mmol) and 49 mg of (1,2-dimethoxyethane)nickel(II) dibromide (0.16 mmol)under an argon atmosphere. Dry, deoxygenated dichloromethane (15 mL) was added and the mixture was stirred under an argon atmosphere, turning red-brown within about 10 minutes. After 2 hours, the $CH_2Cl_2$ was removed in vacuo. The resulting red-brown solid was washed with 2×10 mL of hexane and the solid was dried in vacuo for several hours affording 76 mg of a brown solid.

Example 25
Preparation of the nickel dibromide complex of 2,3-bis (phenylimino)-[1,4]dithiane.

A 50 mL Schlenk flask equipped with a magnetic stir bar and capped with a septum was charged with 151 mg of 2,3-bis(phenylimino)-[1,4]dithiane and 123 mg of (1,2-dimethoxyethane)nickel(II) dibromide under an inert atmosphere. Dry, deoxygenated dichloromethane (10 mL) was added and the mixture was stirred under an argon atmosphere, turning dark brown within about 5 minutes and slowly producing a red-brown crystalline precipitate. After 80 minutes, the mixture was concentrated to apparent dryness under a stream of argon, then further dried in vacuo for 1 hour at 50 mtorr to afford a red-brown powder.

Example 26
Preparation of the nickel dibromide complex of 2,3-bis(2, 6-dimethylphenylimino)-2,3-dihydrobenzo[1,4]dithiine.

A 50 mL Schlenk flask equipped with a magnetic stir bar and capped with a septum was charged with 110 mg of 2,3-bis-(2,6-dimethylphenylimino)-2.3-dihydrobenzo[1,4] dithiine and 71 mg of (1,2 -dimethoxyethane)nickel(II) dibromide under an inert atmosphere. Dry, deoxygenated dichloromethane (8 mL) was added and the mixture was stirred under an argon atmosphere, quickly turning red-brown. The mixture was stirred for 1 hour, concentrated to dryness under a stream of argon, then further dried in vacuo for 1 hour at 50 mtorr to yield a red-brown crystalline powder.

Example 27
Preparation of the nickel dibromide complex of 2,3-bis(4-methoxy-2,6-dimethylphenylimino)-[1,4]dithiane.

A 50 mL Schlenk flask equipped with a magnetic stir bar and capped with a septum was charged with 147 mg of 2,3-bis(4-methoxy-2,6-dimethylphenylimino)-[1,4]dithiane and 93 mg of (1,2-dimethoxyethane)nickel(II) dibromide under an inert atmosphere. Dry, deoxygenated dichloromethane (10 mL) was added and the mixture was stirred under an argon atmosphere, turning dark brown almost immediately, and producing a brown precipitate. After 2 hours, 10 mL dry and deoxygenated hexane was added to complete the precipitation. The supernatant was removed via filter paper-tipped cannula, the residue dried in vacuo (0.5 mm Hg) for 14 h to obtain the product as a brown microcrystalline solid.

Example 28
Preparation of the nickel dibromide complex of 2,3-bis(2, 6-dimethylphenylimino)-[1,4]dioxane.

A 50 mL Schlenk flask equipped with a magnetic stir bar and capped with a septum was charged with 100 mg of 2,3-bis(2,6-dimethylphenylimino)-[1,4]dioxane and 87 mg of (1,2-dimethoxyethane)nickel(II) dibromide under an inert atmosphere. Dry, deoxygenated dichloromethane (5 mL) was added and the mixture was stirred under an argon atmosphere, slowly producing a brown crystalline precipitate. After 1 hour, another 5 mL of dichloromethane was added. The mixture was stirred another 21 hours at 21° C., then diluted with 10 mL of dry, deoxygenated hexane and stirred another 8 hours. The supernatant was removed via a filter paper-tipped cannula, and the residue dried in vacuo at 1 mm Hg to afford 117 mg of brown crystals.

Example 29
Preparation of the nickel dibromide complex of 2,3-bis (benzyloxymethyl)-5,6-bis(2,6-dimethylphenylimino)-[1,4] dioxane.

A 50 mL Schlenk flask equipped with a magnetic stir bar and capped with a septum was charged with 172 mg of 2,3-bis(benzyloxymethyl)-5,6-bis(2,6-dimethylphenylimino)-[1,4]dioxane and 85 mg of (1,2-dimethoxyethane)nickel(II) dibromide under an inert atmosphere. Dry, deoxygenated dichloromethane (12 mL) was added and the mixture was stirred under an argon atmosphere, almost immediately turning red-brown. After 1.75 hours, the mixture was concentrated dryness under a stream of argon for 16 h, then further dried in vacuo to afford 182 mg of a red-brown crystalline powder.

Example 30
Preparation of the nickel dibromide complex of 2,3-bis(2, 6-dimethylphenylimino)-4-methylmorpholine.

A 25 mL Schlenk flask equipped with a magnetic stir bar and capped with a septum was charged with 100 mg of 2,3-bis(2,6-dimethylphenylimino)-4-methylmorpholine and 84 mg of (1,2-dimethoxyethane)nickel(II) dibromide under an inert atmosphere. Dry, deoxygenated dichloromethane (5 mL) was added and the mixture was stirred under an argon atmosphere for 1 hour, after which another 5 mL dichloromethane was added. After 16 hours, the mixture was diluted with 10 mL hexane, and the supernatent was removed via a filter paper tipped cannula, and the residue was dried in vacuo to obtain 139 mg green crystals.

Example 31
Reaction of 1,3-bis-(2,6-dimethyl-phenyl)-4,5-bis-(2,6-dimethylphenylimino)-imidazolidin-2-one, (1,2-dimethoxyethane)nickel(II) dibromide, and silver tetrafluoroborate.

In an argon filled glove box, a flame-dried Schlenk flask equipped with a magnetic stir bar was charged with 159.6 mg of 1,3-bis-(2,6-dimethylphenyl)-4,5-bis-(2,6-dimethylphenylimino)-imidazolidin-2-one and 92.7 mg of (1,2-dimethoxyethane)nickel(II) dibromide and 59.4 mg silver tetrafluoroborate. The flask was wrapped in aluminum foil, and on the Schlenk line, under an argon atmosphere, 10 mL dry tetrahydrofuran was added. A white precipitate immediately separated. The mixture was stirred for 25 min, then the supernatant was transferred via filter paper-tipped cannula to a dry septum-capped vial. The supernatant was concentrated to dryness under a stream of dry argon for 16 h to afford 256 mg of a yellow crystalline powder.

Example 32
Preparation of the nickel dibromide complex of 1,3-bis(4-methoxy-2,6-dimethylphenyl)-4,5-bis(4-methoxy-2,6-dimethylphenylimino)imidazolidin-2-one.

A 50 mL Schlenk flask equipped with a magnetic stir bar and capped with a septum was charged with 101 mg of 1,3-bis(4-methoxy-2,6-dimethylphenyl)-4,5-bis(4-methoxy-2,6-dimethylphenylimino)imidazolidin-2-one and 40 mg of (1,2-dimethoxyethane)nickel(II) dibromide under an inert atmosphere. Dry, deoxygenated dichloromethane (10 mL) was added and the mixture was stirred under an nitrogen atmosphere, slowly turning dark red-brown over 3 hours. After 2 more hours, the supernatant was removed to a flame-dried Schlenk flask via a filter paper-tipped cannula, diluted with 10 mL dry, deoxygenated hexane, and concentrated to dryness under a stream of nitrogen to give a mixture of a tan microcrystalline powder and large, well-defined dark brown crystals. The latter were separated and used without further purification.

Example 33
Preparation of the nickel dibromide complex of 1,4-dimethyl-2,3-bis(2,6-dimethylphenylimino)piperazine.

A 50 mL Schlenk flask equipped with a magnetic stir bar and capped with a septum was charged with 48 mg of 1,4-dimethyl-2,3-bis(2,6-dimethylphenylimino)piperazine and 35 mg of (1,2-dimethoxyethane)nickel(II) dibromide under an inert atmosphere. Dry, deoxygenated dichloromethane (5 mL) was added and the mixture was stirred under an argon atmosphere, turning green within about 5 minutes and slowly producing a green precipitate. After a total of 7 hours, the volatiles were removed under reduced pressure (1 mm Hg) and the residue was washed with 2×5 mL of dry, deoxygenated diethyl ether. The resultant green solid was dried under reduced pressure (1 mm Hg).

Example 34

Synthesis of:

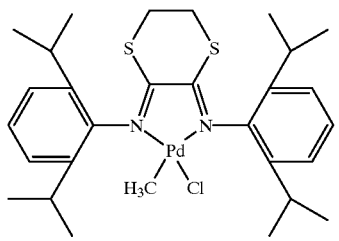

In the glove box, a Schlenk flask was charged with 500 mg of 2,3-bis(2,6-diisopropylphenylimino)-[1,4]dithiane and 250 mg (1,5-cyclooctadiene)palladium methyl chloride. The flask was removed form the box and placed under an argon atmosphere. To the solid mixture was added 20 ml of methylene chloride resulting in an orange solution. The mixture was left to stir for 4 hours. After 4 hours, 20 ml of hexane was added resulting in the precipitation of an orange solid. The solvent was removed via filter cannula leaving a red/orange solid. The solid was subsequently washed 3×10 ml of hexane and dried in vacuo resulting in 490 mg of the complex (83 % yield). $^1$H NMR is consistent with the proposed structure.

Example 35

Synthesis of:

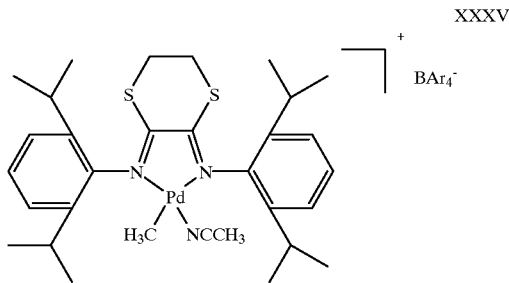

XXXV

In the glove box, a Schlenk flask was charged with 490 mg of 2,3-bis(2,6-diisopropylphenylimino)[1,4]dithiane palladium methyl chloride and 738 mg of NaBAr$_4$ where Ar=3,5-bis-trifluromethylphenyl. The flask was removed form the box and placed under an argon atmosphere. To the solid mixture was added 25 ml of methylene chloride and 0.2 ml of acetonitrile resulting in an orange solution. The mixture was left to stir for 3 hours. After 3 hours, the solution was transfered via filter cannula leaving a gray solid (NaCl). The solvent was subsequently removed in vacuo resulting in a orange glass (1. 1 g of the complex, 90 % yield). $^1$H NMR is consistent with the proposed structure.

Example 36

Polymerization of ethylene with the nickel dibromide complex of 2,3-bis(2,6-dimethylphenylimino)-[1,4]dithiane in the presence of MAO.

A 200 mL pear-shaped Schlenk flask equipped with a magnetic stir bar and capped with a septum was charged with 5.3 mg of the nickel dibromide complex of 2,3-bis(2,6-dimethylphenylimino)-[1,4]dithiane. The flask was evacuated and refilled with ethylene, then charged with 75 mL of dry, deoxygenated toluene. The resultant suspension was cooled to 0° C. and allowed to equilibrate with 1 atmosphere ethylene for 15 minutes, then treated with 4.0 mL of a 10 wt % solution of MAO in toluene and stirred under 1 atmosphere ethylene. A white polyethylene precipitate (with a faint red-brown tinge) was observed within minutes. After 10 minutes, the mixture was quenched by the addition of acetone (50 mL), methanol (50 mL) and 6 N aqueous HCl (100 mL). The swollen polyethylene which separated was isolated by vacuum filtration and washed with water, methanol and acetone, then dried under reduced pressure (0.05–0.1 mm Hg) for 48 hours to give 2.5 g of a white polyethylene. A similar reaction at 21.5° C. using 0.104 mg of the nickel complex (100 µL of a 1.04 mg/mL stock solution in o-difluorobenzene) gave 426 mg polyethylene after 14 minutes reaction (359,000 Turnovers per hour (TO/h)). $^1$H NMR: 24 branches/1000 carbon atoms. GPC: $M_n$=810,000; $M_w/M_n$=2.3.

Example 37

Polymerization of ethylene using a catalyst generated in situ from 2,3-bis(2,6-dimethylphenylimino)-[1,4]dithiane, bis(1,5-cyclooctadiene)nickel(0) and HB(Ar)$_4$ (Ar=3,5-bis (trifluoromethyl)phenyl).

A 250 mL pear-shaped Schlenk flask equipped with a magnetic stir bar and capped with a septum was charged with 20 mg of bis(1,5-cyclooctadiene)nickel(0), 33 mg of 2,3-bis(2,6-dimethylphenylimino)-[1,4]dithiane, and 83 mg of the ether solvate HB(Ar)$_4$. The flask was evacuated and refilled with ethylene, then charged with 75 mL of dry, deoxygenated toluene. The deep violet solution which resulted was stirred under ethylene at 25° C. for 30 minutes, then quenched by addition of acetone (50 mL), and methanol (50 mL). The polyethylene which separated was isolated by vacuum filtration and washed with acetone, then dried under reduced pressure (0.5 mm Hg) for 18 hours to give 339 mg of white polyethylene (332 TO/h). $^1$H NMR: 47 branches/1000 carbon atoms. GPC: $M_n$=180,000; $M_w.M_n$=2.4.

Example 38

Polymerization of ethylene with the nickel dibromide complex of 2,3-bis(2,6-dimethylphenylimino)-[1,4]dithiane in the presence of MAO.

A 200 mL pear-shaped Schlenk flask equipped with a magnetic stir bar was charged with 0.5 mL of a stock solution (10 mg in 10 mL CH$_2$Cl$_2$) of the nickel dibromide complex of 2,3-bis(2,6-dimethylphenylimino)-[1,4] dithiane. The flask was evacuated and refilled with ethylene, and charged with 75 mL of dry, deoxygenated toluene. The reaction flask was placed in a water bath (23° C.) and treated with 1.0 mL of a 10 wt % solution of MAO in toluene and stirred under 1 atmosphere ethylene. A white polyethylene precipitate was observed within seconds. After 5 minutes, the mixture was quenched by the addition of acetone, methanol and 6 N aqueous HCl. The swollen polyethylene which separated was isolated by vacuum filtration and washed with acetone. The resulting polymer was dried for several hours in a vacuum oven at 80° C. 580 mg of a white rubbery solid was isolated (285,000 TO/h). DSC: (2nd heat)

broad melt with an endothermic maximum at 87° C. $^1$H NMR, 37 branches/1000 carbon atoms. GPC: $M_n$=186,000; $M_w/M_n$=2.06.

Example 39

Polymerization of ethylene with the nickel dibromide complex of 2,3-bis(2,6-diisopropylphenylimino)-[1,4]dithiane in the presence of MAO.

A 200 mL pear-shaped Schienk flask equipped with a magnetic stir bar was charged with 0.5 mL of a stock solution (10 mg in 10 mL $CH_2Cl_2$) of the nickel dibromide complex of 2,3-bis(2,6-diisopropylphenylimino)-[1,4]dithiane. The flask was evacuated and refilled with ethylene, and charged with 75 mL of dry, deoxygenated toluene. The reaction flask was placed in a water bath and treated with 1.0 mL of a 10 wt % solution of MAO in toluene and stirred under 1 atmosphere ethylene. After 10 minutes, the mixture was quenched by the addition of acetone, methanol and 6 N aqueous HCl. The swollen polyethylene which separated was isolated by vacuum filtration and washed with acetone. The resulting polymer was dried for several hours in a vacuum oven at 80° C. 210 mg of a white rubbery amorphous polymer was isolated (63,000 TO/h). DSC: (2nd heat) broad melt with an endothermic maximum at 6° C. $^1$H NMR: 92 branches/1000 carbon atoms. GPC: $M_n$=146,000; $M_w/M_n$=1.85.

Example 40

Polymerization of ethylene with the nickel dibromide complex of 2,3-bis(2,6-dimethylphenylimino)-[1,4]dithiane in the presence of MMAO (modified methylaluminoxane; 23 % iso-butylaluminoxane).

A 600 mL Parr® autoclave was first heated to about 100° C. under high vacuum to ensure that the reactor was dry. The reactor was cooled and purged with argon. Under an argon atmosphere, the autoclave was charged with 150 mL of toluene and 0.3 mL of a stock solution (10 mg in 10 mL $CH_2Cl_2$) of the nickel dibromide complex of 2.3-bis(2,6-dimethylphenylimino)-[1,4]dithiane. The autoclave was heated to 40° C. and 2 mL of MMAO in heptane (6.42 wt % aluminum) was added. The reactor was rapidly pressurized to 100 psig with ethylene and the temperature ramped up to 50° C. After 10 minutes at 50° C., the reaction was quenched by the addition of acetone, and methanol. The swollen polyethylene which separated was isolated and dried for several hours in a vacuum oven at 80° C. 4.8 g of a white rubbery solid was isolated (2,000,000 TO/h). DSC: (2nd heat) broad melt with an endothermic maximum at 97° C. $^1$H NMR: 28 branches/1000 carbon atoms. GPC: $M_n$=155,000; $M_w/M_n$=2.10.

Example 41

Polymerization of ethylene with the nickel dibromide complex of 2,3-bis(2,6-dimethylphenylimino)-[1,4]dithiane in the presence of MMAO (23 % iso-butylaluminoxane).

A 600 mL Parr® autoclave was first heated to about 100° C. under high vacuum to ensure that the reactor was dry. The reactor was cooled and purged with argon. Under an argon atmosphere, the autoclave was charged with 150 mL of toluene and 0.3 mL of a stock solution (10 mg in 10 mL $CH_2Cl_2$) of the nickel dibromide complex of 2,3-bis(2,6-dimethylphenylimino)-[1,4]dithiane. The autoclave was cooled to 15° C. and 2 mL of MMAO in heptane (6.42 wt % aluminum) was added. The reactor was rapidly pressurized to 100 psig with ethylene and the temperature ramped up to 25° C. After 10 minutes at 25° C., the reaction was quenched by the addition of acetone, and methanol. The swollen polyethylene which separated was isolated and dried for several hours in a vacuum oven at 80° C. 4.4 g of a white rubbery polyethylene was isolated (1,800,000 TO/h). DSC: (2nd heat) melt with an endothermic maximum at 125° C. $^1$H NMR: 6 branches/1000 carbon atoms. GPC: $M_n$=598,000; $M_w/M_n$=2.12.

Example 42

Polymerization of ethylene with the nickel dibromide complex of 2,3-bis(2,6-dimethylphenylimino)-[1,4]dithiane in the presence of MMAO (23 % iso-butylaluminoxane).

A 600 mL Parr® autoclave was first heated to about 100° C. under high vacuum to ensure that the reactor was dry. The reactor was cooled and purged with argon. Under an argon atmosphere, the autoclave was charged with 150 mL of toluene and 1.0 mL of a stock solution (10 mg in 10 mL $CH_2Cl_2$) of the nickel dibromide complex of 2,3-bis(2,6-dimethylphenylimino)-[1,4]dithiane. The autoclave was heated to 55° C. and 2 mL of MMAO in heptane (6.42 wt % aluminum) was added. The reactor was rapidly pressurized to 100 psig with ethylene and the temperature ramped up to 65° C. After 10 minutes at 65° C., the reaction was quenched by the addition of acetone, and methanol. The swollen polyethylene which separated was isolated and dried for several hours in a vacuum oven at 80° C. 5.3 g of a white rubbery solid was isolated (640,000 TO/h). DSC: (2nd heat) melt with an endothermic maximum at 78° C. $^1$H NMR: 47 branches/1000 carbon atoms. GPC: $M_n$=86,000; $M_w/M_n$=1.95.

Example 43

Polymerization of ethylene with the nickel dibromide complex of 2,3-bis(2,6-dimethylphenylimino)-[1,4]dithiane in the presence of MMAO (23 % iso-butylaluminoxane).

A 600 mL Parr® autoclave was first heated to about 100° C. under high vacuum to ensure that the reactor was dry. The reactor was cooled and purged with argon. Under an argon atmosphere, the autoclave was charged with 150 mL of toluene and 1.0 mL of a stock solution (10 mg in 10 mL $CH_2Cl_2$) of the nickel dibromide complex of 2,3-bis(2,6-dimethylphenylimino)-[1,4]dithiane. The autoclave was heated to 70° C. and 2 mL of MMAO in heptane (6.42 wt % aluminum) was added. The reactor was rapidly pressurized to 100 psig with ethylene and the temperature ramped up to 80° C. After 10 minutes at 80° C., the reaction was quenched by the addition of acetone, and methanol. The swollen polyethylene which separated was isolated and dried for several hours in a vacuum oven at 80° C. 3.5 g of a white rubbery solid was isolated (440,000 TO/h). DSC: (2nd heat) melt with an endothermic maximum at 67° C. $^1$H NMR: 53 branches/1000 carbon atoms. GPC: $M_n$=87,000; $M_w/M_n$=1.66.

Example 44

Polymerization of ethylene with the nickel dibromide complex of 2,3-bis(2,6-diisopropylphenylimino)-[1,4]dithiane in the presence of MMAO (23 % iso-butylaluminoxane).

A 600 mL Parr® autoclave was first heated to about 100° C. under high vacuum to ensure that the reactor was dry. The reactor was cooled and purged with argon. Under an argon atmosphere, the autoclave was charged with 150 mL of toluene and 0.5 mL of a stock solution (10 mg in 10 mL $CH_2Cl_2$) of the nickel dibromide complex of 2,3-bis(2,6-diisopropylphenylimino)-[1,4]dithiane. The autoclave was heated to 40° C. and 2 mL of MMAO in heptane (6.42 wt % aluminum) was added. The reactor was rapidly pressurized to 100 psig with ethylene and the temperature ramped up to 50° C. After 10 minutes at 50° C., the reaction was quenched by the addition of acetone, and methanol. The swollen polyethylene which separated was isolated and dried for several hours in a vacuum oven at 80° C. 2.4 g of a white rubbery solid was isolated (700,000 TO/h). DSC: (2nd heat) melt with an endothermic maximum at 46° C. 1 H NMR: 75 branches/1000 carbon atoms. GPC: $M_n$=966,000; $M_w/M_n$=1.70.

Example 45
Polymerization of ethylene with the nickel dibromide complex of 2,3-bis(2,6-diisopropylphenylimino)-[1,4]dithiane in the presence of MMAO (23 % iso-butylaluminoxane.

The procedure described in example 44 was followed except the polymerization was conducted at 80° C. 1.4 g of a white rubbery solid was isolated (400,000 TO/h). DSC: (2nd heat) melt with an endothermic maximum at 0° C. $^1$H NMR: 95 branches/1000 carbon atoms. GPC: $M_n$=406,000; $M_w/M_n$=2.05.

Example 46
Polymerization of ethylene with the nickel dibromide complex of 2,3-bis(2,6-diisopropylphenylimino)-[1,4]dithiane in the presence of MMAO (23 % iso-butylaluminoxane).

The procedure described in Example 44 was followed except the polymerization was conducted at 65° C. 2.15 g of a white rubbery solid was isolated (630,000 TO/h). DSC: (2nd heat) melt with an endothermic maximum at 15° C. $^1$H NMR: 89 branches/1000 carbon atoms. GPC: $M_n$=502,000; $M_w/M_n$=1.78.

Example 47
Polymerization of ethylene with the nickel dibromide complex of 2,3-bis(2,6-diisopropylphenylimino)-[1,4]dithiane in the presence of MMAO(23 % iso-butylaluminoxane.

The procedure described in Example 44 was followed except the polymerization was conducted at 25° C. 1.9 g of a white rubbery solid was isolated (560,000 TO/h). DSC: (2nd heat) melt with an endothermic maximum at 90° C. $^1$H NMR: 33 branches/1000 carbon atoms. GPC: $M_n$=839,000; $M_w/M_n$=1.37.

Example 48
Oligomerization of ethylene to α-olefin with the nickel dibromide complex of 2,3-bis(phenylimino)-[1,4]dithiane in the presence of MAO.

A 1 L Fischer-Porter bottle was assembled onto a pressure head equipped with a mechanical stirrer and gas and liquid feed-through ports, then pressurized to 75 psig of ethylene and relieved to ambient pressure seven times. The bottle was immersed in a 21.5° C. water bath, then 50 mL of dry, deoxygenated toluene was added via syringe, followed by 100 µL of a stock solution of 15.3 mg of the nickel dibromide complex of 2,3-bis(phenylimino)-[1,4]dithiane in 15.0 mL of dichloromethane, followed by another 50 mL of toluene. The mixture was stirred at 300 rpm under 75 psig ethylene for 5 minutes to saturate the solution with ethylene, then the pressure was relieved, and 4.0 mL of a 10 wt % solution of MAO in toluene was quickly added. The flask was immediately re-pressurized to 75 psig ethylene and stirred at 300 rpm. After 30 minutes, the pressure was relieved and the reaction quenched by addition of 10 mL of methanol. After disassembling the apparatus, another 40 mL of methanol, 50 mL of 6 N aqueous HCl, and 10 mL acetone were added and the mixture was stirred to complete hydrolysis of the MAO. The resultant organic layer was separated, washed with 6 N aqueous HCl (1×25 mL), and water (2×50 mL), then concentrated under reduced pressure (15 Torr) at 40° C. to obtain an oil. This was treated with toluene (50 mL) and re-concentrated twice, then treated with acetone (50 mL) and re-concentrated, to obtain a waxy white polyethylene solid. Drying in vacuo at 100° C., 250 mm Hg for 14 hours gave 0.180 g of polymer, approximate $M_n$=517, containing approximately 85% α-olefin and 15% internal olefin.

Example 49
Polymerization of ethylene with the nickel dibromide complex of 2,3-bis(2,6-dimethylphenylimino)-2,3-dihydrobenzo [1,4]dithiine in the presence of MAO.

A 200 mL pear-shaped Schlenk flask equipped with a magnetic stir bar and capped with a septum was charged with 100 mL of dry, deoxygenated toluene. The flask was placed in a water bath and allowed to equilibrate with 1 atmosphere ethylene for 10 minutes, then 0.25 mL of a stock solution prepared from 10.2 mg of the nickel dibromide complex of 2,3-bis-(2,6-dimethylphenylimino)-2,3-dihydrobenzo[1,4]dithiine in 13.11 g dry, deoxygentated dichloromethane was added. The reaction mixture was then treated with 4.0 mL of a 10 wt % solution of MAO in toluene and stirred under 1 atmosphere ethylene. Ethylene uptake and formation of a polyethylene precipitate were observed. After 6.5 minutes, the mixture was quenched by the addition of acetone (50 mL), methanol (50 mL) and 6 N aqueous HCl (100 mL). The swollen polyethylene which separated was isolated by vacuum filtration, then dried at 80° C. in vacuo for several hours. 287 mg of a white powdery polyethylene was isolated (236,000 TO/h). DSC: (2nd heat) melt with an endothermic maximum at 88° C. $^1$H NMR showed this material to contain approximately 36 branches/1000 carbon atoms. GPC: $M_n$=145,000; $M_w/M_n$=2.35.

Example 50
Polymerization of ethylene using a catalyst formed in situ from 2.3-bis(2,6-diisopropylphenylimino)-[1,4]dithiane and $[Pd(NCCH_3)_4][F_4]^2$.

A 200 mL pear-shaped Schlenk flask equipped with a magnetic stir bar and capped with a septum was charged with 0.022 g of 2,3-bis(2,6-diisopropylphenylimino)-[1,4]dithiane and 0.019 g $[Pd(NCCH_3)_4][BF_4]_2$. The flask was evacuated and refilled with ethylene, then 100 mL of dry, deoxygenated dichloromethane was added via syringe and the resultant mixture was stirred under 1 atmosphere of ethylene at 25° C. Very little ethylene uptake was observed. After 10 minutes, 0.412 g $B(C_6F_5)_3$ was added, resulting in an increased rate of ethylene uptake. After a total of 84 minutes, the reaction was worked up by evaporating the dichloromethane under a stream of nitrogen, washing the residue with methanol repeatedly to extract the $B(C_6F_5)_3$, and drying the residue in vacuo to obtain 0.57 g of amorphous polyethylene, approximate $M_n$=17,000; $M_n/M_w$=1.3. $^1$H NMR showed approximately 105 branches per 1000 carbons.

Example 51
Polymerization of ethylene with the nickel dibromide complex of 2,3-bis(4-methoxy-2,6-dimethylphenylimino)-[1,4] dithiane in the presence of MAO.

A 500 mL round bottom flask fitted with a Schlenk adapter and equipped with a magnetic stir bar and capped with a septum was evacuated, flame-dried, then refilled with ethylene. The flask was provided with a room temperature (ca. 23° C.) water bath, then charged with 100 mL of dry, deoxygenated toluene and allowed to equilibrate with 1 atmosphere ethylene for 30 minutes. The reaction mixture was then treated with 4.0 mL of a 10 wt % solution of MAO in toluene and stirred under 1 atmosphere ethylene, then 0.10 mL of a stock solution (prepared from 6.3 mg of the nickel dibromide complex of 2,3-bis(4-methoxy-2,6-dimethylphenylimino)-[1,4]dithiane and 6.5 mL dichloromethane) was added. After 10 minutes, the reaction mixture was quenched by the addition of acetone, methanol and 6 N aqueous HCl. The polyethylene which separated was isolated by vacuum filtration and washed with water, methanol and acetone, dried on the filter for 2 h, then further dried 13 days in a vacuum oven at 80° C. 182 mg of a white polyethylene was isolated (254,000 TO/h). DSC: (2nd heat) melt with an endothermic maximum at 124° C. $^1$H NMR: 13 branches/1000 carbon atoms. GPC: $M_n$=145,600; $M_w/M_n$=2.6.

Example 52
Polymerization of ethylene with the nickel dibromide complex of 2,3-bis(2,6-diisopropylphenylimino)-[1,4]dithiane in the presence of (CH$_3$CH$_2$AlCl.

A 600 mL Parr® autoclave was first heated to about 100° C. under high vacuum to ensure the reactor was dry. The reactor was cooled and purged with argon. Under an argon atmosphere, the autoclave was charged with 150 mL of toluene and 0.5 mL of a stock solution (10 mg in 10 mL CH$_2$Cl$_2$) of the nickel dibromide complex of 2,3-bis(2,6-diisopropylphenylimino)-[1,4]dithiane. The autoclave was heated to 45° C. and 2 mL of (CH$_3$CH$_2$)$_2$AlCl (5000 equiv.) in toluene was added. The reactor was rapidly pressurized to 100 psig and the temperature ramped up to 50° C. After 10 minutes at 50° C., the reaction was quenched by the addition of acetone, and methanol. The swollen polyethylene which separated was isolated by filtration and dried for several hours in a vacuum oven at 80° C. resulting in 1.9 g of a white rubbery solid (560,000 TO/h). DSC: (2nd heat) broad melt with an endothermic maximum at 30° C. $^1$H NMR: 87 branches/1000 carbon atoms. GPC: $M_n$=557,000; $M_w/M_n$=1.82.

Example 53
Polymerization of ethylene with the nickel dibromide complex of 2,3-bis(2,6-diisopropylphenylimino)-[1,4]dithiane in the presence of (CH$_3$CH$_2$AlCl A 600 mL Parr® autoclave was first heated to about 100° C. under high vacuum to ensure the reactor was dry. The reactor was cooled and purged with argon. Under an argon atmosphere, the autoclave was charged with 150 mL of toluene and 0.5 mL of a stock solution (10 mg in 10 mL CH$_2$Cl$_2$) of the nickel dibromide complex of 2,3-bis(2,6-diisopropylphenylimino)-[1,4]dithiane. The autoclave was heated to 45° C. and 0.2 mL of (CH$_3$CH$_2$)$_2$AlCl (500 equiv.) in toluene was added. The reactor was rapidly pressurized to 100 psig and the temperature ramped up to 50° C. After 10 minutes at 50° C. the reaction was quenched by the addition of acetone, and methanol. The swollen polyethylene which separated was isolated by filtration and dried for several hours in a vacuum oven at 80° C. resulting in 2 g of a white rubbery solid (590,000 TO/h). DSC: (2nd heat) broad melt with an endothermic maximum at 30° C. $^1$H NMR: 85 branches/1000 carbon atoms. GPC: $M_n$=515,000; $M_w/M_n$=1.81.

Example 54
Polymerization of ethylene with the nickel dibromide complex of 2,3-bis(2,6-diisopropylphenylimino)-[1,4]dithiane in the presence of (CH$_3$CH$_2$AlCl A 600 mL Parr® autoclave was first heated to about 100° C. under high vacuum to ensure the reactor was dry. The reactor was cooled and purged with argon. Under an argon atmosphere, the autoclave was charged with 150 mL of toluene and 0.5 mL of a stock solution (10 mg in 10 mL CH$_2$Cl$_2$) of the nickel dibromide complex of 2,3-bis(2,6-diisopropylphenylimino)-[1,4]dithiane. The autoclave was heated to 45° C. and 0.04 mL of (CH$_3$CH$_2$)$_2$AlCl (100 equiv.) in toluene was added. The reactor was rapidly pressurized to 100 psig and the temperature ramped up to 50° C. After 10 minutes at 50° C., the reaction was quenched by the addition of acetone, and methanol. The swollen polyethylene which separated was isolated by filtration and dried for several hours in a vacuum oven at 80° C. resulting in 1.5 g of a white rubbery solid (440,000 TO/h). DSC: (2nd heat) broad melt with an endothermic maximum at 29° C. $^1$H NMR: 80 branches/1000 carbon atoms. GPC: $M_n$=422,000; $M_w/M_n$=1.97.

Example 55
Copolymerization of ethylene and ethyl undecenoate with the nickel dibromide complex of 2,3-bis(2,6-dimethylphenylimino)-[1,4]dithiane in the presence of MMAO (23 % iso-butylaluminoxane).

A flame dried Schlenk flask equipped with a stir bar and a rubber septum was charged with 50 ml of toluene and 5 mg of the nickel dibromide complex of 2,3-bis(2,6-dimethylphenylimino)-[1,4]dithiane. The flask was cooled to 0° C. in an ice-water bath and filled with ethylene (1 atmosphere). To the flask was added 2.0 ml of MMAO in heptane (6.42 wt % aluminum). Within 5 seconds, 5 ml of ethyl undecenoate was added to give a purple solution. The mixture was left to stir for 16 hours. Acetone, methanol and 6M HCl were added to quench the reaction and precipitate the polymer. The polymer was collected by suction filtration and washed with copious amounts of acetone to ensure all of the ethyl undecenoate comonomer was removed resulting in 100 mg of white powdery polymer. NMR spectroscopic analysis is consistent with the preparation of an ester group containing copolymer. In addition, ethylene homopolymer, which resulted from the short reaction time prior to addition of the ethyl undecenoate, was present. $^1$H NMR: 7.5 wt % ethyl undecenoate incorporated. GPC: $M_n$=9500, $M_w/M_n$=16.6. DSC: $T_m$=128° C.

Example 56
Co-polymerization of ethylene and 1,13-tetradecadiene with the nickel dibromide complex of 2,3-bis(2,6-dimethylphenylimino)-[1,4]dithiane in the presence of MAO.

A 200 mL pear-shaped Schlenk flask equipped with a magnetic stir bar and capped with a septum was flame-dried under vacuum, refilled with ethylene, and then sequentially charged with 50 mL of dry, deoxygenated toluene, 6.0 mL of deoxygenated 1,13-tetradecadiene, and 1.0 mL of a stock solution of 11.8 mg of the nickel dibromide complex of 2,3-bis(2,6-dimethylphenylimino)-[1,4]dithiane in 10.0 mL of dry, deoxygenated dichloromethane. The flask was placed in a 23° C. water bath and allowed to equilibrate with 1 atmosphere of ethylene for 5 minutes, then 4.0 mL of a 10 wt % solution of MAO in toluene was added and the mixture was stirred under 1 atmosphere of ethylene. Ethylene uptake was observed and the mixture rapidly became more viscous. After 7 minutes, the reaction was quenched by the addition of acetone (50 mL), methanol (50 mL) and 6 N aqueous HCl (100 mL). The co-polymer which separated was isolated by vacuum filtration and dried in vacuo at 100° C. for 24 hours to obtain 0.72 g of a rubbery white polymer, which formed a gel upon attempted re-dissolution in hot o-dichlorobenzene.

Example 57
Polymerization of ethylene with the nickel dibromide complex of 2,3-bis(2,6-dimethylphenylimino)-[1,4]dioxane in the presence of MAO.

A 200 mL pear-shaped Schlenk flask equipped with a magnetic stir bar and capped with a septum was charged with 3.4 mg of the nickel dibromide complex of 2,3-bis(2,6-dimethylphenylimino)-[1,4]dioxane. The flask was evacuated and refilled with ethylene, then charged with 75 mL of dry, deoxygenated toluene. The resultant suspension was cooled to 0° C. and allowed to equilibrate with 1 atmosphere ethylene for 15 minutes, then treated with 4.0 mL of a 10 wt % solution of MAO in toluene and stirred under 1 atmosphere ethylene. A white polyethylene precipitate (with a faint yellow-orange tinge) was observed within minutes. After 38 minutes, the mixture was quenched by the addition of acetone (50 mL), methanol (50 mL) and 6 N aqueous HCl (100 mL). The swollen polyethylene that separated was isolated by vacuum filtration and washed with water, methanol and acetone, then dried under reduced pressure (0.05–0.1 mm Hg) for 18 hours to give 6.0 g of a white polyethylene (54,000 TO/h). $^1$H NMR: 19 branches/1000 carbon atoms. GPC: $M_n$=504,000; $M_w/M_n$=2.3.

Example 58
Polymerization of ethylene with the nickel dibromide complex of 2,3-bis(benzyloxymethyl)-5,6-bis(2,6-dimethylphenylimino)-[1,4]dioxane in the presence of MAO.

A 500 mL round bottom flask was fitted with a Schlenk adapter and equipped with a magnetic stir bar and capped with a septum was charged with 100 mL of dry, deoxygenated toluene. The flask was placed in a water bath and allowed to equilibrate with 1 atmosphere ethylene for 19 minutes, then 0.25 mL of a stock solution prepared from 10.0 mg of the nickel dibromide complex of 2,3-bis(benzyloxymethyl)-5,6-bis(2,6-dimethylphenylimino)-[1,4]dioxane and 10.0 mL dichloromethane was added. The reaction mixture was then treated with 4.0 mL of a 10 wt % solution of MAO in toluene and stirred under 1 atmosphere ethylene. Ethylene uptake and formation of a polyethylene precipitate were observed. After 6.5 minutes, the mixture was quenched by the addition of acetone, methanol and 6 N aqueous HCl. The swollen polyethylene which separated was isolated by vacuum filtration, then dried at 80° C. in vacuo for several hours. 392 mg of white polyethylene was isolated (404,000 TO/h). DSC: (2nd heat) melt with an endothermic maximum at 12° C. $^1$H NMR: 16 branches/1000 carbon atoms. GPC: $M_n$=125,000; $M_w/M_n$=2.8.

Example 59
Polymerization of ethylene with the nickel dibromide complex of 5-methoxymethyl-2,3-bis(2,6-dimethylphenylimino)-[1,4]dioxane in the presence of MAO.

A 200 mL pear-shaped Schlenk flask equipped with a magnetic stir bar and capped with a septum was charged with 3.8 mg of the nickel dibromide complex of 5-methoxymethyl-2,3-bis(2,6-dimethylphenylimino)-[1,4]dioxane. The flask was evacuated and refilled with ethylene, then charged with 75 mL of dry, deoxygenated toluene. The resultant suspension was cooled to 0° C. and allowed to equilibrate with 1 atmosphere ethylene for 15 minutes, then treated with 4.0 mL of a 10 wt % solution of MAO in toluene and stirred under 1 atmosphere ethylene. After 10 minutes, the mixture was quenched by the addition of acetone (50 mL), methanol (50 mL) and 6 N aqueous HCl (100 mL). The swollen polyethylene which separated was isolated by vacuum filtration and washed with water, methanol and acetone, then dried under reduced pressure (0.05–0.1 mm Hg) for 48 hours to give 1.04 g of a white, powdery polyethylene. A similar reaction, also at 0° C., was conducted using 0.655 g (equivalent to 0.57 mg of the nickel complex) of a stock solution of 11.6 mg nickel dibromide complex of 5-methoxymethyl-2,3-bis-(2,6-dimethylphenylimino)-[1,4]dioxane in 13.238 g dichloromethane to obtain 291 mg white, powdery polyethylene after 15 minutes reaction.

Example 60
Polymerization of ethylene with the nickel dibromide complex of 2,3-bis(2,6-dimethylphenylimino)-[1,4]dioxane in the presence of MMAO (23 % iso-butylaluminoxane).

A 600 mL Parr® autoclave was first heated to about 100° C. under high vacuum to ensure the reactor was dry. The reactor was cooled and purged with argon. Under an argon atmosphere, the autoclave was charged with 150 mL of toluene and 0.3 mL of a stock solution (10 mg in 10 mL $CH_2Cl_2$) of the nickel dibromide complex of 2,3-bis(2,6-dimethylphenylimino)-[1,4]dioxane. The autoclave was heated to 60° C. and 2 mL of MMAO in heptane (6.42 wt % aluminum) was added. The reactor was rapidly pressurized to 100 psig and the temperature ramped up to 65 ° C. After 10 minutes at 65° C., the reaction was quenched by the addition of acetone, and methanol. The swollen polyethylene which separated was isolated by filtration and dried for several hours in a vacuum oven at 80° C. 1.3 g of a white rubbery solid was isolated (480,000 TO/h). DSC: (2nd heat) melt with an endothermic maximum at 76° C. $^1$H NMR: 33 branches/1000 carbon atoms. GPC: $M_n$=42,000; $M_w/M_n$=1.82.

Example 61
Polymerization of ethylene with the nickel dibromide complex of 2,3-bis(2,6-dimethylphenylimino)-[1,4]dioxane in the presence of MMAO (23 % iso-butylaluminoxane).

The procedure described in example 60 was followed except the polymerization was conducted at 25° C. resulting in 0.59 g of polyethylene (226,000 TO/h). DSC: (2nd heat) melt with an endothermic maximum at 125° C. $^1$H NMR: 9 branches/1000 carbon atoms. GPC: $M_n$=237,000; $M_w/M_n$=2.15.

Example 62
Polymerization of ethylene with the nickel dibromide complex of 2,3-bis(2,6-dimethylphenylimino)-[1,4]dioxane in the presence of MMAO (23 % iso-butylaluminoxane).

The procedure described in example 60 was followed except the polymerization was conducted at 80° C. resulting in 0.29 g of polyethylene (110,000 TO/h). $^1$H NMR: 69 branches/1000 carbon atoms. GPC: $M_n$=23,000; $M_w/M_n$=1.65.

Example 63
Polymerization of ethylene with the nickel dibromide complex of 2,3-bis(2,6-dimethylphenylimino)-[1,4]dioxane in the presence of MMAO (23 % iso-butylaluminoxane).

The procedure described in example 60 was followed except the polymerization was conducted at 50° C. resulting in 3.1 g of polyethylene (1,200,000 TO/h). DSC: (2nd heat) melt with an endothermic maximum at 95° C. $^1$H NMR: 48 branches/1000 carbon atoms. GPC: $M_n$=63,000; $M_w/M_n$=1.92.

Example 64
Polymerization of ethylene with the nickel dibromide complex of 2,3-bis(2,6-diisopropylphenylimino)-[1,4]dioxane in the presence of MMAO (23 % iso-butylaluminoxane).

A 600 mL Parr® autoclave was first heated to about 100° C. under high vacuum to ensure the reactor was dry. The reactor was cooled and purged with argon. Under an argon atmosphere, the autoclave was charged with 150 mL of toluene and 0.5 mL of a stock solution (10 mg in 10 mL $CH_2Cl_2$) of the nickel dibromide complex of 2,3-bis(2,6-diisopropylphenylimino)-[1,4]dioxane. The autoclave was heated to 60° C. and 2 mL of MMAO in heptane (6.42 wt % aluminum) was added. The reactor was rapidly pressurized to 100 psig and the temperature ramped up to 65° C. After 10 minutes at 65° C., the reaction was quenched by the addition of acetone, and methanol. The swollen polyethylene which separated was isolated by filtration and dried for several hours in a vacuum oven at 80° C. 2.5 g of a white rubbery solid was isolated (660,000 TO/h). DSC: (2nd heat) broad melt with an endothermic maximum at 30° C. $^1H$ NMR: 82 branches/1000 carbon atoms. GPC: $M_n$=147,000; $M_w/M_n$=1.91.

Example 65

Polymerization of ethylene with the nickel dibromide complex of 2,3-bis(2,6-diisopropylphenylimino)-[1,4]dioxane in the presence of MMAO (23 % iso-butylaluminoxane).

The procedure described in example 64 was followed except the polymerization was conducted at 50° C. resulting in 3.4 g of polyethylene (900,000 TO/h). DSC: (2nd heat) melt with an endothermic maximum at 50° C. $^1H$ NMR: 65 branches/1000 carbon atoms. GPC: $M_n$=219,000; $M_w/M_n$=1.85.

Example 66

Polymerization of ethylene with the nickel dibromide complex of 2,3-bis(2,6-diisopropylphenylimino)-[1,4]dioxane in the presence of MMAO (23 % iso-butylaluminoxane).

The procedure described in example 64 was followed except the polymerization was conducted at 25° C. resulting in 1.22 g of polyethylene (320,000 TO/h). DSC: (2nd heat) melt with an endothermic maximum at 112° C. $^1H$ NMR: 17 branches/1000 carbon atoms. GPC: $M_n$=476,000; $M_w/M_n$=2.02.

Example 67

Polymerization of ethylene with the nickel dibromide complex of 2,3-bis(2,6-diisopropylphenylimino)-[1,4]dioxane in the presence of MMAO (23 % iso-butylaluminoxane).

The procedure described in example 64 was followed except the polymerization was conducted at 80° C. resulting in 0.9 g of polyethylene (240,000 TO/h). DSC: (2nd heat) melt with an endothermic maximum at –10° C. $^1H$ NMR: 99 branches/1000 carbon atoms. GPC: $M_n$=98,800; $M_w/M_n$=1.81.

Example 68

Copolymerization of ethylene and ethyl undecenoate with the nickel dibromide complex of 2,3-bis(2,6-dimethylphenylimino)-[1,4]dioxane in the presence of MMAO (23 % iso-butylaluminoxane).

A flame dried Schlenk flask equipped with a stir bar and a rubber septum was charged with 50 ml of toluene and 6 mg of the nickel dibromide complex of 2,3-bis(2,6-dimethylphenylimino)-[1,4]dioxane. The flask was cooled to 0° C. in an ice-water bath and filled with ethylene (1 atmosphere). To the flask was added, 2.0 ml of MMAO in heptane (6.42 wt % aluminum). Within 15 seconds 2.5 ml of ethyl undecenoate was added to give a purple solution. The mixture was left to stir for 16 hours. Acetone, methanol and 6M HCl were added to quench the reaction and precipitate the polymer. The polymer was collected by suction filtration and washed with copious amounts of acetone to ensure all of the ethyl undecenoate comonomer is removed resulting in 510 mg of white powdery polymer. NMR spectroscopic analysis is consistent with the preparation of an ester group containing copolymer. In addition, ethylene homopolymer, which resulted from the short reaction time prior to addition of the ethyl undecenoate, was present. IR: CO stretch at 1742 cm$^-$. $^1H$ NMR: 1.0 wt % ethyl undecenoate incorporated. GPC: $M_n$=61,000, $M_w/M_n$=6.4. DSC: $T_m$=125° C.

Example 69

Polymerization of ethylene with the nickel dibromide complex of 2,3-bis(2,6-diisopropylphenylimino)-4-methylmorpholine in the presence of MAO.

A 1 L Fischer-Porter bottle was assembled onto a pressure head equipped with a mechanical stirrer and gas and liquid feed-through ports, then pressurized to 75 psig of ethylene and relieved to ambient pressure seven times. The bottle was immersed in a 54° C. water bath, then 100 mL of dry, deoxygenated toluene was added via syringe. The mixture was re-pressurized with ethylene at 75 psig and stirred at 300 rpm for 5 minutes to saturate the solution with ethylene, then the pressure was again relieved, and 4.0 mL of a 10 wt % solution of MAO in toluene was quickly added. The apparatus was again re-pressurized to 75 psig ethylene and stirred at 300 rpm for another 5 min to ensure saturation with ethylene. The pressure was once again relieved to ambient pressure and 0.5 mL of a stock solution prepared from 10.0 mg of the nickel dibromide complex of 2,3-bis(2,6-diisopropylphenylimino)-4-methylmorpholine and 10 mL dichloromethane was quickly added and the system quickly pressurized once again with ethylene to 75 psig. After 7 min the pressure was relieved to atmospheric and the reaction was quenched by addition of 5 mL methanol. After the apparatus was disassembled, an additional 50 mL methanol, 50 ml aqueous 6N HCl and 20 mL acetone was added. The resultant organic layer was separated, washed with 6 N aqueous HCl (1×25 mL), and water (2×50 mL), then concentrated by rotary evaporation under reduced pressure (10 Torr) at 40° C. The residue was then treated with toluene (50 mL) and re-concentrated to afford 134 mg of a very rubbery, clear polyethylene (55,000 TO/h). $^1H$ NMR: 134 branches/1000 carbon atoms. GPC: $M_n$=169,000; $M_w/M_n$=1.4.

Example 70

Polymerization of ethylene with the nickel dibromide complex of 2,3-bis(2,6-dimethyl-phenylimino)-4-methylmorpholine in the presence of MMAO.

A 600 mL Parr® autoclave was first heated to about 100° C. under high vacuum to ensure the reactor was dry. The reactor was cooled and purged with argon. Under an argon atmosphere, the autoclave was charged with 150 mL of toluene and 1 mL of a stock solution (10 mg in 20 mL $CH_2Cl_2$) of the nickel dibromide complex of 2,3-bis(2,6-dimethylphenylimino)-4-methylmorpholine. The autoclave was heated to 45° C. and 3 mL of MMAO in heptane (6.42 wt % aluminum) was added. The reactor was rapidly pressurized to 100 psig and the temperature ramped up to 50° C. After 10 minutes at 50° C., the reaction was quenched by the addition of acetone, and methanol. The swollen polyethylene which separated was isolated by filtration and dried for several hours in a vacuum oven at 80° C. resulting in 0.87 g of a white rubbery solid was isolated (138,000 TO/h). $^1H$ NMR: 97 branches/1000 carbon atoms.

Example 71

Polymerization of ethylene with the nickel dibromide complex of 1,3-bis(4-methoxy-2,6-dimethylphenyl)-4,5-bis(4-methoxy-2,6-dimethylphenylimino)imidazolidin-2-one in the presence of MAO.

A 500 mL round bottom flask fitted with a Schlenk adapter and equipped with a magnetic stir bar and capped with a septum was evacuated, flame-dried, then refilled with ethylene. The flask was provided with a room temperature (ca. 23° C.) water bath, then charged with 100 mL of dry, deoxygenated toluene and allowed to equilibrate with 1 atmosphere ethylene for 30 minutes while stirring at 1000 rpm. The reaction mixture was then treated with 4.0 mL of a 10 wt % solution of MAO in toluene and stirred under 1 atmosphere ethylene, then 0.10 mL of a stock solution prepared from 6.0 mg of the nickel dibromide complex of 1,3-bis(4-methoxy-2,6-dimethylphenyl)-4,5-bis(4-methoxy-2,6-dimethylphenylimino)imidazolidin-2-one and 6.0 mL dichloromethane was added. After about 7 min and 20 seconds an additional 0.25 mL of the stock solution was added. After 15 more minutes, the reaction mixture was quenched by the addition of acetone, methanol and 6 N aqueous HCl. The polyethylene which separated was isolated by vacuum filtration and washed with water, methanol and acetone, then dried on the filter for 2 h, then further dried 13 days in a vacuum oven at 80° C. to obtain 172 mg white polyethylene. DSC: (2nd heat) melt with an endothermic maximum at 124° C. $^1$H NMR showed this material to contain approximately 18 branches/1000 carbon atoms. GPC: $M_n$=56,500; $M_w/M_n$=3.55.

Example 72

Polymerization of ethylene with the reaction product of 1,3-bis-(2,6-dimethyl-phenyl)-4,5-bis-(2,6-dimethylphenylimino)-imidazolidin-2-one, (1,2-dimethoxyethane) nickel(II) dibromide, and silver tetrafluoroborate in the presence of MAO.

A 500 mL round bottom flask fitted with a Schlenk adapter, capped with a septum, and equipped with a magnetic stir bar was charged with 100 mL of dry, deoxygenated toluene. The flask was placed in a water bath and allowed to equilibrate with 1 atmosphere ethylene for 10 minutes, then 0.10 mL of a stock solution (freshly prepared from 240 mg of the reaction product of 1,3-bis-(2,6dimethylphenyl)-4,5-bis-(2,6-dimethylphenylimino)-imidazolidin-2-one, (1,2-dimethoxyethane)nickel(II) dibromide, and silver tetrafluoroborate in 10 mL dry, deoxygentated dichloromethane) was added. The reaction mixture was then treated with 4.0 mL of a 10 wt % solution of MAO in toluene and stirred under 1 atmosphere ethylene. Ethylene uptake and formation of a polyethylene precipitate were observed. After 6.33 minutes, the mixture was quenched by the addition of acetone (50 mL), methanol (50 mL) and 6 N aqueous HCl (100 mL). The swollen polyethylene which separated was isolated by vacuum filtration, then dried at 80° C. in vacuo for several hours. 860 mg of a white powdery polyethylene was isolated (87,000 TO/h). $^1$H NMR: 15 branches/1000 carbon atoms. GPC: $M_n$=76,000; $M_w/M_n$=2.6

Example 73

Polymerization of ethylene using a catalyst generated in situ from tetrakis(2,6-dimethylphenyl)oxalamidine, bis(1,5-cyclooctadiene)nickel(0) and HB(Ar)$_4$ (Ar=3,5-bis(trifluoromethyl)phenyl).

A 250 mL pear-shaped Schienk flask equipped with a magnetic stir bar and capped with a septum was charged with 8.0 mg of bis(1,5 -cyclooctadiene)nickel(0), 19 mg of $N^1,N^2,N^3,N^4$-tetrakis(2,6-dimethylphenyl)oxalamidine, and 33 mg of the ether solvate of HB(Ar)$_4$. The flask was evacuated and refilled with ethylene, then charged with 75 mL of dry, deoxygenated toluene. The yellow solution which resulted was stirred under ethylene at 0° C. for 30 minutes, then warmed to 25° C. and stirred for another 30 minutes under ethylene before being quenched by addition of acetone (50 mL), and methanol (50 mL). The polyethylene which separated was isolated by vacuum filtration and washed with water, methanol and acetone, then dried under reduced pressure (0.5 mm Hg) for 14 hours to give 0.70 g of an elastic white polyethylene (average 860 TO/h). $^1$H NMR: 83 branches/1000 carbon atoms. GPC: $M_n$=173,000; $M_w/M_n$=2.8.

Example 74

Polymerization of ethylene with the nickel dibromide complex of 1,4-dimethyl-2,3-bis(2,6-dimethylphenylimino) piperazine in the presence of MAO.

A 250 mL pear-shaped Schlenk flask equipped with a magnetic stir bar and capped with a septum was charged with 10.4 mg of the nickel dibromide complex of 1,4-dimethyl-2,3-bis(2,6-dimethylphenylimino)piperazine. The flask was evacuated and refilled with ethylene, then charged with 75 mL of dry, deoxygenated toluene. The resultant suspension was cooled to 0° C. and allowed to equilibrate with 1 atmosphere ethylene for 15 minutes, then treated with 4.0 mL of a 10 wt % solution of MAO in toluene. The yellow solution which resulted was stirred under ethylene at 0° C. for 1 hour, and then quenched by the addition of acetone (50 mL), methanol (50 mL) and 6 N aqueous HCl (100 mL). The swollen polyethylene which separated was isolated by vacuum filtration and washed with water, methanol and acetone, then dried under reduced pressure (0.5 mm Hg) for 14 hours to give 1.3 g of a clear elastic polyethylene (2531 TO/h). $^1$H NMR: 91 branches/1000 carbon atoms. GPC: $M_n$=127,000; $M_w/M_n$=1.3.

Example 75

Ethylene polymerization using complex XXXV.

A flame dried Schlenk flask equipped with a stir bar and a rubber septum was charged with 50 ml of methylene chloride and 50 mg of the palladium complex XXXV. The flask was placed under an ethylene atmosphere (1 atmosphere). The mixture was left to stir for 20 hours. Acetone and methanol were added to quench the reaction and precipitate the polymer. The polymer was collected and dried in vacuo resulting in 2.6 g of tacky polymer. NMR spectroscopic analysis is consistent with the preparation of an ethylene homopolymer. $^1$H NMR: highly branched polyethylene. GPC: $M_n$=34,000, $M_w/M_n$=2.5. DSC: $T_m$=−39° C., $T_g$=−69° C.

Example 76

Propylene polymerization using complex XXXV.

A flame dried Schlenk flask equipped with a stir bar and a rubber septum was charged with 50 ml of methylene chloride and 50 mg of the palladium complex XXXV. The flask was placed under a propylene atmosphere (1 atmosphere). The mixture was left to stir for 20 hours. Acetone and methanol were added to quench the reaction and precipitate the polymer. The polymer was collected and dried in vacuo resulting in 580 mg of tacky polymer. $^1$H NMR: 192 branch points/1000 carbon atoms. GPC: $M_n$=17.000, $M_w/M_n$=2.08. DSC: $T_g$=−53° C.

Example 77

Ethylene/vinyl ethylene carbonate copolymerization using complex XXXV.

A 200 mL flame dried pear-shaped Schlenk flask equipped with a magnetic stir bar and capped with a septum was charged with (2,6-diisopropylphenylimino)-[1,4]dithiane Pd(II) catalyst XXXV (100 mg) in an argon filled glove box. Upon removal from the glove box, the flask was evacuated and backfilled with ethylene. The catalyst was dissolved in $CH_2Cl_2$ (25 mL) and immediately treated with vinyl ethylene carbonate (5 mL). The resulting orange solution was stirred at 23° C. under an ethylene atmosphere (1 atm) for 20 hours. A small amount of polymer had precipitated out of solution. The polymerization was quenched with MeOH and acetone leaving gray oil adhering to the walls of the flask. The polymer was washed several times with acetone and MeOH to remove any remaining monomer. The polymer was dissloved in $CH_2Cl_2$ and transferred to a storage jar. The solvent was left to evaporate and the resulting oily polymer was dried in vacuo at ~80° C. for 3 days to afford a tacky solid (2.15 g, 1100 TO). $^1H$ NMR was consistent with a copolymer containing approximately 96.5 weight % ethylene and 3.5 weight % vinyl ethylene carbonate monomer units.; $M_n$ 40,200 $^g/_{mol}$; $M_w$ 92,100 $^g/_{mol}$; DSC $T_g$ ~68° C. $T_m$ −38° C.

Example 78

Ethylene/vinyl ethylene carbonate copolymerization using complex XXXV. A 200 mL flame dried pear-shaped Schlenk flask equipped with a magnetic stir bar and capped with a septum was charged with (2,6-diisopropylphenylimino)-[1,4]dithiane Pd(II) catalyst XXXV (100 mg) in an argon filled glove box. Upon removal from the glove box, the flask was evacuated and backfilled with ethylene. The catalyst was dissolved in $CH_2Cl_2$ (20 mL) and immediately treated with vinyl ethylene carbonate (10 mL). The resulting orange solution was stirred at 23° C. under an ethylene atmosphere (1 atm) for 28 hours. A small amount of polymer had precipitated out of solution. The polymerization was quenched with MeOH and acetone leaving gray oil adhering to the walls of the flask. The polymer was dissloved in $CH_2Cl_2$ and transferred to a storage jar. The solvent was left to evaporate and the resulting oily polymer was washed several times with acetone and MeOH to remove any remaining monomer and dried in vacuo at ~80° C. for 1 day to afford a tacky solid (1.15 g, 613 TO). $^1H$ NMR was consistent with a copolymer containing approximately 95.5 weight % ethylene and 4.5 weight % vinyl ethylene carbonate monomer units.; $M_n$ 15,400 $^g/_{mol}$; $M_w$ 96,000 $^g/_{mol}$; DSC $T_g$ −64° C., $T_m$ −31° C.

Example 79

Preparation of the nickel dibromide complex of 2,3-bis(2,6-diisopropylphenylimino)-[1,4]dioxane.

A Schienk flask equipped with a magnetic stir bar was charged with 100 mg of 2,3-bis(2,6-diisopropylphenylimino)-[1,4]dioxane (0.25 mmol) and 71 mg of (1,2-dimethoxyethane)nickel(II) dibromide (0.23 mmol) under an argon atmosphere. Dry, deoxygenated dichloromethane (15 mL) was added and the mixture was stirred under an argon atmosphere, turning red-brown within about 10 minutes. After 2 hours, the red/orange solution was transferred via filter cannula to a new flame dried Schlenk to remove trace amount of unreacted (1,2-dimethoxyethane) nickel(II) dibromide. The $CH_2Cl_2$ was removed in vacuo. The resulting red-brown solid was washed with 2×10 mL of hexane and the solid was dried in vacuo for several hours affording 80 mg of a brown solid.

Example 80

Preparation of 2,3-bis(2,6-dimethylphenylimino)-2,3-dihydroimidazo[2,1-b]thiazole.

A 50 mL round bottom flask equipped with a magnetic stir bar and a reflux condenser capped by a nitrogen inlet was charged with 752 mg of $N^1$, $N^2$-bis(2,6-dimethylphenyl)oxalodiimidoyl dichloride, 200 mg of sodium hydride (60% mineral oil dispersion), 5.0 mL of dry tetrahydrofuran, and 250 mg of 2-mercaptoimidazole. The mixture was heated at reflux for 120 minutes. After cooling, the mixture was diluted with water and dichloromethane, and the organic layer was separated and concentrated to afford a yellow-orange oil. Column chromatography ($SiO_2$, Merck Grade 9385 230–400 mesh, 60 Å; 12 v % ethyl acetate in hexane) afforded 487 mg of a yellow-orange solid. Recrystallization from heptane gave 366 mg yellow-orange prisms. Field desorption mass spectrometry showed a parent ion peak at 360 m/z.

Example 81

Preparation of $N^1,N^2$-bis(2,6-dimethylphenyl) ethanediimidoselenoic acid diphenyl ester.

A 50 mL round bottom flask equipped with a magnetic stir bar and a reflux condenser capped by a nitrogen inlet was charged with 961 mg of $N^1,N^2$-bis(2,6-dimethylphenyl)oxalodiimidoyl dichloride, 287 mg of sodium hydride (60% mineral oil dispersion), 8.2 mL of dry tetrahydrofuran, and 0.068 mL of benzeneselenol. The mixture was heated at reflux for 45 minutes. After cooling, the mixture was diluted with water and diethyl ether. The ether layer was separated and washed again with water, then concentrated in vacuo to afford a yellow-orange crystalline solid. The solid was dissolved in hot hexane, then filtered, and then reconcentrated. Recrystallization from heptane afforded 745 mg orange prisms, $_1$st crop. Field desorption mass spectrometry showed a parent ion cluster of peaks from 570–578 m/z. $^1H$ NMR (300 MHz, $CDCl_3$, chemical shifts in ppm relative to TMS at 0 ppm): 1.95 (12 p, s), 6.75 (6 p, app s), 7.02–7.20 (6 p, m), 7.39–7.48 (4 p, m).

Example 82

Polymerization of ethylene using a catalyst generated in situ from $N^1,N^2$-bis(2,6-dimethylphenyl)ethanediimidoselenoic acid diphenyl ester, bis(1,5-cyclooctadiene)nickel(0) and $HB(Ar)_4$ (Ar=3,5-bis(trifluoromethyl)phenyl).

A 250 mL pear-shaped Schlenk flask equipped with a magnetic stir bar and capped with a septum was charged with 5 mg of bis(1,5-cyclooctadiene)nickel(0), 10 mg of $N^1$,$N^2$-bis(2,6-dimethylphenyl)ethanediimidoselenoic acid diphenyl ester, and 25 mg of the ether solvate of $HB(Ar)_4$. The flask was evacuated and refilled with ethylene, then charged with 45 mL of dry, deoxygenated toluene. The yellow solution which resulted was stirred under ethylene at 21° C. for 10 minutes, then quenched by addition of methanol (50 mL). The polyethylene which separated was isolated by vacuum filtration and washed with methanol, then dried under reduced pressure (0.5 mm Hg) for 14 hours to give 0.060 g of an elastic blue-green polyethylene. $^1H$ NMR: 24 branches/1000 carbon atoms. GPC: $M_n$=181,000; $M_w/M_n$= 3.5.

Example 83

Preparation of the nickel dibromide complex of 2,3-bis(2,6-dimethylphenylimino)-2,3-dihydroimidazo[2,1-b]thiazole.

A 50 mL Schlenk flask equipped with a magnetic stir bar and capped with a septum was charged with 141 mg of 2,3-bis(2,6-dimethylphenylimino)-2,3-dihydroimidazo[2,1-b]thiazole and 110 mg of (1,2-dimethoxyethane)nickel(II) dibromide under an inert atmosphere. Dry, deoxygenated dichloromethane (5 mL) was added and the mixture was stirred under an argon atmosphere. After 1 hour, another 5 mL of dichloromethane was added. The mixture was stirred another 16 hours at 21° C., then diluted with 10 mL of dry, deoxygenated hexane and stirred another 3 hours. The supernatant was removed via a filter paper-tipped cannula, and the residue dried in vacuo at 1 mm Hg to afford 66 mg of a brown microcrystalline solid.

Example 84
Polymerization of ethylene with the nickel dibromide complex 2,3-bis(2,6-dimethylphenylimino)-2,3-dihydroimidazo[2,1-b]thiazole in the presence of MAO.

A 200 mL pear-shaped Schlenk flask equipped with a magnetic stir bar and capped with a septum was charged with 2.5 mg of the nickel dibromide complex of 2,3-bis(2,6-dimethylphenylimino)-2,3-dihydroimidazo[2,1-b]thiazole. The flask was evacuated and refilled with ethylene, then charged with 75 mL of dry, deoxygenated toluene. The resultant suspension allowed to equilibrate with 1 atmosphere ethylene at 21° C. for 15 minutes, then treated with 200 μL of a 10 wt % solution of MAO in toluene and stirred under 1 atmosphere ethylene. After 21 min, the reaction was quenched by the addition of acetone (50 mL), methanol (50 mL) and 6 N aqueous HCl (100 mL). The swollen polyethylene which separated was isolated by vacuum filtration and washed with water, methanol and acetone, then dried under reduced pressure (0.05–0.1 mm Hg) for 24 hours to give 198 mg of a white polyethylene. $^1$H NMR: 13 branches/1000 carbon atoms. GPC: bimodal, with $M_n$=23,000: $M_p$=366,000; $M_w/M_n$=13.5.

Example 85
Preparation of the nickel dibromide complex of $N^1,N^2,N^3,N^4$-tetrakis(2,6-dimethylphenyl)oxalamidine.

A 50 mL Schlenk flask equipped with a magnetic stir bar and capped with a septum was charged with 100 mg of $N^1,N^2,N^3,N^4$-tetrakis(2,6-dimethylphenyl)oxalamidine and 55 mg of (1,2-dimethoxyethane)nickel(II) dibromide under an inert atmosphere. Dry, deoxygenated dichloromethane (5 mL) was added and the mixture was stirred under an argon atmosphere. After 1 hour, another 5 mL of dichloromethane was added. The mixture was stirred another 16 hours at 21° C. then diluted with 10 mL of dry, deoxygenated hexane and stirred another 3 hours. The supernatant was removed via a filter paper-tipped cannula, and the residue dried in vacuo at 1 mm Hg to afford 95 mg of light green crystals.

Example 86
Polymerization of ethylene with the nickel dibromide complex of $N^1,N^2,N^3,N^4$-tetrakis(2,6-dimethylphenyl)oxalamidine in the presence of MAO.

A 200 mL pear-shaped Schlenk flask equipped with a magnetic stir bar and capped with a septum was charged with 2.4 mg of nickel dibromide complex of $N^1,N^2,N^3,N^4$-tetrakis(2,6-dimethylphenyl)oxalamidine. The flask was evacuated and refilled with ethylene, then charged with 75 mL of dry, deoxygenated toluene. The resultant suspension allowed to equilibrate with 1 atmosphere ethylene at 21° C. for 15 minutes, then treated with 4.0 mL of a 10 wt % solution of MAO in toluene and stirred under 1 atmosphere ethylene. After 30 min, the reaction was quenched by the addition of acetone (50 mL), methanol (50 mL) and 6 N aqueous HCl (100 mL). The swollen polyethylene which separated was isolated by vacuum filtration and washed with water, methanol and acetone, then dried under reduced pressure (0.05–0.1 mm Hg) for 24 hours to give 743 mg of a white polyethylene. $^1$H NMR: 112 branches/1000 carbon atoms. GPC: $M_n$=330,000; $M_w/M_n$=1.4.

Example 87
Copolymerization of ethylene and 1-pentene with the nickel dibromide complex of 2,3-bis(2,6-dimethylphenylimino)-[1,4]dithiane in the presence of MAO.

A 200 mL pear-shaped Schlenk flask equipped with a magnetic stir bar and capped with a septum was charged with 0.5 mL of a stock solution of 12.4 mg of the nickel dibromide complex of 2,3-bis(2,6-dimethylphenylimino)-[1,4]dithiane in 10.0 mL dichloromethane. The flask was evacuated and refilled with ethylene, then charged with 100 mL of dry, deoxygenated toluene, and 5.0 mL 1-pentene. The resultant suspension was cooled to 0° C. and allowed to equilibrate with 1 atmosphere ethylene for 15 minutes, then treated with 4.0 mL of a 10 wt % solution of MAO in toluene and stirred under 1 atmosphere ethylene. After 45 minutes, the mixture was quenched by the addition of acetone (50 mL), methanol (50 mL) and 6 N aqueous HCl (100 mL). The swollen copolymer which separated was isolated by vacuum filtration and washed with water, methanol and acetone, then dried under reduced pressure (255 mm Hg) at 100° C. for 24 hours to obtain 2.0 g of white coploymer. $^1$H NMR: 24 branches/1000 carbon atoms. $^{13}$C NMR: 7.6 methyl branches/1000 carbons. 1.2 ethyl branches/1000 carbons, 9.1 propyl branches/1000 carbons, 2.1 butyl branches/1000 carbons, 3.4 pentyl and higher alkyl branches/1000 carbons. GPC: $M_n$=274,000; $M_w/M_n$=2.3.

Example 88
Copolymerization of ethylene and 1-heptene with the nickel dibromide complex of 2,3-bis(2,6-dimethylphenylimino)-[1,4]dithiane in the presence of MAO.

A 200 mL pear-shaped Schlenk flask equipped with a magnetic stir bar and capped with a septum was charged with 0.5 mL of a stock solution of 12.4 mg of the nickel dibromide complex of 2,3-bis(2,6-dimethylphenylimino)-[1,4]dithiane in 10.0 mL dichloromethane. The flask was evacuated and refilled with ethylene, then charged with 100 mL of dry, deoxygenated toluene, and 5.0 mL 1-heptene. The resultant suspension was cooled to 0° C. and allowed to equilibrate with 1 atmosphere ethylene for 15 minutes, then treated with 4.0 mL of a 10 wt % solution of MAO in toluene and stirred under 1 atmosphere ethylene. After 33 minutes, the mixture was quenched by the addition of acetone (50 mL), methanol (50 mL) and 6 N aqueous HCl (100 mL). The swollen copolymer which separated was isolated by vacuum filtration and washed with water, methanol and acetone, then dried under reduced pressure (255 mm Hg) at 100° C. for 24 hours to obtain 1.25 g of white coploymer. $^1$H NMR: 19 branches/1000 carbon atoms. $^{13}$C NMR: 5.9 methyl branches/1000 carbons, less than 1 ethyl branch/1000 carbons, less than 1 propyl branch/1000 carbons, 1.8 butyl branches/1000 carbons, 11.5 pentyl and higher alkyl branches/1000 carbons. GPC: $M_n$=223,000; $M_w/M_n$=2.3.

Example 89
Polymerization of 1-hexene with the nickel dibromide complex of 2,3-bis(2,6-dimethylphenylimino)-[1,4]dithiane in the presence of MAO.

A 22 mL vial equipped with a magnetic stir bar and capped by a septum was sequentially charged with 1.8 mg of the nickel dibromide complex of 2,3-bis(2,6-dimethylphenylimino)-[1,4]dithiane, 4.0 mL 1-hexene, and 2.0 mL of a 10 wt % solution of MAO in toluene, under Ar. The resultant violet mixture thickened noticably within minutes. After 34 min, the reaction was quenched with acetone, methanol and 6 N aq HCl, and the polyhexene which separated was filtered off and dried in vacuo (0.4 mm Hg) to obtain 428 mg of an elastic polyhexene. $^1$H NMR: 173 branches/1000 carbon atoms. GPC: $M_n$=92,000; $M_w/M_n$=2.0.

Example 90
Polymerization of 1-hexene with the nickel dibromide complex 2,3-bis(2,6-dimethylphenylimino)-2,3-dihydroimidazo[2,1-b]thiazole in the presence of MAO.

A 22 mL vial equipped with a magnetic stir bar and capped by a septum was sequentially charged with 2.1 mg of the nickel dibromide complex 2,3-bis(2,6-dimethylphenylimino)-2,3-dihydroimidazo[2,1-b]thiazole, 4.0 mL 1-hexene, and 2.0 mL of a 10 wt % solution of MAO in toluene, under Ar. The resultant dark purple-brown mixture thickened noticably within 10–20 minutes. After 53 min, the reaction was quenched with acetone, methanol and 6 N aq HCl, and the polyhexene which separated was filtered off and dried in vacuo (0.4 mm Hg) to obtain 283 mg of an elastic polyhexene. $^1$H NMR: 110 branches/1000 carbon atoms. GPC: $M_n$=91,000; $M_w/M_n$=1.9.

Example 91

Polymerization of 1-hexene with the nickel dibromide complex of 1,4-dimethyl-2,3-bis(2,6-dimethylphenylimino) piperazine in the presence of MAO.

A 22 mL vial equipped with a magnetic stir bar and capped by a septum was sequentially charged with 2.1 mg of nickel dibromide complex of 1,4-dimethyl-2.3-bis(2,6-dimethylphenylimino)piperazine. 4.0 mL 1 -hexene, and 2.0 mL of a 10 wt % solution of MAO in toluene, under Ar. The resultant clear yellow solution was stirred at 23° C. for 400 min, then the reaction was quenched with acetone, methanol and 6 N aq HCl, and the polyhexene which separated was filtered off and dried in vacuo (0.4 mm Hg) to obtain 408 mg of an elastic polyhexene. $^1$H NMR: 90 branches/1000 carbon atoms. GPC: $M_n$=47,000; $M_w/M_n$=1.7.

Example 92

Synthesis of the supported nickel complex of 2,3-bis(2,6-dimethylphenylimino)-[1,4]dithiane.

A flame dried pear-shaped flask equipped with a stir bar and a septum was charged with 30 mg (52 μmol) of the nickel dibromide complex of 2,3-bis(2,6-dimethylphenylimino)-[1,4]dithiane and 1 g of MAO treated silica (purchased from Witco TA 02794/HL/04). The solid mixture was cooled to 0° C. in an ice bath and 25 mL of the CH$_2$Cl$_2$ was added. The reaction was rapidly stirred at 0° C. for 1 hour. After 1 hour the solvent was removed in vacuo. The resulting purple solid was washed with CH$_2$Cl$_2$ using a filter cannula and dried under dynamic vacuum.

Example 93

Synthesis of the supported nickel complex of 2,3-bis(2,6-dimethylphenylimino)-[1,4]dithiane.

A flame dried pear-shaped flask equipped with a stir bar and a septum was charged with 15 mg (26 μmol) of the nickel dibromide complex of 2,3-bis(2,6-dimethylphenylimino)-[1,4]dithiane and 1 g of MAO treated silica (purchased from Witco TA 02794/HL/04). The solid mixture was cooled to 0° C. in an ice bath and 20 mL of toluene was added. The reaction was rapidly stirred at 0° C. for 1 hour. After 1 hour the solid was allowed to settle and the solvent was removed via filter cannula. The resulting purple solid was washed with toluene using a filter cannula. The resulting purple silica support material was dried under dynamic vacuum giving 916 mg of supported catalyst material.

Example 94

Synthesis of the supported nickel complex of 2,3-bis(2,6-dimethylphenylimino)-[1,4]dithiane.

A flame dried pear-shaped flask equipped with a stir bar and a septum was charged with 30 mg (52 μmol) of the nickel dibromide complex of 2,3-bis(2,6-dimethylphenylimino)-[1,4]dithiane and 1 g of MAO treated silica (purchased from Witco TA 02794/HL/04). The solid mixture was cooled to 0° C. in an ice bath and 20 mL of toluene was added. The reaction was rapidly stirred at 0° C. for 1 hour. After 1 hour the solid was allowed to settle and the solvent was removed via filter cannula. The resulting purple solid was washed with toluene using a filter cannula and was dried under dynamic vacuum giving 900 mg of supported catalyst material.

Example 95

Synthesis of the supported nickel complex of 2,3-bis(2,6-diisopropylphenylimino)-[1,4]dithiane.

A flame dried pear-shaped flask equipped with a stir bar and a septum was charged with 34 mg (50 μmol) of the nickel dibromide complex of 2,3-bis(2,6-diisopropylphenylimino)-[1,4]dithiane and 1 g of MAO treated silica (purchased from Witco TA 02794/HL/04). The solid mixture was cooled to 0° C. in an ice bath and 20 mL of CH$_2$Cl$_2$ was added. The reaction was rapidly stirred at 0° C. for 1 hour. After 1 hour the solvent was removed in vacuo. The resulting red brown solid was washed with CH$_2$Cl$_2$ using a filter cannula and dried under dynamic vacuum giving 780 mg of supported catalyst.

Example 96

Synthesis of the supported nickel complex of 2,3-bis(2,6-dimethylphenylimino)-f[1,4]dithiane.

A flame dried pear-shaped flask equipped with a stir bar and a septum was charged with 15 mg (26 μmol) of the nickel dibromide complex of 2,3-bis(2,6-dimethylphenylimino)-[1,4]dithiane and 1 g of MAO treated silica (purchased from Witco TA 02794/HL/04). The solid mixture was cooled to 0° C. in an ice bath and 20 mL of CH$_2$Cl$_2$ was added. The reaction was rapidly stirred at 0° C. for 1 hour. After 1 hour the solvent was removed in vacuo resulting in 940 mg of a purple solid.

Example 97

Polymerization of ethylene using the supported nickel complex of 2,3-bis(2,6-dimethylphenylimino)-[1,4]dithiane prepared in example 92.

A flame dried pear-shaped flask equipped with a stir bar and a septum was charged with 100 mg of the nickel /MAO treated silica supported catalyst system prepared in example 92. The flask was placed under an ethylene atmosphere and 50 mL of toluene was added giving a red/brown suspension. The polymerization was left to stir for 1 hour at 23° C. After 60 minutes at 23° C., the reaction was quenched by the addition of acetone, 6M HCl and methanol. The swollen polyethylene was isolated by filtration and dried for several hours in a vacuum oven at 100° C. resulting in 1.6 g of a white rubbery solid (11,000 TO/h based on 100 % active catalyst). DSC: (2nd heat) melt with an endothermic maximum at 118° C. $^1$H NMR: 30 branches/1000 carbon atoms. GPC: Mn=208,000; Mw/Mn=2.45.

Example 98

Polymerization of ethylene using the supported nickel complex of 2,3-bis(2,6-dimethylphenylimino)-[1,4]dithiane prepared in example 92.

A 600 mL Parr® autoclave was first heated to about 100° C. under dynamic vacuum to ensure the reactor was dry. The reactor was then purged with argon. The 600 mL Parr® autoclave was charged in the glove box with 200 mg of the supported catalyst prepared in example 92. Upon removing the autoclave from the box, 150 mL of toluene was added and the reactor was heated to 60° C. The reactor was rapidly pressurized to 90 psig ethylene. After 60 minutes at 60° C., the reaction was quenched by the addition of acetone, 6M HCl and methanol. The swollen polyethylene was isolated by filtration and dried for several hours in a vacuum oven at 100° C. resulting in 22.5 g of a white rubbery solid (80,000 TO/h). $^1$H NMR: 31 branches/1000 carbon atoms. GPC: Mn=128,000; Mw/Mn=2.58.

Example 99

Polymerization of ethylene using the supported nickel complex of 2,3-bis(2,6-dimethylphenylimino)-[1,4]dithiane prepared in example 92.

A 600 mL Parr® autoclave was first heated to about 100° C. under dynamic vacuum to ensure the reactor was dry. The reactor was then purged with argon. The 600 mL Parr® autoclave was charged in the glove box with 100 mg of the supported catalyst prepared in example 92. Upon removing the autoclave from the box, 150 mL of toluene was added and the reactor was heated to 100° C. The reactor was rapidly pressurized to 90 psig ethylene and the temperature ramped up to 140° C. After 60 minutes at 140° C., the reaction was quenched by the addition of acetone, 6M HCl and methanol. The swollen polyethylene was isolated by filtration and dried for several hours in a vacuum oven at 100° C. GPC: Mn=56,000; Mw/Mn=7.19.

Example 100

Polymerization of ethylene using the supported nickel complex of 2,3-bis(2,6-diisopropylphenylimino)-[1,4]dithiane prepared in example 95.

A 600 mL Parr® autoclave was first heated to about 100° C. under dynamic vacuum to ensure the reactor was dry. The reactor was then purged with argon. The 600 mL Parr® autoclave was charged in the glove box with 100 mg of the supported catalyst prepared in example 95. Upon removing the autoclave from the box, 150 mL of toluene was added and the reactor was heated to 50° C. The reactor was rapidly pressurized to 90 psig ethylene. After 30 minutes at 50° C., the reaction was quenched by the addition of acetone, 6M HCl and methanol. The swollen polyethylene was isolated by filtration and dried for several hours in a vacuum oven at 100° C. resulting in 1.25 g of a white rubbery solid (18,000 TO/h). $^1$H NMR: 62 branches/1000 carbon atoms. GPC: Mn=336,000; Mw/Mn=2.22.

Example 101

Polymerization of ethylene using the supported nickel complex of 2,3-bis(2,6-dimethylphenylimino)-[1,4]dithiane prepared in example 93.

A 600 mL Parr® autoclave was first heated to about 100° C. under dynamic vacuum to ensure the reactor was dry. The reactor was then purged with argon. The 600 mL Parr® autoclave was charged in the glove box with 100 mg of the supported catalyst prepared in example 93. Upon removing the autoclave from the box, 150 mL of toluene was added and the reactor was heated to 50° C. The reactor was rapidly pressurized to 90 psig ethylene. After 60 minutes at 50° C., the reaction was quenched by the addition of acetone, 6M HCl and methanol. The swollen polyethylene was isolated by filtration and dried for several hours in a vacuum oven at 100° C. resulting in 2.13 g of a white rubbery solid (30,000 TO/h). DSC: $2^{nd}$ heat showed an endothermic maximum at 120° C. $^1$H NMR. 17 branches/1000 carbon atoms. GPC: Mn=119,000; Mw/Mn=2.93.

Example 102

Polymerization of ethylene using the supported nickel complex of 2,3-bis(2,6-dimethylphenylimino)-[1,4]dithiane prepared in example 94.

A 600 mL Parr® autoclave was first heated to about 100° C. under dynamic vacuum to ensure the reactor was dry. The reactor was then purged with argon. The 600 mL Parr® autoclave was charged in the glove box with 100 mg of the supported catalyst prepared in example 94. Upon removing the autoclave from the box, 150 mL of toluene was added and the reactor was heated to 50° C. The reactor was rapidly pressurized to 90 psig ethylene. After 60 minutes at 50° C., the reaction was quenched by the addition of acetone, 6M HCl and methanol. The swollen polyethylene was isolated by filtration and dried for several hours in a vacuum oven at 100° C. resulting in 5.97 g of a white rubbery solid (41,000 TO/h). DSC: $2^{nd}$ heat showed an endothermic maximum at 120° C. GPC: Mn=138,000; Mw/Mn=2.95. $^1$H NMR: 17 branches/1000 carbon atoms.

Example 103

Polymerization of ethylene using the supported nickel complex of 2,3-bis(2,6-dimethylphenylimino)-[1,4]dithiane prepared according to the procedure described in example 92.

A 600 mL Parr® autoclave was first heated to about 100° C. under dynamic vacuum to ensure the reactor was dry. The reactor was then purged with argon. The 600 mL Parr® autoclave was charged in the glove box with 100 mg of supported catalyst. Upon removing the autoclave from the box, 150 mL of toluene was added and the reactor was heated to 65° C. The reactor was rapidly pressurized to 100 psig ethylene. After 60 minutes at 65° C., the reaction was quenched by the addition of acetone, 6M HCl and methanol. The swollen polyethylene was isolated by filtration and dried for several hours in a vacuum oven at 100° C. resulting in 9.0 g of a white rubbery solid (62,000 TO/h). DSC: $2^{nd}$ heat showed an endothermic maximum at 116° C. GPC: Mn=83,500; Mw/Mn=4.71. $^1$H NMR: 35 branches/1000 carbon atoms.

Example 104

Polymerization of ethylene using the supported nickel complex of 2,3-bis(2,6-dimethylphenylimino)-[1,4]dithiane prepared in example 96.

A 600 mL Parr® autoclave was first heated to about 100° C. under dynamic vacuum to ensure the reactor was dry. The reactor was then purged with argon. The 600 mL Parr® autoclave was charged in the glove box with 100 mg of the supported catalyst prepared in example 96. Upon removing the autoclave from the box, 150 mL of toluene was added and the reactor was heated to 50° C. The reactor was rapidly pressurized to 100 psig ethylene. After 60 minutes at 50° C., the reaction was quenched by the addition of acetone, 6M HCl and methanol. The swollen polyethylene was isolated by filtration and dried for several hours in a vacuum oven at 100° C. resulting in 6.5 g of a white rubbery solid (88,000 TO/h). DSC: $2^{nd}$ heat showed a broad melt transition with an endothermic maximum at 119° C. GPC: Mn=182,600; Mw/Mn=3.01. $^1$H NMR: 19 branches/1000 carbon atoms.

Example 105

Polymerization of ethylene using the supported nickel complex of 2,3-bis(2,6-dimethylphenylimino)-[1,4]dithiane prepared in example 96.

A 600 mL Parr® autoclave was first heated to about 100° C. under dynamic vacuum to ensure the reactor was dry. The reactor was then purged with argon. The 600 mL Parr® autoclave was charged in the glove box with 100 mg of the supported catalyst prepared in example 96. Upon removing the autoclave from the box, 150 mL of toluene was added and the reactor was heated to 50° C. The reactor was rapidly pressurized to 100 psig ethylene. After 60 minutes at 50° C., the reaction was quenched by the addition of acetone, 6M HCl and methanol. The swollen polyethylene was isolated by filtration and dried for several hours in a vacuum oven at 100° C. resulting in 5.4 g of a white rubbery solid (74,000 TO/h). DSC: $2^{nd}$ heat showed abroad melt transition with an endothermic maximum at 120° C. GPC: Mn=186,500; Mw/Mn=2.66. $^1$H NMR: 18 branches/1000 carbon atoms.

Example 106

Polymerization of ethylene using the supported nickel complex of 2.3-bis(2,6-dimethylphenylimino)-[1,4]dithiane prepared in example 96.

A 600 mL Parr® autoclave was first heated to about 100° C. under dynamic vacuum to ensure the reactor was dry. The reactor was then purged with argon. The 600 mL Parr® autoclave was charged in the glove box with 100 mg of the supported catalyst prepared in example 96. Upon removing the autoclave from the box, 150 mL of toluene was added and the reactor was heated to 30° C. The reactor was rapidly pressurized to 100 psig ethylene. After 60 minutes at 30° C., the reaction was quenched by the addition of acetone, 6M HCl and methanol. The swollen polyethylene was isolated by filtration and dried for several hours in a vacuum oven at 100° C. resulting in 11.5 g of a white rubbery solid (160,000 TO/h). DSC: $2^{nd}$ heat showed an endothermic maximum at 127° C. GPC: Mn=279,000; Mw/Mn=2.73. $^1$H NMR: 7 branches/1000 carbon atoms.

Example 107

Synthesis of the supported nickel complex of 2,3-bis (phenylimino)-[1,4]dithiane.

A 500 mL flame-dried pear-shaped flask equipped with a magnetic stir bar and capped by a septum was charged with 27 mg (52 µmol) of the nickel dibromide complex of 2,3-bis(phenylimino)-[1,4]dithiane and 1.0 g of MAO treated silica (Witco TA 02794/HL/04). The solid mixture was cooled to 0° C. in an ice bath and 25 mL of dry, deoxygenated $CH_2Cl_2$ was added. The reaction was stirred at 0° C. for 50 min, then the volatiles were removed by evaporation under reduced pressure (0.2 torr) at 0° C. for 40 min to afford the supported catalyst as a light green-grey powder which was stored under nitrogen at –25° C.

Example 108

Synthesis of the supported nickel complex of 2,3-bis(2-tert-butylphenylimino)-[1,4]dithiane.

A 500 mL flame-dried pear-shaped flask equipped with a magnetic stir bar and capped by a septum was charged with 34 mg (56 µmol) of the nickel dibromide complex of 2,3-bis(2-tert-butylphenylimino)-[1.4]dithiane and 1.0 g of MAO treated silica (Witco TA 02794/HL/04). The solid mixture was cooled to 0° C. in an ice bath and 25 mL of dry, deoxygenated $CH_2Cl_2$ was added. The reaction was stirred at 0° C. for 50 min, then the volatiles were removed by evaporation under reduced pressure (0.2 torr) at 0° C. for 40 min to afford the supported catalyst as a light brown powder which was stored under nitrogen at –25° C.

Example 109

Synthesis of the supported nickel complex of 2,3-bis(2,6-dimethylphenylimino)-[1,4]dioxane.

A 500 mL flame-dried pear-shaped flask equipped with a magnetic stir bar and capped by a septum was charged with 30 mg (55 µmol) of the nickel dibromide complex of 2,3-bis(2,6-dimethylphenylimino)-[1,4]dioxane and 1.01 g of MAO treated silica (Witco TA 02794/HL/04). The solid mixture was cooled to 0° C. in an ice bath and 25 mL of dry, deoxygenated $CH_2Cl_2$ was added. The reaction was stirred at 0° C. for 65 min, then the volatiles were removed by evaporation under reduced pressure (0.2 torr; 20 min at 0° C., 75 min at 25° C.) to afford the supported catalyst as a brown powder which was stored under nitrogen at –25° C.

Example 110

Polymerization of ethylene using the supported nickel complex of 2,3-bis(phenylimino)-[1,4]dithiane.

A 500 mL flame-dried pear-shaped flask equipped with a magnetic stir bar and capped by a septum was charged with 100 mg of the supported nickel complex of 2,3-bis (phenylimino)-[1,4]dithiane prepared in Example 107. The flask was evacuated and refilled with ethylene, then treated with 50 mL of dry, deoxygenated toluene and stirred under 1 atm ethylene at 23° C. for 14 h. The reaction was quenched by the addition of methanol, acetone and 6 N HCl. The polymer which separated was isolated by filtration and dried in vacuo to afford 0.177 g of white, powdery polyethylene. DSC: (2nd heat) melt endothermic maxima at ca. 100, 106 and 127° C. GPC: $M_n$=1,100 g/mol; $M_w/M_n$=15.5.

Example 111

Polymerization of ethylene using the supported nickel complex of 2,3-bis(2-tert-butylphenylimino)-[1,4]dithiane.

A 500 mL flame-dried pear-shaped flask equipped with a magnetic stir bar and capped by a septum was charged with 100 mg of the supported nickel complex of 2,3-bis(2-tert-butylphenylimino)-[1,4]dithiane prepared in Example 108. The flask was evacuated and refilled with ethylene, then treated with 50 mL of dry, deoxygenated toluene and stirred under 1 atm ethylene at 23° C. for 125 min. The reaction was quenched by the addition of methanol, acetone and 6 N HCl. The polymer which separated was isolated by filtration and dried in vacuo to afford 0.529 g of white, powdery polyethylene. DSC: (2nd heat) melt endothermic maxima at 96 and 110° C. $^1$H NMR (o-dichlorobenzene): 36 branches/1000 carbon atoms. GPC: $M_n$=120,000; $M_w/M_n$=2.46.

Example 112

Polymerization of ethylene using the supported nickel complex of 2,3-bis(2,6-dimethylphenylimino)-[1,4]dioxane.

A 500 mL flame-dried pear-shaped flask equipped with a magnetic stir bar and capped by a septum was charged with 106 mg of the supported nickel complex of 2,3-bis(2,6-dimethylphenylimino)-[1,4]dioxane prepared in Example 109. The flask was evacuated and refilled with ethylene, then treated with 50 mL of dry, deoxygenated toluene and stirred under 1 atm ethylene at 23° C. for 255 min. The reaction was quenched by the addition of methanol, acetone and 6 N HCl. The polymer which separated was isolated by filtration and dried in vacuo to afford 3.2 g of white, powdery polyethylene. $^1$H NMR (o-dichlorobenzene): 20 branches/1000 carbon atoms. DSC: (2nd heat) melt endothermic maximum at 118° C. GPC: $M_n$=150,000; $M_w/M_n$=3.10.

Example 113

Copolymerization of ethylene and ethyl undecenoate using the supported nickel complex of 2,3-bis(2,6-dimethylphenylimino)-[1,4]dithiane prepared as described in example 92.

A flame dried pear-shaped flask equipped with a stir bar and a septum was charged with 100 mg of the nickel /MAO treated silica supported catalyst system. The flask was placed under an ethylene atmosphere, and 45 mL of toluene and 2.5 mL of ethyl undecenoate was added, giving a purple suspension. The polymerization was left to stir for 5 hours at 0° C. After 5 hours at 0° C., the reaction was quenched by the addition of acetone, 6M HCl and methanol. The white copolymer was isolated by filtration, washed with copious amounts of acetone and dried for several hours in a vacuum oven at 100° C. resulting in 1.3 g of a white powdery solid (1800 TO/h based on 100 % active catalyst). $^1$H NMR indicates 1 wt % of ethyl undecenoate incorporated into the copolymer.

Example 114

Copolymerization of ethylene and ethyl undecenoate using the supported nickel complex of 2,3-bis(2,6-dimethylphenylimino)-[1,4]dithiane prepared as described in example 92.

A flame dried pear-shaped flask equipped with a stir bar and a septum was charged with 100 mg of the nickel /MAO treated silica supported catalyst system. The flask was placed under an ethylene atmosphere, 45 mL of toluene and 2.5 mL of ethyl undecenoate was added giving a purple suspension. The polymerization was left to stir for 3.5 hours at 23° C. After 3.5 hours at 23° C., the reaction was quenched by the addition of acetone, 6M HCl and methanol. The white copolymer was isolated by filtration, washed with copious amounts of acetone and dried for several hours in a vacuum oven at 100° C. resulting in 1.4 g of a white powdery solid (2700 TO/h based on 100 % active catalyst). $^1$H NMR indicates 1 wt % ethyl undecenoate incorporated into the copolymer.

Obviously, numerous modifications and variations of the present invention are possible in light of the above teachings. It is therefore to be understood that within the scope of the appended claims, the invention may be practiced otherwise than as specifically described herein.

Example 115

Synthesis of the supported nickel complex of 2,3-bis(2,6-dimethylphenylimino)-[1,4]-dithiane.

A flame dried pear-shaped flask equipped with a stir bar and a septum was charged with 9 mg (16 μmol) of the nickel dibromide complex of 2,3-bis(2,6-dimethylphenylimino)-[1,4]dithiane and 3 g of MAO treated silica (purchased from Witco TA 02794/HL/04). The solid mixture was cooled to 0° C. in an ice bath and 25 ml of toluene was added. The reaction was rapidly stirred at 0° C. for 1 hour. After 1 hour, the solvent was removed in vacuo giving 2.8 g of supported catalyst material.

Example 116

Synthesis of the supported nickel complex of 2,3-bis(2,6-dimethylphenylimino)-[1,4]-dithiane.

A flame dried pear-shaped flask equipped with a stir bar and a septum was charged with 6 mg (10 μmol) of the nickel dibromide complex of 2,3-bis(2,6-dimethylphenylimino)-[1,4]dithiane and 1 g of MAO treated silica (purchased from Witco TA 02794/HL/04). The solid mixture was cooled to 0° C. in an ice bath and 20 ml of CH$_2$Cl$_2$ was added. The reaction was rapidly stirred at 0° C. for 1 hour. After 1 hour, the solvent was removed in vacuo giving a brown supported catalyst material. The supported catalysts was then suspended in 20 ml of hexane followed by addition of 2 ml (4 mmol) of trimethylaluminum (TMA). The mixture was stirred at 0° C. for one hour. The solvent was removed in vacuo along with excess TMA leaving the supported catalyst system.

Example 117

Synthesis of the supported nickel complex of 2,3-bis(2,6-dimethylphenylimino)-[1,4]-dithiane.

A flame dried pear-shaped flask equipped with a stir bar and a septum was charged with 15 mg (26 μmol) of the nickel dibromide complex of 2,3-bis(2,6-dimethylphenylimino)-[1,4]dithiane and 1 g of silica (Grace Davison XPO-2402). The solid mixture was cooled to 0° C. in an ice bath and 20 ml of toluene and 7 ml of a MAO solution in toluene was added. The reaction was rapidly stirred at 0° C. for 1 hour. After 1 hour, the solvent was removed in vacuo giving 1.3 g of supported catalyst.

Example 118

Synthesis of the supported nickel complex of 2,3-bis(2,6-dimethylphenylimino)-[1,4]-dithiane.

A flame dried pear-shaped flask equipped with a stir bar and a septum was charged with 18 mg (31 μmol) of the nickel dibromide complex of 2,3-bis(2,6-dimethylphenylimino)-[1,4]dithiane and 3 g of MAO treated silica (purchased from Witco TA 02794/HL/04). The solid mixture was cooled to 0° C. in an ice bath and 25 ml of CH$_2$Cl$_2$ was added. The reaction was rapidly stirred at 0° C. for 1 hour. After 1 hour, the solvent was removed in vacuo giving a brown supported catalyst material. The supported catalysts was then suspended in 20 ml of hexane followed by addition of 0.5 ml of MAO. The mixture was stirred at 0° C. for one hour. The solvent was removed in vacuo leaving 2.9 g of the supported catalyst.

Example 119

Synthesis of the supported nickel complex of 2,3-bis(2,6-dimethylphenylimino)-[1,4]-dithiane.

A flame dried pear-shaped flask equipped with a stir bar and a septum was charged with 6 mg (10 μmol) of the nickel dibromide complex of 2,3-bis(2,6-dimethylphenylimino)-[1,4]dithiane and 1 g of silica (Grace Davison XPO-2402). The solid mixture was cooled to 0° C. in an ice bath and 20 ml of hexane and 2 ml of a TMA solution in toluene was added. The reaction was rapidly stirred at 0° C. for 1 hour. After 1 hour, the solvent was removed in vacuo giving 0.94 g of supported catalyst.

Gas Phase Polymerization

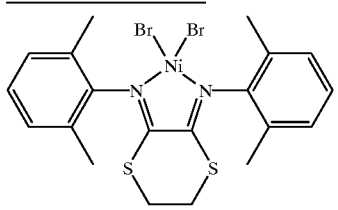

XXVII

Catalysts Preparation

A—XXVII/MAO on Silica (Witco)/0.3 mg of XXVII per gram silica. See example 115 as a representative example.

B—XXVII/MAO on Silica (Witco)/3 mg of XXVII per gram silica. See example 92 as a representative example.

C—XXVII/MAO on Silica (Witco)/0.3 mg of XXVII per gram silica/extra MAO added. See example 118 as a representative example.

D—XXVII/Silica (Grace Davison XPO-2402)/MAO solution/1.5 mg of XXVII per gram silica. See example 117 as a representative example.

E—XXVII/MAO on Silica (Witco)/0.6 mg of XXVII per gram silica/extra MAO added. See example 118 as a representative example.

F—XXVII/MAO on Silica (Witco)/0.6 mg of XXVII per gram silica/extra TMA added. See example 116 as a representative example.

G—XXVII/Silica (Grace Davison XPO-2402)/TMA solution/0.6 mg of XXVII per gram silica. See example 117 as a representative example.

H—XXVII/MAO on Silica (Witco)/0.6 mg of XXVII per gram silica. See example 115 as a representative example.

Gas Phase Polymerization Procedure

The basic procedure involves loading a 600 ml Parr® stirred autoclave with 300 g of NaCl (dried in a vacuum oven at 100° C. for 24 hours) and a known amount of supported XXVII catalyst. The ethylene homopolymerization reactions summarized below were run between 50° C. and 80° C. and 100 and 1000 psig ethylene. The resulting polyethylene was isolated by dissolving the NaCl in a blender and collecting the remaining polymer by filtration. The polyethylene was washed with 6M HCl, water and actetone. The polymer was then dried in a vacuum oven at 100° C.

A—80° C./800 psig ethylene/20 min reaction time/200 mg of supported catalyst.

B—65° C./400 psig ethylene/60 min reaction time/200 mg of supported catalyst.

C—65° C./200 psig ethylene/60 min reaction time/200 mg of supported catalyst.

D—65° C./100 psig ethylene/60 min reaction time/200 mg of supported catalyst.

E—80° C./100 psig ethylene/60 min reaction time/200 mg of supported catalyst.

F—80° C./200 psig ethylene/60 min reaction time/200 mg of supported catalyst.

G—80° C./400 psig ethylene/60 min reaction time/200 mg of supported catalyst.

H—80° C./400 psig ethylene/60 min reaction time/100 mg of supported catalyst.

I—80° C./100 psig ethylene/60 min reaction time/50 mg of supported catalyst.

J—80° C./100 psig ethylene/60 min reaction time/100 mg of supported catalyst.

K—100° C./100 psig ethylene/60 min reaction time/100 mg of supported catalyst.

L—80° C./200 psig ethylene/60 min reaction time/100 mg of supported catalyst.

M—100° C./200 psig ethylene/60 min reaction time/100 mg of supported catalyst.

N—100° C./400 psig ethylene/60 min reaction time/100 mg of supported catalyst.

O—80° C./200 psig ethylene/15 min reaction time/100 mg of supported catalyst.

P—80° C./200 psig ethylene/30 min reaction time/100 mg of supported catalyst.

| | | | Gas Phase Polymerization (Part 1) | | | | | |
|---|---|---|---|---|---|---|---|---|
| Example | Catalyst | Procedure | Mass Polymer (g) | Total TO | $M_n$ | PDI | Branches/ 1000C ($^1$HNMR) | $T_m$ (° C.) |
| 120 | A | A | 11.5 | 395K | 164K | 3.21 | 8 | 128 |
| 121 | A | B | 8.5 | 293K | 174K | 3.59 | 9 | 124 |
| 122 | A | C | 6.5 | 224K | 124K | 4.14 | 14 | 120 |
| 123 | A | D | 4.7 | 160K | 126K | 4.01 | 21 | 117 |
| 124 | A | E | 3.5 | 121K | 91K | 3.67 | 28 | 119 |
| 125 | A | F | 4.3 | 110K | 94K | 3.33 | 27 | 118 |
| 126 | A | G | 9.8 | 336K | 121K | 3.51 | 13 | 121 |
| 127 | H | B | 13.5 | 231K | 133K | 3.22 | 10 | 122 |
| 128 | H | G | 12 | 206K | 117K | 3.39 | 13 | 121 |
| 129 | H | E | 9.4 | 161K | 106K | 3.57 | 26 | 115 |
| 130 | H | H | 7.8 | 267K | 195K | 3.16 | 9 | 123 |
| 131 | B | E | 14 | 48K | 60K | 4.42 | 48 | 114 |
| 132 | B | I | 3 | 41K | 94K | 3.2 | 36 | 114 |
| 133 | B | J | 6.8 | 47K | 88K | 3.49 | 36 | 119 |
| 134 | C | J | 9 | 61K | 89K | 3.94 | 34 | 119 |
| 135 | B | K | 4.4 | 30K | 48K | 4.14 | 53 | 113 |
| 136 | C | K | 5.6 | 38K | 63K | 3.63 | 45 | 116 |
| 137 | B | L | 8 | 55K | 93K | 3.57 | 28 | 118 |
| 138 | C | L | 12 | 82K | 91K | 3.79 | 30 | 119 |
| 139 | B | M | 7 | 48K | 57K | 4.61 | 43 | 115 |
| 140 | C | M | 7 | 48K | 79k | 3.77 | 48 | 116 |
| 141 | B | H | 13.8 | 94K | 106K | 3.84 | 24 | 120 |
| 142 | B | H | 12.7 | 87K | 99K | 3.63 | 26 | 120 |
| 143 | D | J | 4 | 54K | 69K | 5.53 | 35 | 112 |
| 144 | D | K | 3 | 41K | 45K | 4.11 | 56 | 112 |
| 145 | D | L | 5 | 68K | 117K | 3.48 | 28 | 115 |
| 146 | D | M | 3.6 | 50K | 70K | 3.74 | 37 | 115 |
| 147 | D | H | 5 | 68K | 107K | 3.24 | 18 | 118 |
| 148 | D | N | 5.9 | 80K | 76K | 4.2 | 25 | 116 |
| 149 | E | J | 3.8 | 129K | 65K | 4.86 | 36 | 113 |

-continued

Gas Phase Polymerization (Part 1)

| Example | Catalyst | Procedure | Mass Polymer (g) | Total TO | $M_n$ | PDI | Branches/ 1000C ($^1$HNMR) | $T_m$ (° C.) |
|---|---|---|---|---|---|---|---|---|
| 150 | E | K | 1.5 | 51K | 43K | 4.4 | 47 | 114 |
| 151 | E | L | 4 | 137K | 74K | 4.6 | 28 | 119 |
| 152 | F | H | 47 | 161K | 106K | 3.77 | 14 | 120 |
| 153 | G | H | 0.35 | 12K | 81K | 4.32 | 23 | 119 |
| 154 | G | H | 0.25 | 9K | 57K | 5.64 | 27 | 118 |
| 155 | F | H | 3.8 | 130K | 94K | 3.46 | 18 | 120 |
| 156 | A | Q | 1.8 | 123K | 71K | 4.70 | 29 | 117 |
| 157 | A | p | 2.1 | 145k | 80K | 4.09 | 33 | 117 |
| 158 | A | L | 2.3 | 157K | 78K | 4.72 | 30 | 117 |
| 159 | B | O | 4.9 | 34K | 58K | 4.50 | 38 | 117 |

The polymer made in the gas phase in example 131 (10.57 grams) was fractionated using supercritical propane by isothermal increasing pressure profiling and critical, isobaric, temperature rising elution fractionation to give the following data. (See, B. Folie, et al., "Fractionation of Poly(ethylene-co-vinyl acetate) in Supercritical Propylene: Towards a Molecular Understanding of a Complex Macromolecule", *J. Appl. Polym. Sci.*, 64, 2015–2030,1997, and publicly available literature from Phasex Corporation, 360 Merrimack St., Lawrence, Mass. 01843, and at www.Phasex.com):

| Fraction | Temperature Collected (° C.) | Weight of Fraction (g) | $M_n$ | PDI | Branching ($^1$H NMR) | $T_m$ (° C.) |
|---|---|---|---|---|---|---|
| 1 | 40 | 1.43 | 29,500 | 2.76 | 72.2 | 50 |
| 2 | 40–60 | 0.43 | 28,600 | 3.02 | 62.3 | 55 |
| 3 | 60–65 | 0.74 | 49,400 | 2.37 | 57.5 | 79 |
| 4 | 65–75 | 0.52 | 83,100 | 2.14 | 45.9 | 92 |
| 5 | 75–85 | 0.80 | 80,900 | 2.22 | 36.5 | 99 |
| 6 | 85–95 | 0.50 | 77,400 | 2.40 | 34.3 | 102 |
| 7 | 95–100 | 0.61 | 93,200 | 2.26 | 26.3 | 108 |
| 8 | 100–110 | 0.47 | 116,000 | 2.15 | 19.3 | 117 |
| 9 | 110–140 | 0.41 | 125,000 | 2.23 | 16.7 | 122 |
| 10 | 140–150 | 0.15 | 184,000 | 2.96 | 14.3 | 124 |
| residue | — | 3.85 | — | — | <5 | — |
| Bulk Sample | — | — | 59,900 | 4.42 | 48 | 114 |

The polymer made in the gas phase in example 138 (12 grams) was fractionated using supercritical propane by isothermal increasing pressure profiling and critical, isobaric, temperature rising elution fractionation to give the following data. (See, B. Folie, et al., "Fractionation of Poly(ethylene-co-vinyl acetate) in Supercritical Propylene: Towards a Molecular Understanding of a Complex Macromolecule", *J. Appl. Polym. Sci.*, 64, 2015–2030, 1997, and publicly available literature from Phasex Corporation, 360 Merrimack St., Lawrence, Mass. 01843, and at www.Phasex.com):

| Fraction | Temperature Collected (° C.) | Weight of Fraction (g) | $M_n$ | PDI | Branching ($^1$H NMR) | $T_m$ (° C.) |
|---|---|---|---|---|---|---|
| 1 | 40 | 0.38 | 20,500 | 3.12 | 71 | 64 |
| 2 | 40–65 | 0.60 | 30,200 | 3.10 | 57 | 70 |
| 3 | 65–75 | 0.73 | 43,600 | 2.73 | 47 | 87 |
| 4 | 75–85 | 0.82 | 49,900 | 3.16 | 35 | 98 |
| 5 | 85–90 | 0.54 | 63,200 | 2.58 | 30 | 106 |
| 6 | 90–95 | 0.62 | 81,200 | 2.42 | 25 | 109 |
| 7 | 95–100 | 0.60 | 79,700 | 2.51 | 22 | 114 |
| 8 | 100–105 | 0.89 | 77,900 | 3.04 | 18 | 118 |
| 9 | 105–110 | 0.81 | 117,600 | 2.30 | 16 | 121 |
| 10 | 110–115 | 0.65 | 115,000 | 2.59 | 13 | 124 |
| 11 | 115–120 | 0.39 | 116,500 | 2.61 | 11 | 126 |
| 12 | 120–125 | 0.16 | 139,500 | 2.43 | 11 | 125 |
| 13 | 125–150 | 0.25 | 151,300 | 2.43 | — | 123 |
| residue | — | 2.2 | 141,000 | 5.29 | — | — |
| Bulk Sample | — | 12 | 90,700 | 3.79 | 30 | 119 |

Solution Phase Polymerization                                                    XXVII

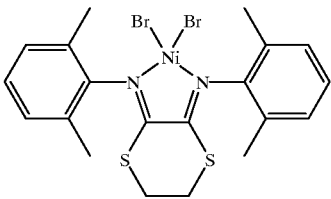

Solution Phase Polymerization Procedure

A 600 mL Parr® autoclave was first heated to about 100° C. under high vacuum to ensure the reactor was dry. The reactor was cooled and purged with argon. Under an argon atmosphere, the autoclave was charged with 150 mL of toluene and a stock solution ($CH_2Cl_2$) of the nickel dibromide complex of 2,3-bis(2,6-dimethyl-phenylimino)-4-methylmorpholine. The autoclave was heated to the desired temperature and a cocatalyst was added. The reactor was rapidly pressurized to the desired pressure. After the desired reaction time, the polymerization was quenched by the addition of acetone, and methanol. The swollen polyethylene which separated was isolated by filtration and dried for several hours in a vacuum oven at 80° C. As used herein, $Et_2AlCl$ refers to diethyl aluminum chloride.

A—cocatalyst=$Et_2AlCl$; mol cat.=$8.7 \times 10^{-7}$; solvent=mineral spirits; temperature=80° C.; ethylene pressure=600 psig; reaction time=20 min.

B—cocatalyst=Et$_2$AlCl; mol cat.=8.7×10$^{-7}$; solvent=mineral spirits; temperature=65° C.; ethylene pressure=600 psig; reaction time=20 min.

C—cocatalyst=Et$_2$AlCl; mol cat.=8.7×10$^{-7}$; solvent=mineral spirits; temperature=65° C.; ethylene pressure=800 psig; reaction time=20 min.

D—cocatalyst=Et$_2$AlCl; mol cat.=17.5×10$^{-7}$; solvent=toluene; temperature=80° C.; ethylene pressure=600 psig; reaction time=20 min.

E—cocatalyst=Et$_2$AlCl; mol cat.=17.5×10$^{-7}$; solvent=toluene; temperature=75° C.; ethylene pressure=600 psig; reaction time=20 min.

F—cocatalyst=Et$_2$AlCl; mol cat.=17.5×10$^{-7}$; solvent=toluene: temperature=75° C.; ethylene pressure=800 psig; reaction time=20 min.

G—cocatalyst=Et$_2$AlCl; mol cat.=17.5×10$^{-7}$; solvent=toluene; temperature=80° C.; ethylene pressure=400 psig; reaction time=20 min.

H—cocatalyst=Et$_2$AlCl; mol cat.=17.5×10$^{-7}$; solvent=toluene; temperature=65° C.; ethylene pressure=400 psig; reaction time=20 min.

I—cocatalyst=Et$_2$AlCl; mol cat.=17.5×10$^{-7}$; solvent=toluene; temperature=100° C.; ethylene pressure=800 psig; reaction time=20 min.

flask was equipped with a magnetic stirring bar and a septum cap. Upon stirring, anhydrous toluene (80 mL) was then added, followed by 20.0 mL of a 1.8 M of DEAC in toluene. The suspension was heated to 80° C. for 4 hours, cooled to room temperature and then transferred via canula onto a filter funnel. The solid was washed with toluene (5×50 mL) and dried in vacuo to give 4.21 g solid. BET surface area: 280 m$^2$ g$^{-1}$. Pore volume: 1.0 cm$^3$ g$^{-1}$. Average Pore Diameter: 132 Å. Obsd wt % Al: 2.7.

Example 171

Preparation of triethylaluminum (TEAL) supported on silica (Grace Davison XPO-2402), TEAL/2402.

A 500-mL pear-shaped flask, previously heated to 200° C. for several hours and allowed to cool to room temperature under vacuum, was charged with silica (Grace Davison XPO-2402; 6.15 g) under a nitrogen inert atmosphere. The flask was equipped with a magnetic stirring bar and a septum cap. Upon stirring, anhydrous toluene (50 mL) was then added, followed by 100 mL of a 1.9 mL of TEAL in toluene. The suspension was heated to 80° C. for 4 hours, cooled to room temperature and then transferred via canula onto a filter funnel. The solid was washed with toluene (1×50 mL+4×25 mL) and dried in vacuo to give 6.34 g solid.

Example 172

Preparation of DEAC supported on silica (Grace Davison Sylopol 2212), DEAC/2212.

Solution Phase Polymerization

| Example | Catalyst | Procedure | Mass Polymer (g) | Total TO | M$_n$ | PDI | Branches/1000C ($^1$HNMR) | T$_m$ (° C.) |
|---|---|---|---|---|---|---|---|---|
| 160 | XXVII | A | 6 | 247K | 83K | 2.42 | 33 | 94 |
| 161 | XXVII | B | 9 | 370K | 135K | 2.61 | 26 | 113 |
| 162 | XXVII | C | 6 | 245K | 144K | 2.30 | 24 | 113 |
| 163 | XXVII | D | 5.7 | 116K | 66K | 1.85 | 47 | 80 |
| 164 | XXVII | E | 6.3 | 129K | 58K | 2.18 | 44 | 75 |
| 165 | XXVII | F | 7.8 | 159K | 63K | 2.43 | 37 | 95 |
| 166 | XXVII | G | 3.8 | 78K | 52K | 1.85 | — | 55 |
| 167 | XXVII | H | 5.5 | 112K | 78K | 1.93 | 45 | 78 |
| 168 | XXVII | I | 1.5 | 31K | 32K | 1.85 | 63 | 55 |

Example 169

Preparation of MAO supported on silica (Grace Davison XPO-2402), MAO/2402.

A 500-mL pear-shaped flask, previously heated to 200° C. for several hours and allowed to cool to room temperature under vacuum, was charged with silica (Grace Davison XPO-2402; 3.08 g) under a nitrogen inert atmosphere. The flask was equipped with a magnetic stirring bar and a septum cap. Upon stirring, anhydrous toluene (80 mL) was then added, followed by 19.0 mL of a 10 wt % of MAO in toluene. The suspension was heated to 80° C. for 4 hours, cooled to room temperature and then transferred via canula onto a filter funnel. The solid was washed with toluene (3×50 mL) and dried in vacuo to give 3.64 g solid. BET surface area: 300.9 m$^2$ g$^{-1}$. Pore volume: 1.19 cm$^3$ g$^{-1}$. Average Pore Diameter: 157.3 Å. Obsd wt % Al: 6.8.

Example 170

Preparation of diethylaluminum chloride (DEAC) supported on silica (Grace Davison XPO-2402) DEAC/2402.

A 500-mL pear-shaped flask, previously heated to 200° C. for several hours and allowed to cool to room temperature under vacuum, was charged with silica (Grace Davison XPO-2402; 3.87 g) under a nitrogen inert atmosphere. The A 500-mL pear-shaped flask, previously heated to 200° C. for several hours and allowed to cool to room temperature under vacuum, was charged with silica (Grace Davison Sylopol 2212; 3.08 g) under a nitrogen inert atmosphere. The flask was equipped with a magnetic stirring bar and a septum cap. Upon stirring, anhydrous toluene (80 mL) was then added, followed by 16 mL of a 10 wt % solution of MAO in toluene. The suspension was heated to 80° C. for 4 hours, cooled to room temperature and then transferred via canula onto a filter funnel. The solid was washed with toluene (1×50 mL+6×25 mL+1×50 mL) and dried in vacuo to give 3.35 g solid. Obsd wt % Al: 2.6.

Example 173

Preparation of MAO supported on silica (Grace Davison Sylopol 2212), MAO/2212.

A 500-mL pear-shaped flask, previously heated to 200° C. for several hours and allowed to cool to room temperature under vacuum, was charged with silica (Grace Davison Sylopol 2212; 6.27 g) under a nitrogen inert atmosphere. The flask was equipped with a magnetic stirring bar and a septum cap. Upon stirring, anhydrous toluene (50 mL) was then added, followed by 54 mL of a 10 wt % solution of MAO in toluene. The suspension was heated to 80° C. for 5 hours, cooled to room temperature and then transferred via

Example 174
Preparation of the nickel complex of 2,3-bis(2,6-dimethylphenylimino)-[1,4]-dithiane supported on MAO/2402, XXVII/MAO/2402.

A 50-mL pear-shaped flask, previously heated to 200° C. for several hours and allowed to cool to room temperature under vacuum, was charged with MAO/2402 (1.62 mg) and the nickel complex of 2,3-bis(2,6-dimethylphenylimino)-[1,4]-dithiane (46.7 mg; 81.2 $\mu$mol) under a nitrogen inert atmosphere. The flask was equipped with a magnetic stirring bar and a septum cap. The solid was cooled to 0° C. and dichloromethane (20 mL) was added under vigorous stirring. The volatiles were removed in vacuum. The residual solid was dried in vacuo to give 1.40 g.

Example 175
Preparation of the nickel complex of 2,3-bis(2,6-dimethylphenylimino)-[1,4]-dithiane supported on DEAC/2402 XXVII/DEAC/2402.

A 50-mL pear-shaped flask, previously heated to 200° C. for several hours and allowed to cool to room temperature under vacuum, was charged with DEAC/2402 (637 mg) and the nickel complex of 2,3-bis(2,6-dimethylphenylimino)-[1,4]-dithiane (18.0 mg; 31.3 $\mu$mol) under a nitrogen inert atmosphere. The flask was equipped with a magnetic stirring bar and a septum cap. The solid was cooled to 0° C. and dichloromethane (25 mL) was added under vigorous stirring. After 1 hour, the mixture was filtered by canula. The residual solid was then rinsed with 10 mL dichloromethane and filtered by canula a second time. The solid was dried in vacuo and stored at −30° C. Yield: 213.4 mg. Loading of Ni complex/g support: 43 $\mu$mol (based on Ni analysis) and 37 $\mu$mol (based on S analysis), Ni complex:Al ratio: 22 (based on Ni analysis) and 26 (based on S analysis).

Example 176
Preparation of the nickel complex of 2,3-bis(2,6-dimethylphenylimino)-[1,4]-dithiane supported on DEAC/2212, XXVII/DEAC/2212.

A 100-mL pear-shaped flask, previously heated to 200° C. for several hours and allowed to cool to room temperature under vacuum, was charged with DEAC/2212 (758 mg) and the nickel complex of 2,3-bis(2,6-dimethylphenylimino)-[1,4]-dithiane (22.1 mg; 38.4 $\mu$mol) under a nitrogen inert atmosphere. The flask was equipped with a magnetic stirring bar and a septum cap. The solid was cooled to 0° C. and dichloromethane (25 mL) was added under vigorous stirring. After 1 hour, the mixture was filtered by canula. The residual solid was then rinsed with 10 mL dichloromethane and filtered by canula a second time. The solid was dried in vacuo and stored at −30° C. Yield: 718 mg. Loading of Ni complex/g support: 49 $\mu$mol (based on Ni analysis) and 34 $\mu$mol (based on S analysis). Ni complex:Al ratio: 20 (based on Ni analysis) and 28 (based on S analysis).

Example 177
Treatment of the nickel complex of 2,3-bis(2,6-dimethylphenylimino)-[1,4]-dithiane supported on DEAC/2212 with trimethylaluminum (TMAL), TMAL/XXVII/DEAC/2212.

A 200-mL pear-shaped flask, previously heated to 200° C. for several hours and allowed to cool to room temperature under vacuum, was charged with the nickel complex of 2,3-bis(2,6-dimethylphenylimino)-[1,4]-dithiane supported on DEAC/2212, XXVII/DEAC/2212 (81.5 mg; 3.4 $\mu$mol Ni) under a nitrogen inert atmosphere. The flask was equipped with a magnetic stirring bar and a septum cap. The solid was cooled to 0° C. and toluene (25 mL) was added under vigorous stirring. After 15 min, the volatile materials were removed in vacuo at 0° C. The resulting solid was further used to evaluate activity towards ethylene polymerization.

Example 178
Treatment of the nickel complex of 2,3-bis(2,6-dimethylphenylimino)-[1,4]-dithiane supported on DEAC/2212 with MAO, MAO/XXVII/DEAC/2212.

A 50-mL pear-shaped flask, previously heated to 200° C. for several hours and allowed to cool to room temperature under vacuum, was charged with the nickel complex of 2,3-bis(2,6-dimethylphenylimino)-[1,4]-dithiane supported on DEAC/2212, XXVII/DEAC/2212 (113.6 mg; 4.8 $\mu$mol Ni) under a nitrogen inert atmosphere. The flask was equipped with a magnetic stirring bar and a septum cap. The solid was cooled to 0° C. and toluene (25 mL) was added under vigorous stirring. After 2 min, the suspension was transferred via canula onto a filter funnel. The resulting solid was dried in vacuo (89 mg) and used to evaluate activity towards ethylene polymerization.

Example 179

Polymerization of ethylene using XXVII/MAO/2402

A 50-mL pear-shaped flask was charged with 152.5 mg XXVII/MAO/2402 (38 $\mu$mol Ni/g; 5.8 $\mu$mol) under a nitrogen inert atmosphere. The inert atmosphere was replaced by 1 atm ethylene and toluene (25 mL) was added. The suspension was stirred for 2 hours at room temperature. The reaction was then quenched with acetone and 6M HCl. The mixture was filtered. The resulting solid was collected and dried in vacuo at 100° C. to give 626.5 mg.

Example 180
Polymerization of ethylene using XXVII/MAO/2402

A 1000-mL Parr® stirred reactor was charged with 169.3mg (38 $\mu$mol Ni/g; 6.4 $\mu$mol Ni) under a nitrogen inert atmosphere. Toluene (250 mL) was added and the reactor pressurized with ethylene (800 psig). The mixture was stirred at 40° C. for 60 min. The vessel was vented and the catalyst quenched with methanol and 6 M HCl The mixture was filtered and the collected solid dried in vacuo at 100° C. to give 18.60 g polymer.

Example 181
Polymerization of ethylene using XXVII/MAO/2402

A 200-mL pear-shaped flask was charged with 79.3 mg XXVII/MAO/2402 (38 ||mol Ni/g; 3.0 $\mu$mol) under a nitrogen inert atmosphere. The inert atmosphere was replaced by 1 atm ethylene and toluene (50 mL) was added, followed by 2.0 mL MAO (10 wt % in toluene). The suspension was stirred for 11 min at room temperature and then quenched with methanol and 6M HCl. The mixture was filtered. The resulting solid was collected and dried in vacuo at 100° C. to give 643 mg. $M_n$=100.5K, $M_w$=325.3K, $M_w/M_n$=3.2; 41 branches/1000 C (by $^1$H NMR); $T_m$=83° C. (by DSC).

Example 182
Polymerization of ethylene using XXVII/MAO/2402

A 600-mL Parr® stirred reactor was charged with 72.1 mg XXVII/MAO/2402 (38 $\mu$mol Ni/g; 2.7 $\mu$mol Ni) under a nitrogen inert atmosphere. The reactor was then charged with 150 mL anhydrous toluene and heated to 50° C. I then added 2.0 mL of a 10 wt % solution of MAO in toluene. The vessel was pressurized with 100 psig ethylene and further heated to 69° C. The slurry agitated for 45 min. The mixture was quenched at elevated pressure by addition of methanol through an injection loop. The vessel was depressurized and the mixture treated with 6M HCl. The polymer was isolated by filtration and dried in vacuo at 100° C. to give 4.21 g polymer. $M_n$=55.7K. $M_w$=651.5K, $M_w/M_n$=11.7; 32 branches/1000 C (by $^1$H NMR); $T_m$=113° C. (by DSC).

Example 183
Polymerization of ethylene using XXVII/MAO/2402

A 200-mL pear-shaped flask was charged with 57.5 mg XXVII/MAO/2402 (38 μmol Ni/g; 2.2 μmol) and 645 mg of MAO-treated silica (purchased from Witco TA 02794/HL/04). The nitrogen inert atmosphere was replaced by 1 atm ethylene, and 50 mL anhydrous toluene was then added. The suspension was stirred for 1 hour at room temperature before being quenched with acetone and 6M HCl. The mixture was filtered and the collected solid dried in vacuo at 100° C. to give 478 mg. $M_n$=195.5K, $M_n$=840.5K, $M_w/M_n$=4.3; 16 branches/1000 C; $T_m$=116° C. (by DSC).

Example 184
Polymerization of ethylene using XXVII/MAO/2402

A 600-mL Parr® stirred reactor was charged with 65.0 mg XXVII/MAO/2402 (38 μmol Ni/g; 2.5 μmol Ni), 170 mg solid MAO and 214 g sodium chloride under a nitrogen inert atmosphere. The reactor was heated to 60° C., and subsequently pressurized with 100 psig ethylene. The mixture was further heated to 65° C. and stirred for an additional 45 min. The vessel was vented and the solid mixed with water. The mixture was filtered and the solid washed with water, 6M HCl and methanol. The collected polymer was dried in vacuo at 100° C. to give 2.38 g polymer. $M_w$=65.7K, $M_w$=487.0K, $M_w/M_n$=7.4; 29 branches/1000 C (by $^1$H NMR); $T_m$=118° C. (by DSC).

Example 185
Polymerization of ethylene using XXVII/DEAC/2402

A 200-mL pear-shaped flask was charged with 82 mg XXVII/DEAC/2402 (40 μmol Ni/g; 3.3 μmol) under a nitrogen inert atmosphere. Toluene (30 mL) was added. The inert atmosphere was then replaced by 1 atm ethylene. The suspension was stirred for 2 hours at room temperature. The reaction was then quenched with acetone and 6M HCl. The mixture was filtered. The resulting solid was collected and dried in vacuo at 100° C. to give 418 mg. $M_n$=114.0K, $M_n$=264.7K, $M_w/M_n$=2.3; 65 branches/1000 C (by $^1$H NMR); $T_m$=110° C. (by DSC).

Example 186
Polymerization of ethylene using XXVII/DEAC/2402

A 600-mL Parr® stirred reactor was charged with 80.2 mg (40 μmol Ni/g; 3.2 μmol Ni) under a nitrogen inert atmosphere. Toluene (150 mL) was added and the reactor pressurized with ethylene (800 psig). The mixture was stirred at 40° C. for 58 min. The vessel was vented and the catalyst quenched with methanol and 6 M HCl The mixture was filtered and the collected solid dried in vacuo at 100° C. to give 0.56 g polymer. $M_n$=246.5K, $M_w$=524.4K, $M_w/M_n$=2.1; 9 branches/1000 C (by $^1$H NMR); $T_m$=127° C. (by DSC).

Example 187
Polymerization of ethylene using XXVII/DEAC/2212

A 200-mL pear-shaped flask was charged with 89.1 mg XXVII/DEAC/2212 (42 μmol Ni/g; 3.7 μmol) under a nitrogen inert atmosphere. The inert atmosphere was replaced by 1 atm ethylene and toluene (50 mL) was added, followed by 2.0 mL MAO (10 wt % in toluene). The suspension was stirred for 10 min at room temperature. Temperature was controlled with a water bath. The reaction was then quenched with acetone and 6M HCl. The mixture was filtered. The resulting solid was collected and dried in vacuo at 100° C. to give 1.80 g. $M_n$=132.8K, $M_w$=272.1K, $M_w/M_n$=2.0; 52 branches/1000 C (by $^1$H NMR); $T_m$=57° C. (by DSC).

Example 188
Polymerization of ethylene using XXVII/DEAC/2212

A 200-mL pear-shaped flask was charged with 81.2 mg XXVII/DEAC/2212 (42 μmol Ni/g; 3.4 μmol) under a nitrogen inert atmosphere. The inert atmosphere was replaced by 1 atm ethylene and toluene (50 mL) was added, followed by 2.0 mL DEAC (1.8 M in toluene). The suspension was stirred for 6 min at room temperature. Temperature was controlled with a water bath. The reaction was then quenched with acetone and 6M HCl. The mixture was filtered. The resulting solid was collected and dried in vacuo at 100° C. to give 857 mg. $M_n$=179.2K, $M_n$=444.7K, $M_w/M_n$=2.5; 32 branches/1000 C (by $^1$H NMR); $T_m$=110° C. (by DSC).

Example 189
Polymerization of ethylene using TMAL/XXVII/DEAC/2212

A suspension of TMAL/XXVII/DEAC/2212 (3.4 μmol Ni) in toluene (50 mL) was then prepared at 0° C. The reaction flask was evacuated and backfilled with 1 atm ethylene. The mixture was stirred at room temperature for 2 hours and then quenched with methanol and 6M HCl. The mixture was filtered. The resulting solid was collected and dried in vacuo at 100° C. to give 212 mg. $M_n$=215.9K, $M_w$=910.6K, $M_w/M_n$=4.2; 15 branches/1000 C (by $^1$H NMR); $T_m$=117° C. (by DSC).

Example 190
Polymerization of ethylene using MAO/XXVII/DEAC/2212

A 200-mL pear-shaped flask was charged with MAO/XXVII/DEAC/2212 (2.9 μmol) and toluene (50 mL) under a nitrogen inert atmosphere. The flask was evacuated and backfilled with 1 atm ethylene. The suspension was stirred for 2.5 hours before it was quenched with methanol and 6 M HCl. The mixture was filtered and the collected solid dried at 100° C. to give 304 mg. $M_n$=59.9K, $M_w$=487.3K, $M_w/M_n$=8.1; $T_m$=125° C. (by DSC).

We claim:

1. A composition comprising (a) a Group 8–10 transition metal M, (b) one or more Lewis acids, and (c) a binucleating or multinucleating compound of the formula X:

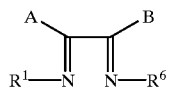

X wherein the Lewis acid or acids are bound to one or more heteroatoms which are π-conjugated to the donor atom or atoms bound to the transition metal M;

$R^1$ and $R^6$ each, independently, represent sterically hindered aryl;

N represents nitrogen;

A and B are each, independently, a heteroatom connected mono-radical wherein the connected heteroatom is selected from Group 15 or 16; in addition, A and B may be linked by a bridging group.

2. The composition as in claim 1 wherein the transition metal is Ni(II), the Lewis acid is a boron or aluminum containing Lewis acid and the binucleating or multinucleating compound of formula X is selected from

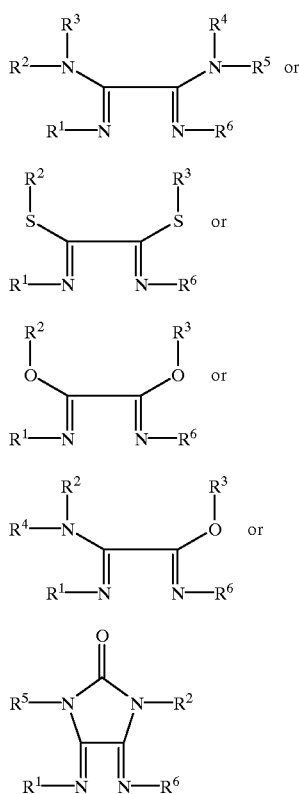

wherein $R^1$ and $R^6$ each, independently, represent sterically hindered aryl;

$R^2$, $R^3$, $R^4$ and $R^5$ each, independently, represent a hydrogen, hydrocarbyl, substituted hydrocarbyl, or silyl; in addition, any two of $R^2$, $R^3$, $R^4$, and $R^5$ may collectively form a bridging group, provided that when the compound is of formula VI or IX, the bridging group is not a substituted sulfur atom or a substituted phosphorous atom; and N represents nitrogen; O represents oxygen, and S represents sulfur.

3. A compound of the formula I:

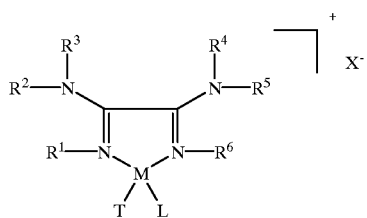

wherein $R^1$ and $R^6$ each, independently, represent hydrocarbyl, substituted hydrocarbyl, or silyl;

$R^2$, $R^3$, $R^4$ and $R^5$ each, independently, represent a hydrogen, hydrocarbyl, substituted hydrocarbyl, or silyl; in addition, any two of $R^2$, $R^3$, $R^4$, and $R^5$ may collectively form a bridging group;

T represents a hydrogen or hydrocarbyl;

L represents a mono-olefin or a neutral Lewis base wherein the coordinated atom is nitrogen, oxygen, or sulfur;

M represents Ni(II), Pd(II), Co(II), or Fe(II);

N represents nitrogen; and $X^-$ is a weakly coordinating anion.

4. A compound of formula II:

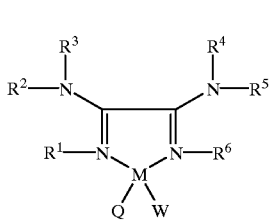

wherein $R^1$ and $R^6$ each independently, represent a sterically hindered aryl;

$R^2$, $R^3$, $R^4$ and $R^5$ each, independently, represent a hydrogen, hydrocarbyl, substituted hydrocarbyl, or silyl; in addition, any two of $R^2$, $R^3$, $R^4$, and $R^5$ may collectively form a bridging group;

Q represents a hydrocarbyl, chloride, iodide or bromide;

W represents a hydrocarbyl, chloride, iodide or bromide;

N represents nitrogen; and

M represents Ni(II), Pd(II), Co(II), or Fe(II).

5. A compound of formula IV:

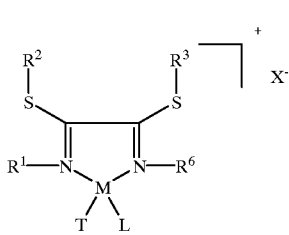

wherein $R^1$ and $R^6$ each, independently, represent hydrocarbyl, substituted hydrocarbyl, or silyl;

$R^2$ and $R^3$ each, independently, represent a hydrogen, hydrocarbyl, substituted hydrocarbyl, or silyl, and, in addition, may collectively form a bridging hydrocarbyl, bridging substituted hydrocarbyl, or a substituted silicon atom;

T represents a hydrogen or hydrocarbyl;

L represents a mono-olefin or a neutral Lewis base wherein the coordinated atom is nitrogen, oxygen, or sulfur;

M represents Ni(II), Pd(II), Co(II), or Fe(II);

N represents nitrogen; and $X^-$ is a weakly coordinating anion.

6. A compound of formula V:

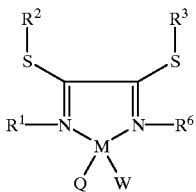

V wherein R¹ and R⁶ each, independently, represent sterically hindered aryl;

R² and R³ each, independently, represent a hydrogen, hydrocarbyl, substituted hydrocarbyl, or silyl, and, in addition, may collectively form a bridging hydrocarbyl, bridging substituted hydrocarbyl, or a substituted silicon atom;

Q represents a hydrocarbyl, chloride, iodide or bromide;

W represents a hydrocarbyl, chloride, iodide or bromide;

N represents nitrogen; and

M represents Ni(II), Pd(II), Co(II), or Fe(II).

7. A compound of the formula VII:

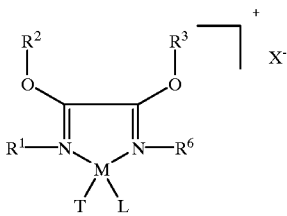

VII wherein R¹ and R⁶ each, independently, represent hydrocarbyl, substituted hydrocarbyl, or silyl;

R² and R³ each, independently, represent a hydrogen, hydrocarbyl, substituted hydrocarbyl, or silyl, and, in addition, may collectively form a bridging hydrocarbyl, bridging substituted hydrocarbyl, or a substituted silicon atom;

T represents a hydrogen or hydrocarbyl;

L represents a mono-olefin or a neutral Lewis base wherein the coordinated atom is nitrogen, oxygen, or sulfur;

M represents Ni(II), Pd(II), Co(II), or Fe(II);

N represents nitrogen; and

X⁻ is a weakly coordinating anion.

8. A compound of formula VIII:

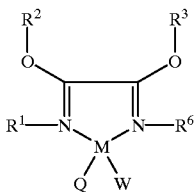

VIII wherein R¹ and R⁶ each, independently, represent a sterically hindered aryl;

R² and R³ each, independently, represent a hydrogen, hydrocarbyl, substituted hydrocarbyl, or silyl, and, in addition, may collectively form a bridging hydrocarbyl, bridging substituted hydrocarbyl, or a substituted silicon atom;

Q represents a hydrocarbyl, chloride, iodide or bromide;

W represents a hydrocarbyl, chloride, iodide or bromide;

N represents nitrogen; and

M represents Ni(II), Pd(II), Co(II), or Fe(II).

9. A compound of the formula XIII:

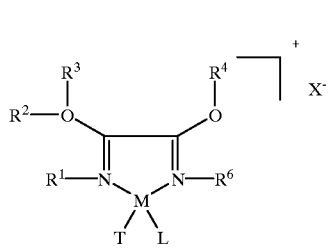

XIII wherein R¹ and R⁶ each, independently, represent hydrocarbyl, substituted hydrocarbyl, or silyl;

R², R³, and R⁴ each, independently, represent a hydrogen, hydrocarbyl, substituted hydrocarbyl, or silyl, and, in addition, any two of R², R³, and R⁴ may collectively form a bridging group;

T represents a hydrogen or hydrocarbyl;

L represents a mono-olefin or a neutral Lewis base wherein the coordinated atom is nitrogen, oxygen, or sulfur;

M represents Ni(II), Pd(II), Co(II), or Fe(II);

N represents nitrogen; and

X⁻ is a weakly coordinating anion.

10. A compound of formula XV:

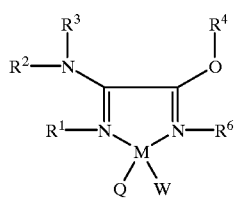

XV wherein R¹ and R⁶ each, independently, represent a sterically hindered aryl;

R², R³, and R⁴ each, independently, represent a hydrogen, hydrocarbyl, substituted hydrocarbyl, or silyl, and, in addition, any two of R², R³, and R⁴ may collectively form a bridging group;

Q represents a hydrocarbyl, chloride, iodide or bromide;

W represents a hydrocarbyl, chloride, iodide or bromide;

N represents nitrogen; and

M represents Ni(II), Pd(II), Co(II), or Fe(II).

11. A compound of the formula XIV:

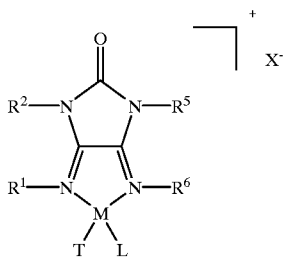

XIV wherein $R^1$ and $R^6$ each, independently, represent hydrocarbyl, substituted hydrocarbyl, or silyl;

$R^2$ and $R^5$ each, independently, represent a hydrogen, hydrocarbyl, substituted hydrocarbyl, or silyl;

T represents a hydrogen or hydrocarbyl;

L represents a mono-olefin or a neutral Lewis base wherein the coordinated atom is nitrogen, oxygen, or sulfur;

M represents Ni(II), Pd(II), Co(II), or Fe(II);

N represents nitrogen; and $X^-$ is a weakly coordinating anion.

12. A compound of formula XVI:

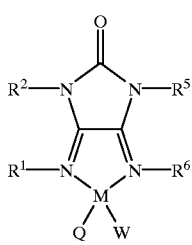

XVI wherein $R^1$ and $R^6$ each, independently, represent a sterically hindered aryl;

$R^2$ and $R^5$ each, independently, represent a hydrogen, hydrocarbyl, substituted hydrocarbyl, or silyl;

Q represents a hydrocarbyl, chloride, iodide or bromide;

W represents a hydrocarbyl, chloride, iodide or bromide;

N represents nitrogen; and

M represents Ni(II), Pd(II), Co(II), or Fe(II).

13. A compound of the formula XIX:

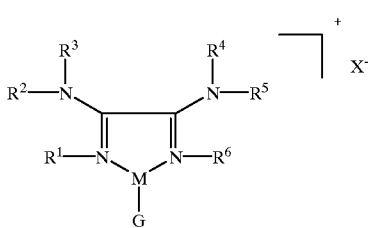

XIX wherein $R^1$ and $R^6$ each, independently, represent hydrocarbyl, substituted hydrocarbyl, or silyl;

$R^2$, $R^3$, $R^4$ and $R^5$ each, independently, represent a hydrogen, hydrocarbyl, substituted hydrocarbyl, or silyl; in addition, any two of $R^2$, $R^3$, $R^4$, and $R^5$ may collectively form a bridging group;

G is a π-allyl or π-benzyl group;

M represents Ni(II) or Pd(II);

N represents nitrogen; and $X^-$ is a weakly coordinating anion.

14. A compound of formula XX:

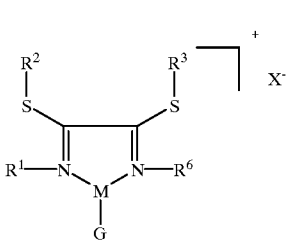

XX wherein $R^1$ and $R^6$ each, independently, represent hydrocarbyl, substituted hydrocarbyl, or silyl;

$R^2$ and $R^3$ each, independently, represent a hydrogen, hydrocarbyl, substituted hydrocarbyl, or silyl, and, in addition, may collectively form a bridging hydrocarbyl, bridging substituted hydrocarbyl, or a substituted silicon atom;

G is a π-allyl or π-benzyl;

M represents Ni(II), Pd(II);

N represents nitrogen; and $X^-$ is a weakly coordinating anion.

15. A compound of the formula XXI:

XXI wherein $R^1$ and $R^6$ each, independently, represent hydrocarbyl, substituted hydrocarbyl, or silyl;

$R^2$ and $R^3$ each, independently, represent a hydrogen, hydrocarbyl, substituted hydrocarbyl, or silyl, and, in addition, may collectively form a bridging hydrocarbyl, bridging substituted hydrocarbyl, or a substituted silicon atom;

G is a π-allyl or π-benzyl;

M represents Ni(II), Pd(II);

N represents nitrogen; and $X^-$ is a weakly coordinating anion.

16. A compound of the formula XXII:

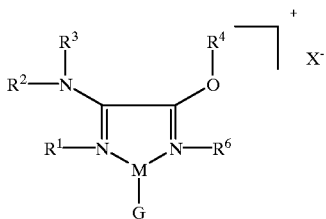

XXII wherein $R^1$ and $R^6$ each, independently, represent hydrocarbyl, substituted hydrocarbyl, or silyl;
$R^2$, $R^3$, and $R^4$ each, independently, represent a hydrogen, hydrocarbyl, substituted hydrocarbyl, or silyl, and, in addition, may collectively form a bridging group;
G is a π-allyl or π-benzyl;
M represents Ni(II) or Pd(II);
N represents nitrogen; and
X⁻ is a weakly coordinating anion.

17. A compound of the formula XXIII:

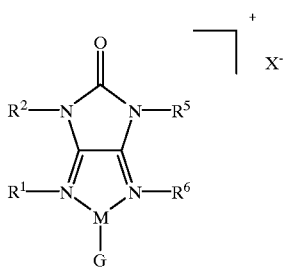

XXIII wherein $R^1$ and $R^6$ each, independently, represent hydrocarbyl, substituted hydrocarbyl, or silyl;
$R^2$ and $R^3$ each independently, represent a hydrogen, hydrocarbyl, substituted hydrocarbyl, or silyl;
G is a π-allyl or π-benzyl;
M represents Ni(II), Pd(II);
N represents nitrogen; and
X⁻ is a weakly coordinating anion.

18. A compound of formula XXIV,

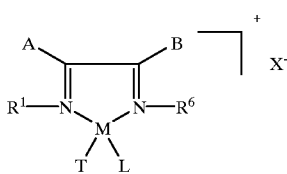

XXIV wherein $R^1$ and $R^6$ each, independently, represent hydrocarbyl, substituted hydrocarbyl, or silyl;
A and B are each, independently, a heteroatom connected mono-radical wherein the connected heteroatom is selected from Group 15 or 16; in addition, A and B may be linked by a bridging group;

T represents a hydrogen or a hydrocarbyl;
L represents a mono-olefin or a neutral Lewis base wherein the coordinated atom is nitrogen, oxygen, or sulfur;
M represents Ni(II) or Pd(II);
N represents nitrogen; and
X⁻ is a weakly coordinating anion.

19. A compound of formula XXIX,

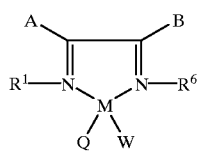

XXIX wherein $R^1$ and $R^6$ each, independently, represent a sterically hindered aryl;
A and B are each, independently, a heteroatom connected mono-radical wherein the connected heteroatom is selected from Group 15 or 16; in addition, A and B may be linked by a bridging group;
Q represents a hydrocarbyl, chloride, iodide or bromide;
W represents a hydrocarbyl, chloride, iodide or bromide;
M represents Ni(II) or Pd(II); and
N represents nitrogen.

20. The compound of claim 5 having the formula XXV:

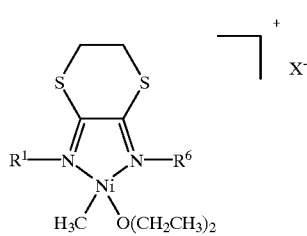

XXV wherein $R^1$ and $R^6$ are 2,6-dimethylphenyl;
and X⁻ is a weakly coordinating anion.

21. The compound of claim 5 having the formula XXVI:

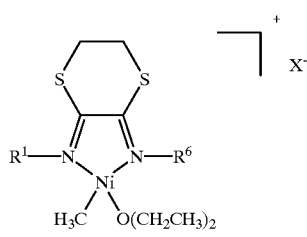

XXVI wherein $R^1$ and $R^6$ are 2,6-diisopropylphenyl;
and X⁻ is a weakly coordinating anion.

22. The compound of claim 6 having the formula XXVII,

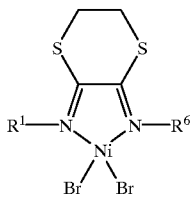
XXVII wherein $R^1$ and $R^6$ are 2,6-dimethylphenyl.

23. The compound of claim 6 having the formula XXVIII,

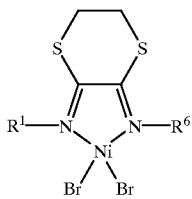
XXVIII wherein $R^1$ and $R^6$ are 2,6-diisopropylphenyl.

24. The compound of claim 7 having the formula XXX,

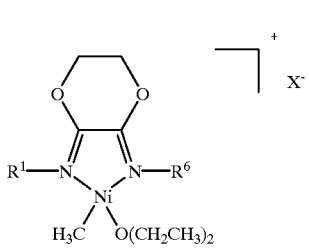
XXX wherein $R^1$ and $R^6$ are 2,6-dimethylphenyl;
and $X^-$ is a weakly coordinating anion.

25. The compound of claim 7 having the formula XXXI,

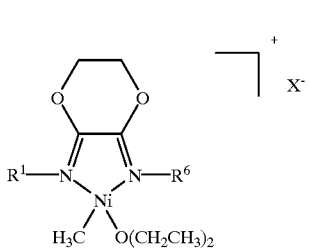
XXXI wherein $R^1$ and $R^6$ are 2,6-diisopropylphenyl;
and $X^-$ is a weakly coordinating anion.

26. The compound of claim 8 having the formula XXXII,

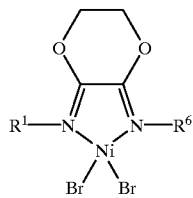
XXXII wherein $R^1$ and $R^6$ are 2,6-dimethylphenyl.

27. The compound of claim 8 having the formula XXXIII,

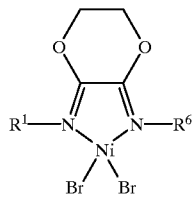
XXXIII wherein $R^1$ and $R^6$ are 2,6-diisopropylphenyl.

28. The compound of claim 7 having the formula XXXIV,

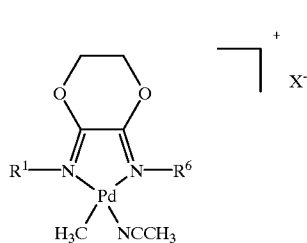
XXXIV wherein $R^1$ and $R^6$ are 2,6-diisopropylphenyl;
and $X^-$ is a weakly coordinating anion.

29. The compound of claim 5 having the formula XXXV,

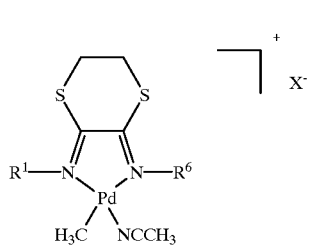
XXXV wherein $R^1$ and $R^6$ are 2,6-diisopropylphenyl;
and $X^-$ is a weakly coordinating anion.

30. The compound of claim 9 having the formula XXXVI,

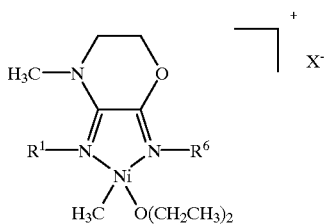
XXXVI wherein $R^1$ and $R^6$ are 2,6-dimethylphenyl;
and $X^-$ is a weakly coordinating anion.

31. The compound of claim 9 having the formula XXXVII,

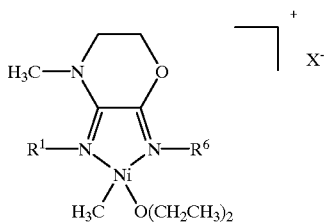
XXXVII wherein $R^1$ and $R^6$ are 2,6-diisopropylphenyl;
and $X^-$ is a weakly coordinating anion.

32. The compound of claim 10 having the formula XXXVIII,

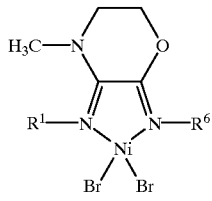
XXXVIII wherein $R^1$ and $R^6$ are 2,6-dimethylphenyl.

33. The compound of claim 10 having the formula XXXIX,

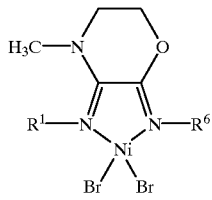
XXXIX wherein $R^1$ and $R^6$ are 2,6-diisopropylphenyl.

34. The compound of claim 11 having the formula XL,

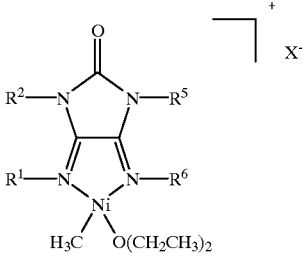
XL wherein $R^1$, $R^2$, $R^5$ and $R^6$ are 2,6-dimethyl-4-methoxyphenyl;
and $X^-$ is a weakly coordinating anion.

35. The compound of claim 12 having the formula XLI,

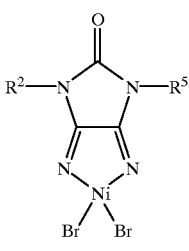
XLI wherein $R^1$, $R^2$, $R^5$ and $R^6$ are 2,6-dimethyl-4-methoxyphenyl.

36. The compound of claim 4 wherein M is Ni(II).

37. A supported catalyst comprising the reaction product of a compound of formula V, VIII, or XV:

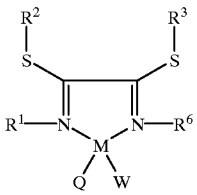
V

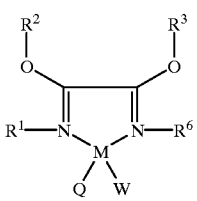
VIII

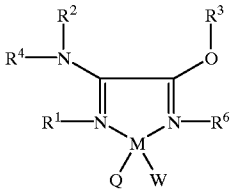
XV wherein $R^1$ and $R^6$ each, independently, represent a sterically hindered aryl;

R² and R³ each, independently, represent a hydrogen, hydrocarbyl, substituted hydrocarbyl, or silyl, and, in addition, may collectively form a bridging hydrocarbyl, bridging substituted hydrocarbyl, or a substituted silicon atom;

Q represents a hydrocarbyl, chloride, iodide or bromide;

W represents a hydrocarbyl, chloride, iodide or bromide;

N represents nitrogen; and

M represents Ni(II), Pd(II), Co(II), or Fe(II);

with a solid support which has been pre-treated with a compound Y, wherein Y is selected from the group consisting of a neutral Lewis acid capable of abstracting Q⁻ or W⁻ to form a weakly coordinating anion, a cationic Lewis acid whose counterion is a weakly coordinating anion, and a Bronsted acid whose conjugate base is a weakly coordinating anion.

38. The supported catalyst of claim 37, wherein the compound of formula V, VII, or XV is selected from the group consisting of

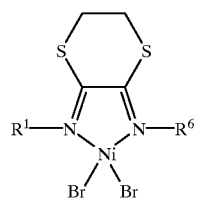

XXVII wherein $R^1$ and $R^6$ are 2,6-dimethylphenyl;

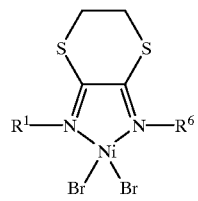

XXVIII wherein $R^1$ and $R^6$ are 2,6-diisopropylphenyl;

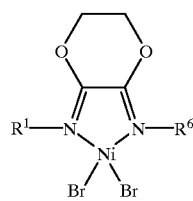

XXXII

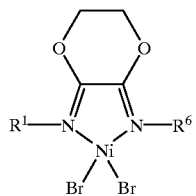

XXXIII wherein $R^1$ and $R^6$ are 2,6-dimethylphenyl;

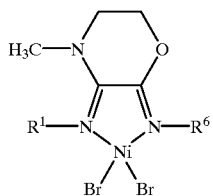

XXXVIII wherein $R^1$ and $R^6$ are 2,6-diisopropylphenyl;

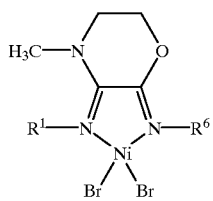

XXXIX wherein $R^1$ and $R^6$ are 2,6-dimethylphenyl; and wherein $R^1$ and $R^6$ are 2,6-diisopropylphenyl.

39. The supported catalyst of claim 37 comprising the reaction product of a compound of the formula XXVII,

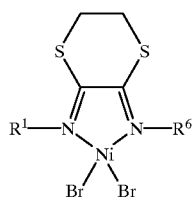

XXVII wherein $R^1$ and $R^6$ are 2,6-dimethylphenyl; with silica which has been pre-treated with methylaluminoxane.

40. The supported catalyst of claim 37 comprising the reaction product of a compound of the formula XXXII,

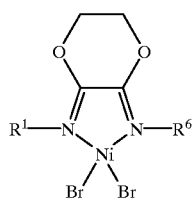

XXXII wherein R¹ and R⁶ are 2,6-dimethylphenyl; with silica which has been pre-treated with methylaluminoxane.

41. A supported catalyst formed by the reaction of
(a) a compound of formula V, VIII, or XV:

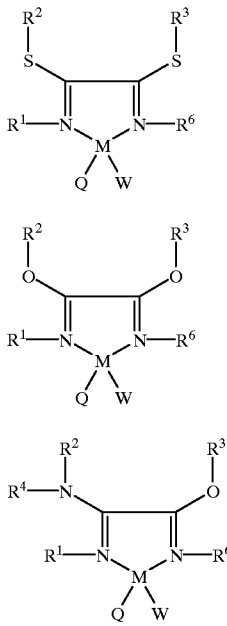

wherein $R^1$ and $R^6$ each, independently, represent a sterically hindered aryl;

$R^2$ and $R^3$ each, independently, represent a hydrogen, hydrocarbyl, substituted hydrocarbyl, or silyl, and, in addition, may collectively form a bridging hydrocarbyl, bridging substituted hydrocarbyl, or a substituted silicon atom;

Q represents a hydrocarbyl, chloride, iodide or bromide;
W represents a hydrocarbyl, chloride, iodide or bromide;
N represents nitrogen; and
M represents Ni(II), Pd(II), Co(II), or Fe(II);

(b) a solid support; and
(c) a compound Y, wherein Y is selected from the group consisting of a neutral Lewis acid capable of abstracting $Q^-$ or $W^-$ to form a weakly coordinating anion, a cationic Lewis acid whose counterion is a weakly coordinating anion, and a Bronsted acid whose conjugate base is a weakly coordinating anion.

42. The catalyst of claim 41, wherein the solid support is selected from the group consisting of talcs, silicas, titania, silica/chromia, silica/chromia/titania, silica/alumina, zirconia, aluminum phosphate gels, silanized silica, silica hydrogels, silica xerogels, silica aerogels, silica co-gels, montmorillonite clay and Y is a compound selected from the group consisting of methylaluminoxane and other aluminum sesquioxides having the formulas $R^7_3Al$, $R^7_2AlCl$, and $R^7AlCl_2$, wherein $R^7$ is alkyl.

43. The supported catalyst of claim 41, wherein the compound of formula V, VIII, or XV is selected from the group consisting of:

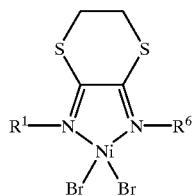

XXVII wherein $R^1$ and $R^6$ are 2,6-dimethylphenyl;

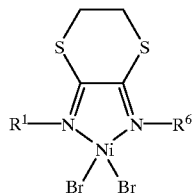

XXVIII wherein $R^1$ and $R^6$ are 2,6-diisopropylphenyl;

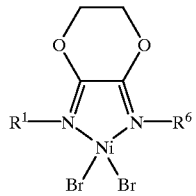

XXXII wherein $R^1$ and $R^6$ are 2,6-dimethylphenyl;

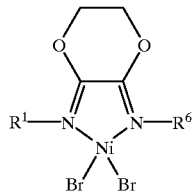

XXXIII wherein R¹ and R⁶ are 2,6-diisopropylphenyl;

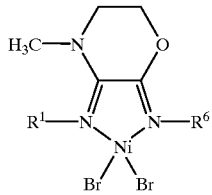

XXXVIII wherein R¹ and R⁶ are 2,6-dimethylphenyl; and

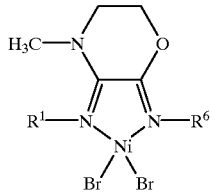

XXXIX wherein R¹ and R⁶ are 2,6-diisopropylphenyl.

44. The supported catalyst of claim 41 comprising the reaction product of a compound of the formula XXVII,

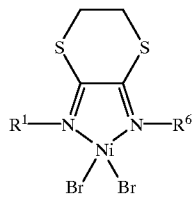

XXVII wherein R¹ and R⁶ are 2,6-dimethylphenyl; with silica and with methylaluminoxane.

45. The supported catalyst of claim 41 comprising the reaction product of a compound of the formula XXXII,

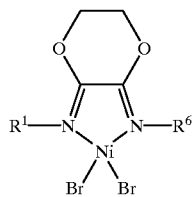

XXXII wherein R¹ and R⁶ are 2,6-dimethylphenyl; with silica and with methylaluminoxane.

* * * * *